(12) United States Patent
Cerundolo et al.

(10) Patent No.: US 8,188,313 B2
(45) Date of Patent: May 29, 2012

(54) ANALOGS OF ALPHA GALACTOSYLCERAMIDE AND USES THEREOF

(75) Inventors: Vincenzo Cerundolo, Oxford (GB);
Richard Schmidt, Konstanz (DE);
Gopal Reddy, Stony Brook, NY (US);
Rengarajan Balamurugan, Hyderabad (IN); Gerd Ritter, New York, NY (US);
Gurdyal Besra, Birmingham (GB);
Mariolina Salio, Oxford (GB);
Jonathan Silk, Oxford (GB)

(73) Assignees: The University of Birmingham, Birmingham (GB); Chancellor Masters and Scholars of the University of Oxford, Oxford (GB); Ludwig Institute for Cancer Research, New York, NY (US)

( * ) Notice: Subject to any disclaimer, the term of this patent is extended or adjusted under 35 U.S.C. 154(b) by 0 days.

(21) Appl. No.: 13/231,403

(22) Filed: Sep. 13, 2011

(65) Prior Publication Data
US 2012/0034269 A1    Feb. 9, 2012

Related U.S. Application Data

(62) Division of application No. 12/083,673, filed as application No. PCT/US2006/041592 on Oct. 25, 2006, now Pat. No. 8,039,670.

(51) Int. Cl.
| | |
|---|---|
| C07C 233/18 | (2006.01) |
| C07C 233/20 | (2006.01) |
| C07C 305/20 | (2006.01) |
| C07F 9/09 | (2006.01) |
| A61K 31/66 | (2006.01) |
| A61K 31/661 | (2006.01) |
| A61K 31/16 | (2006.01) |

(52) U.S. Cl. .......... 564/192; 564/208; 558/30; 558/170; 514/76; 514/114; 514/517; 514/625; 514/627

(58) Field of Classification Search .................. None
See application file for complete search history.

*Primary Examiner* — Brian J Davis
(74) *Attorney, Agent, or Firm* — Abelman, Frayne & Schwab

(57) ABSTRACT

Compounds of formula

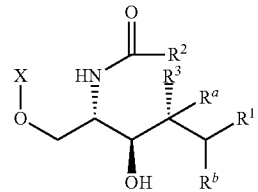

I wherein the variable are defined in the specification, are used in compositions which stimulate T cell responses.

7 Claims, 9 Drawing Sheets

ANALOGS OF ALPHA GALACTOSYLCERAMIDE AND USES THEREOF

RELATED APPLICATIONS

This application is a divisional of application Ser. No. 12/083,673 filed May 21, 2009, which is a §371 of PCT/US2006/041592 filed Oct. 25, 2006, now U.S. Pat. No. 8,039,670 and claims priority from U.S. Provisional Patent Applications Nos. 60/730,171 filed Oct. 25, 2005; 60/756,505 filed Jan. 5, 2006; and 60/761,110 filed Jan. 23, 2006.

FIELD OF THE INVENTION

This invention relates to new ceramide derivatives and their synthesis. These compounds are efficacious as immune stimulators, and have an effect that may be referred to as an immunomodulatory or adjuvant effect.

BACKGROUND OF THE INVENTION

α galactosylceramide, compound A, and its derivatives, have been known as biologically active agents for some time. See, e.g., U.S. Pat. No. 5,936,076 to Higa, et al., and U.S. Pat. No. 6,531,453 to Taniguchi, et al., describing several derivatives as anti-tumor agents as well as immunostimulators, both of these being incorporated by reference in their entirety.

Compound A:

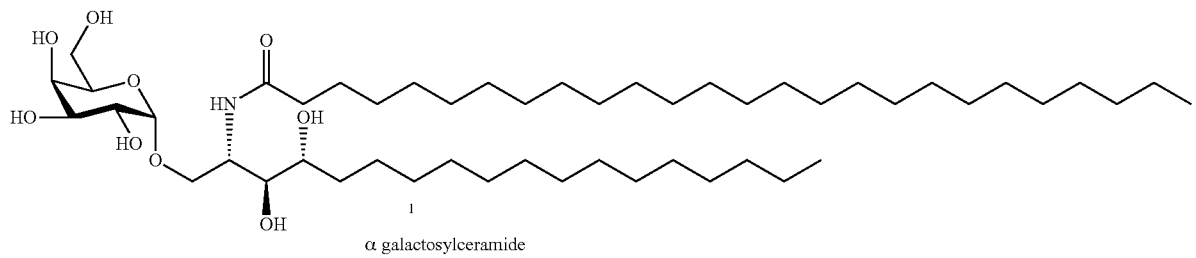

α galactosylceramide

The base compound, i.e., α-galactosylceramide or "αGal-Cer" hereafter is described by Nattori, et al., *Tetrahedron*, 50:2271 (1994), incorporated by reference, has itself been shown to inhibit tumor growth. See, Koejuka, et al., *Recent Res. Cancer*, 1:341 (1999). Sharif, et al., *Nature Med.*, 7:1057 (2001), and Hong, et al., *Nature Med.*, 7:1052 (2002), show efficacy against type I diabetes.

Study of the structure of αGal-Cer shows that it contains a sphingosine chain. Truncation of this chain has been shown, by Miyamoto, et al., *Nature*, 413:531 (2001), to result in a compound preventing autoimmune encephalomyelitis.

In parallel work it has been shown that natural killer T cells (NKT cells) recognize lipid antigens that are presented by the major histocompatibility complex-class I like protein, CD1d, for example. See, Godfrey et al., *J. Clin. Invest.*, 114:1379-1388 (2004).

Singh, et al., *J. Immunol.*, 163:2373 (1999), and Burdin, et al., *Eur. J. Immunol.*, 29:2014 (1999), have shown that αGal-Cer and CD1d potentiate Th2-mediated, adaptive immune responses, via activation of Vα14 natural killer T (NKT) cells.

The proposed mechanism by which αGal-Cer prevents disease is its ability to suppress interferon-gamma, but not interleukin-4, by NKT cells. See, e.g., Brossay, et al., *J. Exp. Med.*, 188:1521 (1998); Spada, et al., *J. Exp. Med.*, 188:1529 (1998), who showed the recognition of αGal-Cer by NKT cells, suggesting therapeutic efficacy in humans.

αGal-Cer has been developed as a potential therapeutic compound and taken into clinical testing, see, for example, Giaccone et al., *Clin Canc. Res.*, 8, 3702-3709 (2002). However, following treatment with αGal-Cer, the level of NKT cells in the peripheral blood of treated cancer patients treated fell to undetectable levels within 24 hours of treatment and failed to regain pretreatment levels within the remaining time course of the study.

Loss of circulating levels of NKT cells could represent a significant limitation therapeutically as it could suggest that therapeutic stimulation of NKT cells could not be used as a repeated treatment.

There is thus an interest in synthesis of analogues of αGal-Cer which act as stimulators of NKT cells but which do not lead to rapid loss of circulating levels of NKT cell populations after therapeutic administration.

Various publications describe synthesis of αGal-Cer and its derivatives. An exemplary, but by no means exhaustive list of such references includes Morita, et al., *J. Med. Chem.*, 38:2176 (1995); Sakai, at al., *J. Med. Chem.*, 38:1836 (1995); Morita, et al., *Bioorg. Med. Chem. Lett.*, 5:699 (1995); Takakawa, et al., *Tetrahedron*, 54:3150 (1998); Sakai, at al., *Org. Lett.*, 1:359 (1998); Figueroa-Perez, et al., *Carbohydr. Res.*, 328:95 (2000); Plettenburg, at al., *J. Org. Chem.*, 67:4559 (2002); Yang, at al., *Angew. Chem.*, 116:3906 (2004); Yang, at al., *Angew. Chem. Int. Ed.*, 43:3818 (2004); and, Yu, et al., *Proc. Natl. Acad. Sci. USA*, 102(9):3383-3388 (2005).

Studies have been conducted to examine the biological impact of the αGal-Cer molecule, when modifications of its structure were made. Higa, et al., supra, as well as, Zhou, at al., *Org. Lett.*, 4:1267 (2002); Schmieg, et al., *J. Exp. Med.*, 198:1631 (2003), Barbieri, a al., *J. Org. Chem.*, 468 (2004); and Fan, et al., *Tetrahedron*, 61:1855 (2005), are examples of the limited literature on this topic. Tsuji, et al., *J. Exp. Med.*, 198:1631 (2003), prepared a synthetic, C-glycoside analogue, i.e., α-C-Gal-Cer, which acts on NKT cells, in vivo, stimulating enhanced, Th1-type immune responses in mice. The protection against microbial infection and anti-tumor efficacy (Sköld, at al., *Infect. Immun.*, 71:5447 (2003); Sharif, et al., supra; Hong, at al., supra) are of special interest.

Additional work on the mechanism of action of these compounds is shown by, for example, Parekh, et al., *J. Immunol.*, 173:3693-3706 (2004), and Brossay, et al., supra.

Examples of US patents and patent applications or International patent applications describing instances of such derivatives and or the biological activity of αGal-Cer analogs include U.S. Pat. No. 5,936,076 to Higa, et al., and U.S. Pat. No. 6,531,453 to Taniguchi, et al., U.S. Pat. No. 5,853,737 to Modlin et al., US Patent Application 2003030611 to Jiang et al., US Patent Application 20030157135 to Tsuiji et al., US Patent Application 20040242499 to Uematsu et al and International Patent Applications describing No. PCT/JP20021008280 to Yamamura et al.

Essentially all of these prior examples describe analog structures based on αGal-Cer. Identification and characterization of molecules which are not glycolipids, such as αGal-Cer and its analogs, has been limited. Examples of patent applications describing structures which do not appear to be analogous to αGal-Cer include acyl peptides of US Patent Application No. 20040265976 to Moody et al., and JP Patent Application 34540997 to Masunaga et al.

We have now found a novel group of compounds that substantially mimic the binding properties of α-GalCer with the human CD1d molecule, but differs significantly in the interaction with T-cell receptors (TCR), leading to unexpected and advantageous properties compared to α-GalCer.

Affinity and kinetics of iNKT TCR binding to hCD1d complexed with α-GalCer or OCH. Increasing concentrations from 0.4 µM to 194 µM (two-fold dilution) of iNKT TCR were injected for 5 seconds over the indicated hCD1d-GSL complexes. The binding responses of 5 concentrations are shown superimposed. The panels on the right show binding response at equilibrium.

Figure 3:
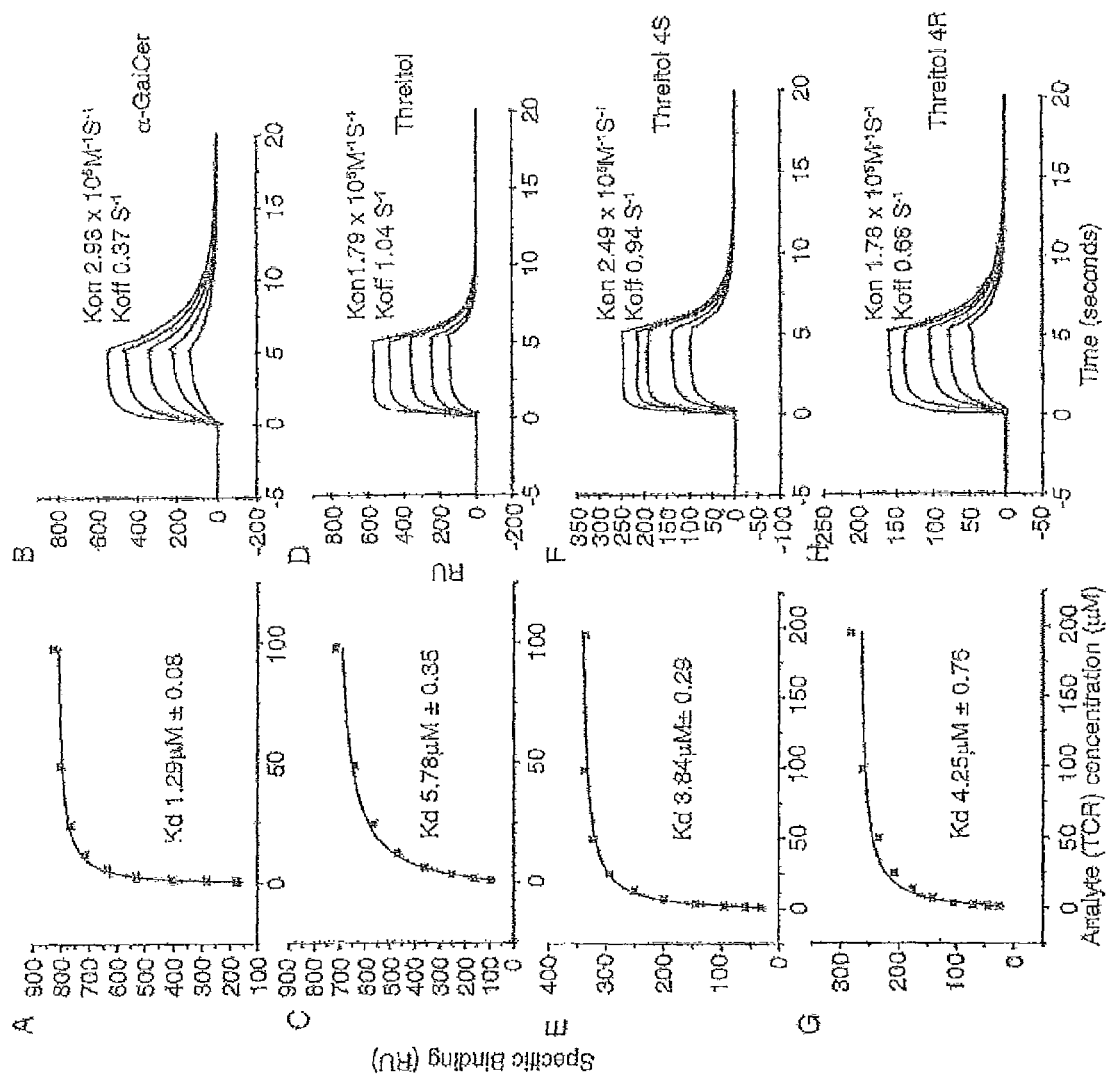

FIG. 3 Surface Plasmon Resonance (Biacore) Measurements of Low Affinity Analogs of α-GalCer The affinities of a soluble NKT cell TCR for human CD1d molecules refolded with different analogs of α-GalCer were measured. Equilibrium binding and kinetic measurements respectively were made for α-GalCer (A and B), threitolceramide (C and D), 4S-threitolceramide (E and F), 4R-threitolceramide (G and H). The $K_d$ values (µM) were calculated from equilibrium binding. The $K_{on}$ values shown were calculated from $K_{off}$ and $K_d$.

Figure 4:
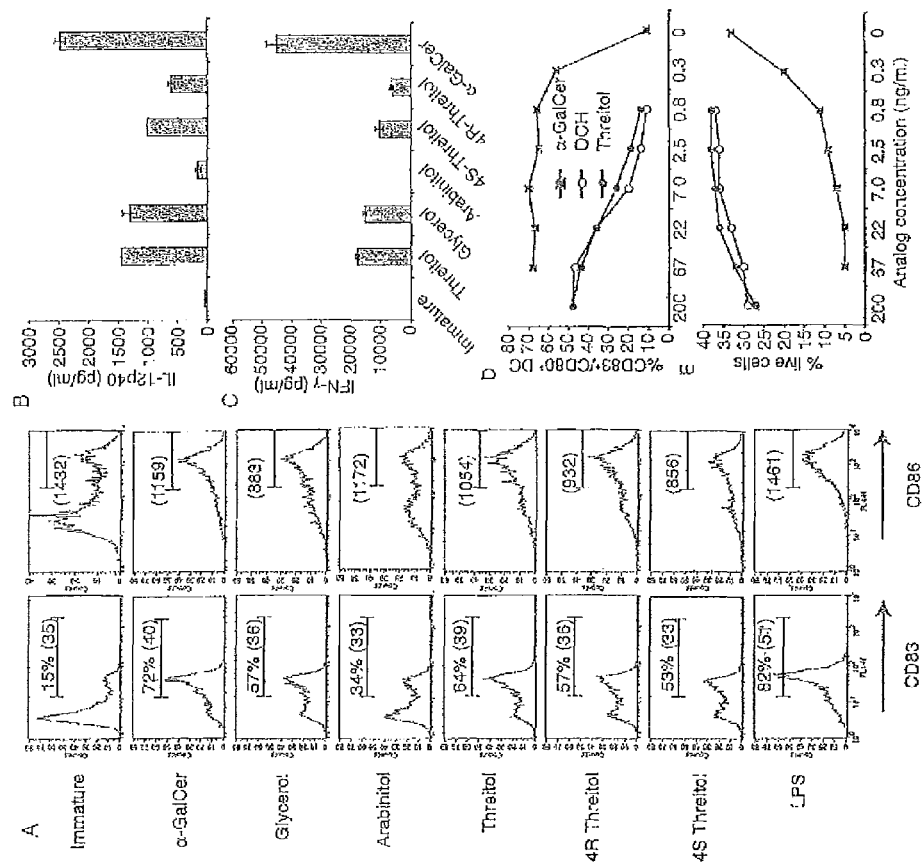

FIG. 4 Human DC are Matured with Analogs of α-GalCer In Vitro when Co-Cultured with iNKT Cells Different analogs of α-GalCer as indicated or LPS were added to co-cultures of human DC and iNKT cells. (A) Maturation of the DC was assessed after 40 h, gating on CD11c positive cells. Histograms indicate the CD83 and CD86 profiles of DC from different treatments; the percentages indicate the percentage of CD83hi mature DC and the numbers in parenthesis, the mean fluorescence intensity of the population contained within the labeled gate. DC and iNKT cells were co-cultured in the presence of different analogs of α-GalCer for 24 hours. Supernatants were analyzed using ELISA for the presence of (B) IL-12p40 released by the DC and (C) IFN-γ from the iNKT cells. All the compounds tested induced weaker but significant cytokine production than α-GalCer, with the exception of arabinitolceramide. (D) Titration of α-GalCer, OCH or threitolceramide on DCs and co-culture with iNKT cells induces DC maturation in vitro. Cells were co-cultured in the presence of the indicated concentration of analog and the percentages of DC with increased CD83/CD80 are shown. (E) Titration of α-GalCer induces significant death of DC in vitro when co-cultured with iNKT cells while low affinity analogs do not. Viability of α-GalCer or analog-pulsed DC was assessed after 40 h co-culture in the presence of iNKT cells by flow cytometry. Cells were stained with propidium iodide and the percentage of live CD11c gated cells remaining in the culture are shown.

Figure 5:
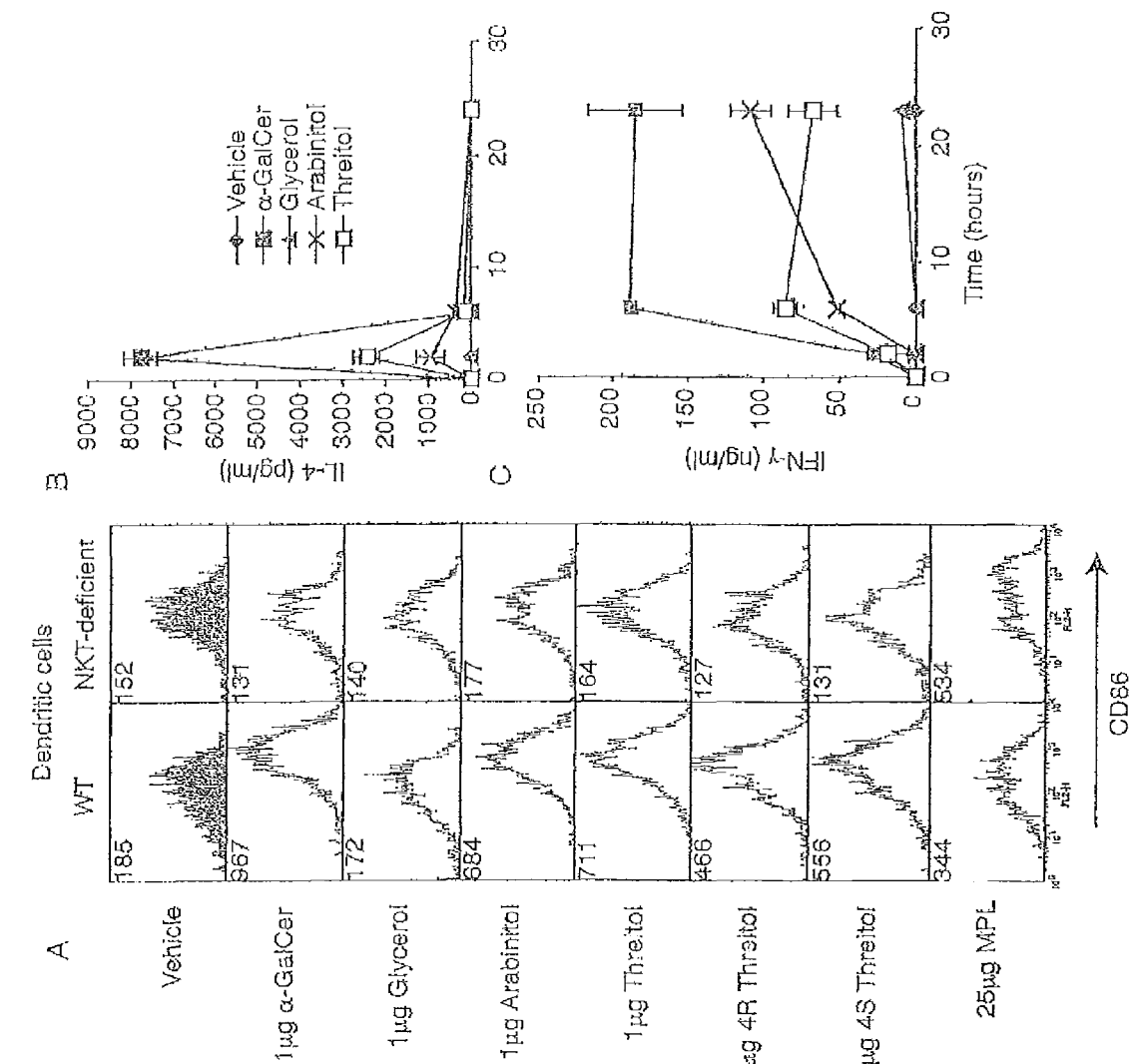

FIG. 5 Non-glycolipid analogs of α-GalCer stimulate activation of iNKT cells and subsequent DC maturation in vivo. C57BL/6 or iNKT$^{-/-}$ mice were injected i.v. with 1 µg of vehicle, α-GalCer, analog or 25 µg MPL. Twenty hours after injection splenocytes were stained with antibodies against CD11c, B220 and CD86 and analyzed by flow cytometry. (A) Maturation was assessed by the upregulation of CD86 at the cell surface, gating on DC (CD11c$^+$). Mean fluorescence intensity for each histogram is indicated. These are representative profiles of two independent experiments. 2, 6 and 18-24 h after injection as described, the mice were bled and the serum tested with ELISA for the presence of (B) IL-4 and (C) IFN-γ released in response to the analog.

Figure 6:
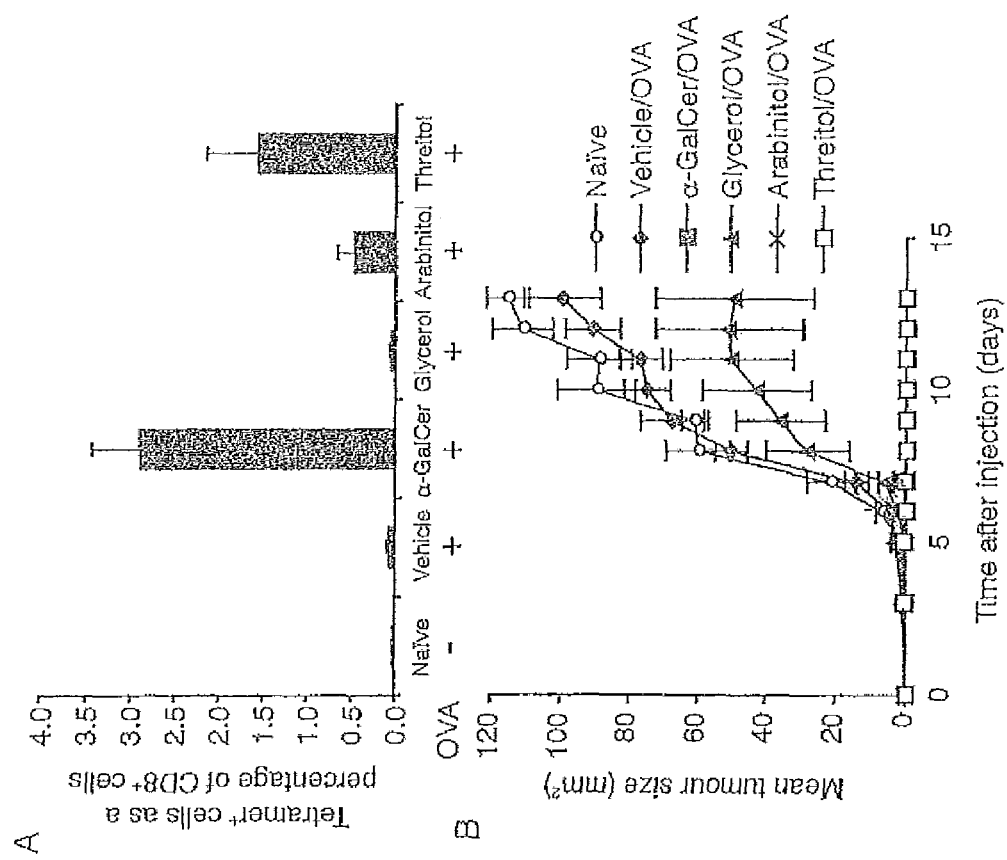

FIG. 6 Non-Glycolipid Antigens as Effective Adjuvants when Co-Administered with a Target Antigen.

(A) C57BL/6 mice were co-injected with 1 µg α-GalCer or analog and 800 µg OVA. 6 days later blood samples taken from the tail vein were stained directly ex vivo with fluorescent SIINFEKL-K$^b$ tetramers and an anti-CD8 antibody and analyzed by flow cytometry. Data are shown as tetramer positive cells as a percentage of CD8$^+$ cells. (B) 7 days after injection, the mice were challenged in a prophylactic setting with 1×10$^6$ E.G7-OVA tumour cells s.c. and the size of the tumour monitored over subsequent days. There was little or no tumour growth in mice injected with α-GalCer, arabinitol or threitolceramide with OVA.

Figure 7:
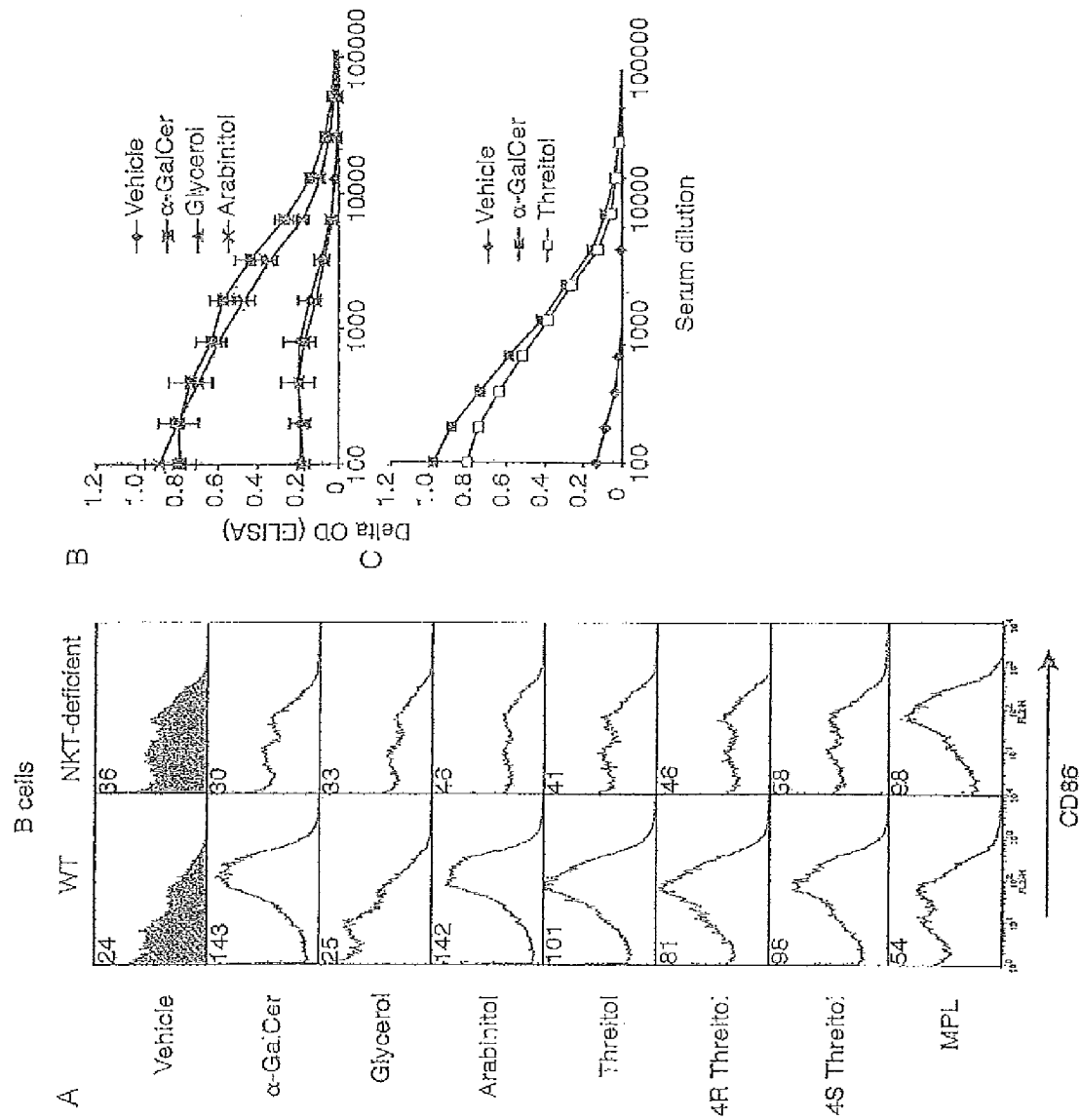

FIG. 7 Non-Glycolipid Analogs of α-GalCer Stimulate B Cell Maturation in the Presence of iNKT Cells In Vivo and Subsequent Antibody Production.

(A) C57BL/6 or iNKT$^{-/-}$ mice were injected i.v. with 1 µg of vehicle, α-GalCer, analog or 25 µg MPL. Twenty hours after injection splenocytes were stained with antibodies against B220 and CD86 and analyzed by flow cytometry. Maturation was assessed by the upregulation of CD86 at the cell surface, gating on B cells (B220$^+$). Mean fluorescence intensity for each histogram is indicated. (B) Simultaneous administration of 1 µg α-GalCer or analogs and 400 µg OVA induces significant OVA-specific IgGs. Mice were bled 11-14 d after administration and the serum tested by ELISA for antibodies. Briefly, ELISA plates were coated with 10 µg/ml OVA and then serial dilutions of sera added and incubated overnight at 4° C. before detecting with an HRP-conjugated sheep anti-mouse IgG.

Figure 8:
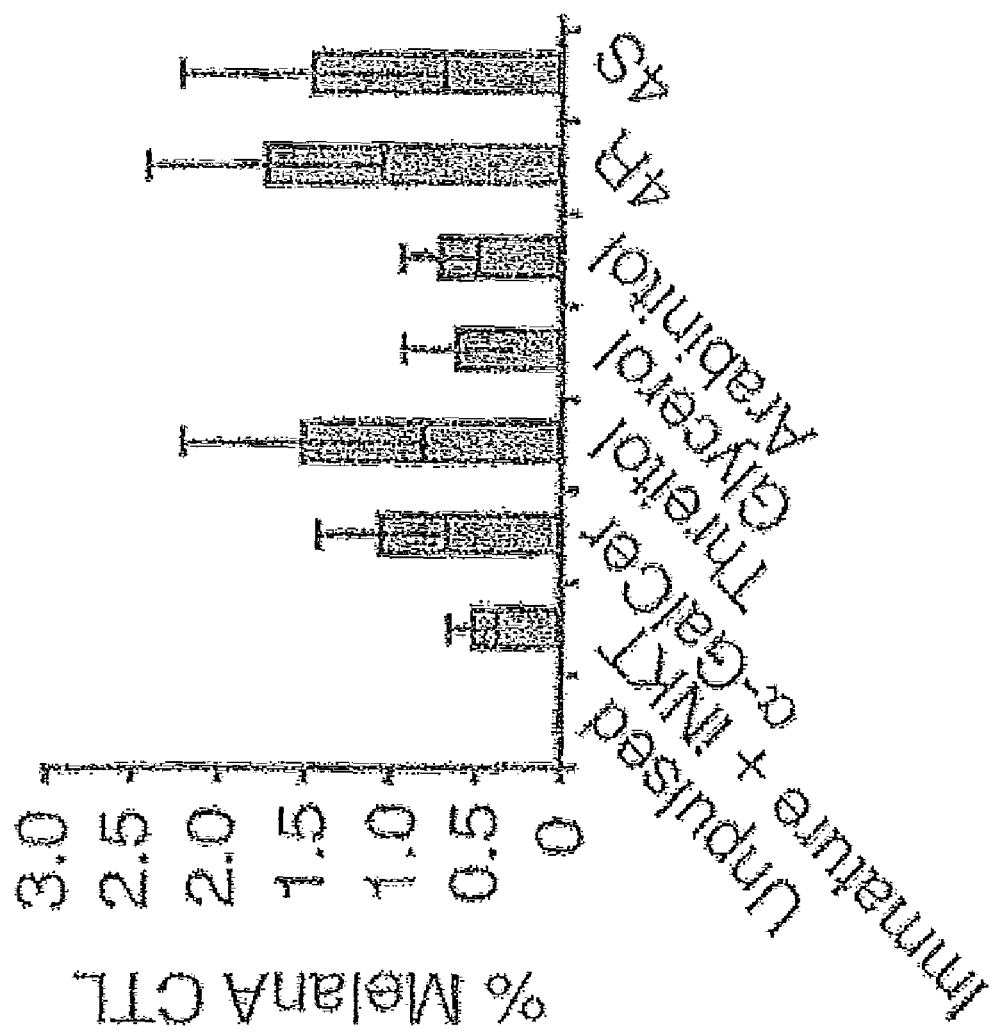

FIG. 8 Expansion of Melan A-specific CD8$^+$ T cells with DC pulsed with threitolceramide is at least as effective as with DC pulsed with α-GalCer in vitro Expansion of Melan A-specific CD8$^+$ T cells with DC pulsed with threitolceramide is at least as effective as with DC pulsed with α-GalCer in vitro. Addition of different α-GalCer analogs and Melan-A$_{26-35}$ peptide to human PBMCs induced DC maturation and subsequent expansion of Melan-A specific CD8$^+$ T cells as assessed by HLA-A2/Melan-A$_{26-35}$ tetramer analysis. Flow cytometry of day 10-15 cultures of PBMCs co-cultured with autologous irradiated APCs, pulsed with Melan-A$_{26-35}$ peptide were stained with the tetramer and anti-CD8$^+$-FITC. Percentages of tetramer cells as a percentage of total CD8$^+$ cells±SE are indicated.

Figure 9:
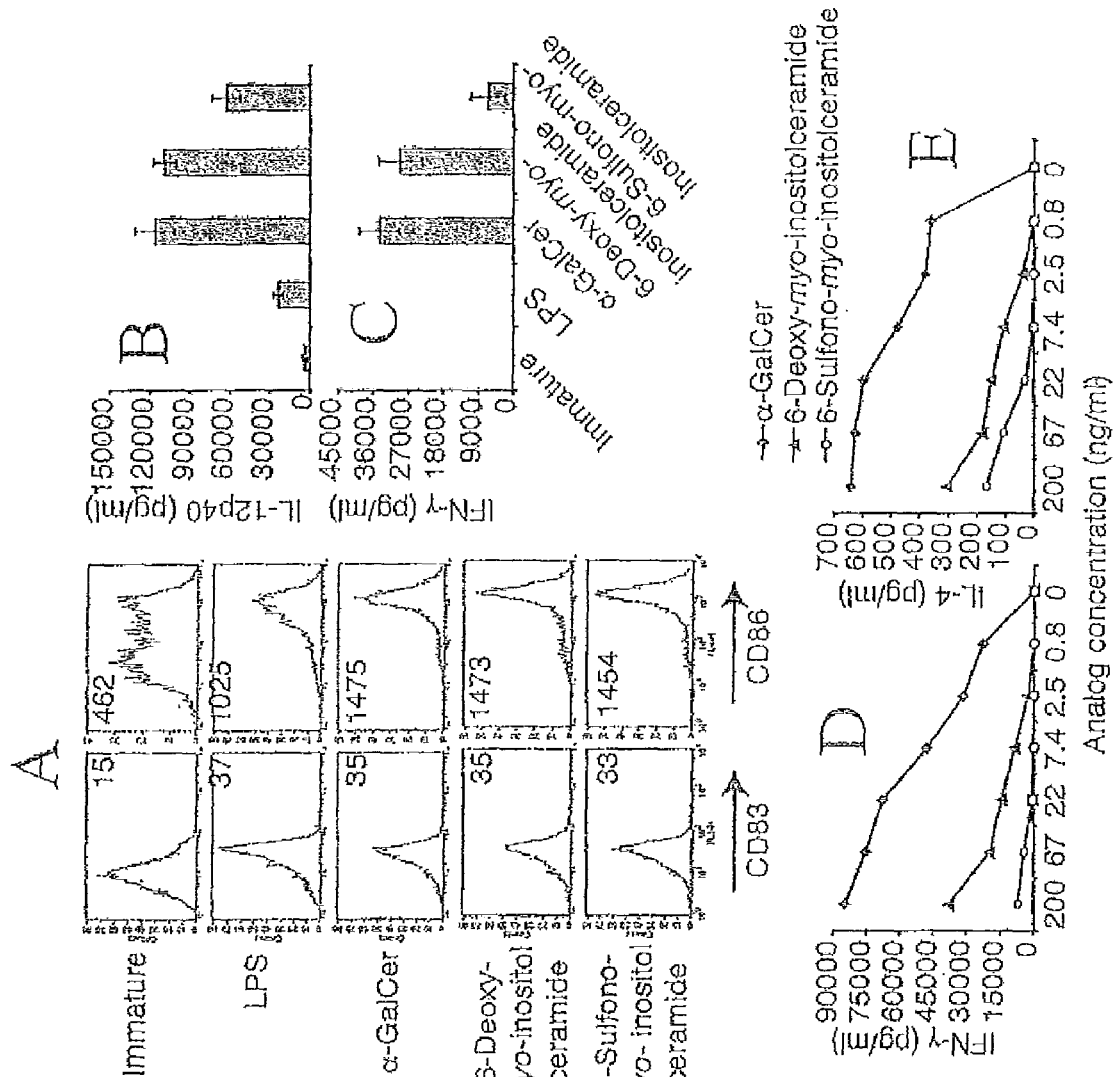

FIG. 9 Inositol-based α-GalCer derivatives are functional in vitro. Human monocyte-derived DC were pulsed with 150 ng of different inositol analogs and co-cultured with iNKT cells for 24 h. The 6-Deoxy- and 6-Sulfono-myo-inositolceramide analogs were only slightly less potent than α-GalCer as assessed by CD83 and CD86 upregulation. Numbers indicate the mean fluorescence intensity of the histogram gated on CD11c+ cells. 6-Deoxy and 6-Sulfono-myo-inositolceramide induce significant (B) IL-12p40 and (C) IFN-γ production by DC and iNKT cells respectively in the supernatants of co-cultured DC and iNKT cells. Supernatants were tested by ELISA and reveal that 6-Deoxy-myo-inositolceramide induces release of similar concentrations of IL-12p40 and IFN-γ to those observed with α-GalCer. Release of (D) IFN-g and (E) IL-4 from iNKT cells after 24 h in culture with C1R-human CD1d cells pulsed with α-GalCer, 6-Deoxy- or 6-Sulfono-myo-inositolceramide. Titrations of the analogs suggest that the human iNKT cell TCR has a lower affinity for these compounds.

SUMMARY OF THE INVENTION

According to the invention there is provided a compound of formula I,

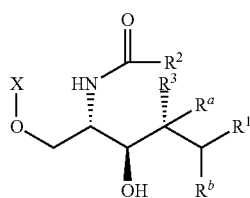

in which
$R^1$ represents a hydrophobic moiety adapted to occupy the C' channel of human CD1d,
$R^2$ represents a hydrophobic moiety adapted to occupy the A' channel of human CD1d, such that $R^1$ fills at least at least 30% of the occupied volume of the C' channel compared to the volume occupied by the terminal $nC_{14}H_{29}$ of the sphingosine chain of α-galactosylceramide when bound to human CD1d and $R^2$ fills at least 30% of the occupied volume of the A' channel compared to the volume occupied by the terminal $nC_{25}H_{51}$ of the acyl chain of α-galactosylceramide when bound to human CD1d
$R^3$ represents hydrogen or OH,
$R^a$ and $R^b$ each represent hydrogen and in addition, when $R^3$ represents hydrogen, $R^a$ and
$R^b$ together may form a single bond,
X represents or $—CHA(CHOH)_nY$ or $—P(=O)(O^-)OCH_2(CHOH)_mY$, in which Y represents $CHB_1B_2$,
n represents an integer from 1 to 4, m represents 0 or 1,
A represents hydrogen,
one of $B_1$ and $B_2$ represents H, OH or phenyl, and the other represents hydrogen or one of $B_1$ and $B_2$ represents hydroxyl and the other represents phenyl, in addition, when n represents 4, then A together with one of $B_1$ and $B_2$ together forms a single bond and the other of $B_1$ and $B_2$ represents H, OH or $OSO_3H$ and pharmaceutically acceptable salts thereof.

According to the invention we also provide a process for the production of compounds of formula I, or a salt thereof, or a pharmaceutically acceptable derivative thereof, which comprises removal of one or more protecting groups from a corresponding compound of formula II,

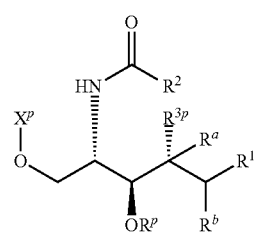

in which $X^p$ represents protected X, $R^p$ is a hydroxyl protecting group, $R^{3p}$ represents a protected hydroxyl group or a hydrogen and $R^1$, $R^2$, $R^a$ and $R^b$ are as defined above.

DETAILED DESCRIPTION OF THE INVENTION

Suitable protecting groups in $X^p$ that may be used to protect X include protecting groups well known to the person skilled in the art of the synthesis of carbohydrates, in particular for protecting isolated hydroxyl groups and adjacent hydroxyl groups. Examples of protecting groups are given in Protecting Groups by P. J. Kocienski (Publisher, Thieme Publishing Group, ISBN 3131356030), the contents of which are hereby incorporated by reference. Further examples are given in Carbohydrate Chemistry by Geert-Ian Boons (Editor, G. J. Boons, Publisher, Springer, ISBN 0751403962), the contents of which are hereby incorporated by reference.

Particular OH protecting groups for $X^p$ include bis-O-isopropylidene, bis-O-cyclohexylidene, tert-butyldiphenylsilyl, allyl and benzyloxy groups. The deprotection reaction may be carried out with trifluoroacetic acid in a methanol:dichloromethane mixture at room temperature over several days. The deprotection may involve Pd/C in the presence of hydrogen gas in methanol or methanol/EtOAc mixture. Where the XP group contains an O—P bond, the triethylamine may also be added to form the ammonium salt.

Suitable protecting groups for $R^p$ and $R^{3p}$ include O-benzyl groups and where $R^p$ and $R^{3p}$ together forming a bis-O-isopropylidene group.

Compounds of formula II, where $OR^p$ and $R^{3p}$ are O-benzyl groups, $R^2$ is a $C_{25}H_{51}$ group, and where $X^p$ is represented by formula,

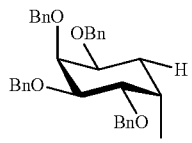

may be prepared by the reduction of compound of the formula IIa, where $X^p$ is

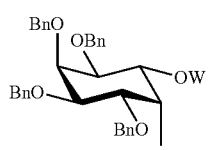

And where $OR^p$ and $R^{3p}$, $R^2$ groups are defined above and where group W is phenoxythiocarbonyl ester group. The reaction may be carried out with tributyltin hydride, AIBN in toluene heated to reflux for 4 hours.

Compounds of formula IIa may be prepared from compound of formula III) where $X^p$ is represented by formula,

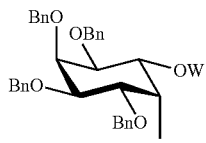

IIb where $OR^p$, $R^{3p}$, $R^2$ are defined above and W is a hydrogen. The reaction may be carried out with phenoxythiocarbonyl chloride, pyridine, DMAP and dichloromethane at room temperature for 30 minutes.

Compounds of formula IIb may be prepared from compounds of formula IIc where $X^p$ is represented by formula,

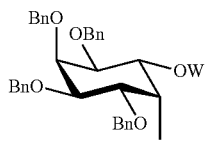

IIc where $OR^p$, $R^{3p}$, $R^2$ are defined above and W is All group. The reaction may be carried out with tris(triphenylphosphine)ruthenium (II) chloride, DBU, 90° C., 30 minutes followed by the addition of 1M HCl/acetone.

Compounds of formula II and IIc may be prepared by reacting compounds of formula III,

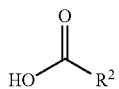

III in which $R^2$ is defined above, with a compound of formula IV,

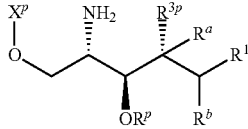

IV where $X^p$, $OR^p$, $R^{3p}$, $R^1$, $R^a$ and $R^b$ are defined above, save that $X^p$ is not

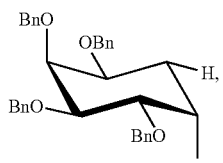

the reaction may be carried out with EDC, HOBt, TEA in DMF at 45° C. for 24 hours.

Compounds of formula III are available commercially or may be made from commercially materials by conventional methods per se.

Compounds of formula IV maybe be prepared by reacting compounds of formula V,

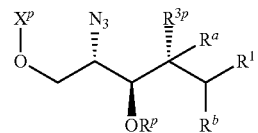

V where $X^p$, $OR^p$, $R^{3p}$, $R^1$, $R^a$ and $R^b$ are defined above. The reaction may be carried out with $LiAlH_4$ in ether at 0° C. warming to room temperature over 1 hour.

Compounds of formula V, where $OR^p$ and $R^{3p}$ are benzyloxy groups and where XP is represented by formula,

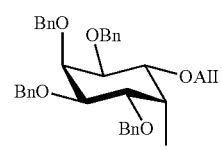

V can be made by the benzyl protection to compounds of formula Va where $OR^p$ and $R^{3p}$ are defined above, and Xp is represented by the group,

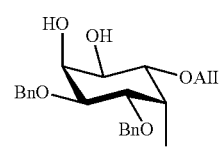

Va

The reaction may be carried out in the presence NaH, BnBr, DMF at room temperature for 5 hours.

Compounds if formula Va can be made by the deprotection of compound of formula Vb where $OR^p$, $R^{3p}$ are define above and $X^p$ is represented by group,

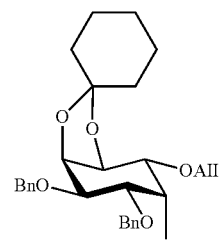

Vb

The reaction may be carried out in the presence hydrochloric acid in a toluene/ethanol mixture, Compounds of formula V and Vb, may be prepared by reacting compounds of formula VI,

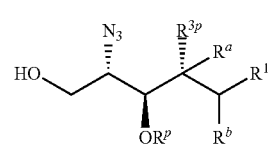

VI where $OR^p$, $R^{3p}$, $R^1$, $R^a$ and $R^b$ are defined above with a compound of formula VII, $$X^p\text{—O-L} \qquad \text{VII}$$

and where group $X^p$ is defined above, save that group $X^P$ is not represented by formula

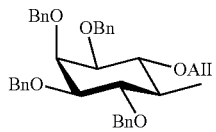

The reaction may be carried out in the presence of sodium hydride in THF, at 0° C. warming to room temperature overnight.

Compounds of formula VI are available commercially or may be made from commercially materials by conventional methods per se.

Compounds of formula VII may be prepared by reacting compounds of formula VIII, $$XP\text{—OH} \qquad \text{VIII}$$

where $X^p$ is above defined above with triflic anhydride in dichloromethane and 2,6-di-tert-butylpyridine.

Compounds of formula VIII are available commercially or may be made from commercially materials by conventional methods per se.

Or alternatively compounds of formula VIII can take the form of compounds of the formula IX:

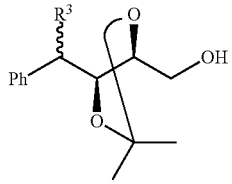

Where $R^3$ is hydrogen. Compounds of formula IX may be prepared by deprotecting compounds of formula X,

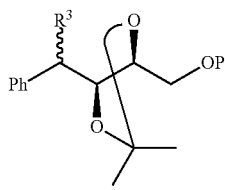

by catalytic hydrogenation, where the group $R^3$ is defined above, and protecting group P is a benzyl group. The reaction may be carried out with 10% Pd/C, $H_2$, in MeOH/EtOAc (2:3) overnight.

Compounds of formula X may be prepared from compounds of formula XI,

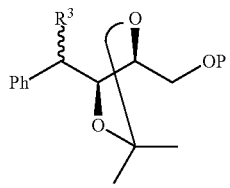

where P is defined above and $R^3$ is a phenoxythiocarbonyl ester. The reaction may be carried out with tributyltin hydride, AIBN in toluene heated to reflux for 4 hours.

Compounds of formula XI may be prepared by preparing from compound of formula XII,

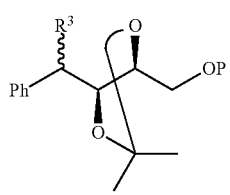

where P is defined above and $R^3$ is a hydroxyl group. The reaction may be carried out with phenoxythiocarbonyl chloride, pyridine, DMAP and dichloromethane at room temperature for 30 minutes.

Compounds of formula XII are available commercially or may be made from commercially materials by conventional methods per se.

Or further alternatively, compounds of formula VIII, can take the form of compounds of the formula XII,

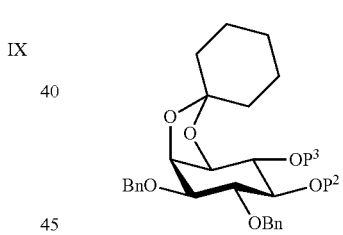

Where $P^2$ is a hydrogen and $P^3$ is either a benzyl group or an A11 group. Compounds of formula XIII may be prepared by the protection of compounds of formula XIV with a benzyl group,

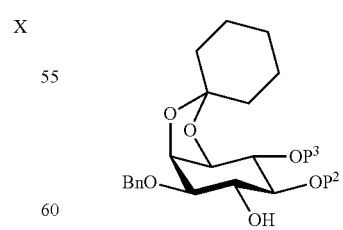

Where $P^2$ and $P^3$ is defined above. The reaction may be carried out with NaH, BnBr in toluene heated to reflux for 10 hrs, followed by separation of isomers.

Compounds of formula XIV are available commercially or may be made from commercially materials by conventional methods per se.

Compounds of formula II where $R^2$ is $C_{25}H_{51}$, $OR^p$ and $R^{3p}$ together form a bis-O-isopropylidene protecting group and $X^p$ is represented by the formula,

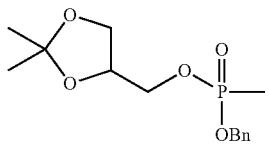

can be prepared by reacting compounds of formula XV,

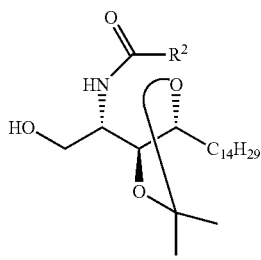

XV where $R^2$ is defined above, with compounds of formula XVI

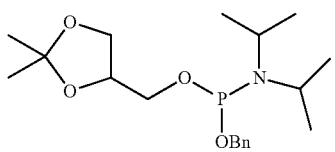

XVI

The reaction may be carried out with tetrazole in dichloromethane at room temperature of 3 hours as an activator, followed by the addition of tert-BuOOH as an oxidant.

Compounds XV and XVI are available commercially or may be made from commercially materials by conventional methods per se.

Compounds of formula III can take the form of compounds of the formula XVII

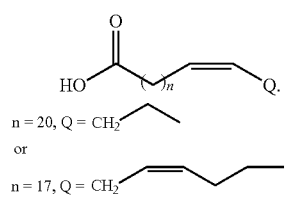

XVII

Compounds of formula XVII may be prepared from compounds of XVIII where n and Q are defined above,

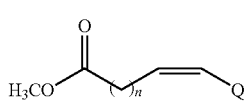

XVIII

The reaction may be carried out in the presence of NaOH (where n=20) and LiOH (where n=17) heat to reflux in methanol for 2 hours followed by the addition of acid.

Compounds of formula XVIII may be prepared from compounds of XIX,

XIX

The reaction may be carried out in the presence of n-butyltriphenylphosphonium bromide (where n=20), and heptenetriphenylphosphonium bromide (where n=17), with sodium bis(trimethylsilyl)amide at −78° C. overnight.

Compounds of formula XIX may be prepared from compounds of XX, where n is defined above

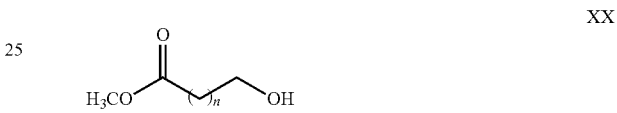

XX

The reaction may be carried out in the presence DMP in dichloromethane at room temperature for 3-4 hours.

Compounds of formula XX may be prepared from compounds of XXI, where n is defined above

XXI

The reaction may be carried out in the presence of p-TSA in methanol for 3-4 hours.

Compounds of formula XXI may be prepared from compounds of XXII, where n is defined above

XXII

The reaction may be carried out in the presence of diazomethane in THF over 4 hours at 0° C. warming to room temperature.

Compounds of formula XXII may be prepared from compounds of XXIII, where m=9 (where n=20), and m=6 (where n=17)

XXIII with a compound of formula XXIV

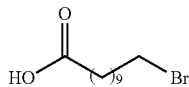

XXIV

The reaction may be carried out in the presence of MeMgCl, Li$_2$CuCl$_4$ in THF at −20° C. to room temperature over 16 hours.

Compounds of formula XXIII may be prepared from compounds of XXV, where m is defined above

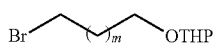

XXV

The reaction may be carried out in the presence of Mg, THF reflux 4 hours.

Compounds of formula XXV may be prepared from compounds of XXVI, where M is defined above

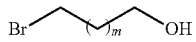

XXVI

The reaction may be carried out in the presence of 3,4-dihydro-2H-pyran, PPTS.

Compounds XXIV and XXVI are available commercially or may be made from commercially materials by conventional methods per se.

Suitable pharmaceutically acceptable salts of the compounds of formula I salts with suitable bases. Examples of such salts include alkali metal, e.g., sodium and potassium, and alkaline earth metal, e.g., calcium and magnesium, salts.

The compound of formula I may be obtained in the form of a salt, conveniently a pharmaceutically acceptable salt.

Where desired, such salts may be converted to the free bases using conventional methods. Pharmaceutically acceptable salts may be prepared by reacting the compound of formula I with an appropriate acid or base in the presence of a suitable solvent.

The compounds of formula I may exhibit tautomerism, they may also contain one or more asymmetric carbon atoms and may therefore exhibit optical and/or diastereoisomerism. Diastereoisomers may be separated using conventional techniques, e.g. chromatography or fractional crystallisation. The various optical isomers may be isolated by separation of a racemic or other mixture of the compounds using conventional, e.g. fractional crystallisation or HPLC, techniques. Alternatively the desired optical isomers may be made by reaction of the appropriate optically active starting materials under conditions which will not cause racemisation. We particularly prefer compounds of formula I in which the stereochemistry of the hydrophilic moiety is analogous to that found in the α-galactose moiety of α-GalCer.

The conditions for a substantially full occupation of both the A' and C' channels, as exhibited by α-GalCer by are described in detail in Koch et al, Nature Immunology, 6(8) 819-826 (2005). In Koch et al., cavities were identified as surfaces accessible to water molecules (radius, 1.4 Å) but no large probes (radius, 6 Å) with the program VOLUMES (R. Esnouf, University of Oxford, Oxford, UK). The open nature of the pockets at the TCR recognition surface required imposition of a self-consistent definition for the outer limit of the pocket, and on this basis the authors calculated the pocket volumes for mouse CD1d, CD1a and CD1b as well as human CD1d. Although this resulted in some differences in absolute values from those reported before, the same relative trends were noted. Shape complementarity analysis was made using the program SC (http://www.ccp4.ac.uk/ccp4i_main.html). We particularly prefer compounds of formula that bind to human CD1d with a good shape complementarity, that is with a $S_c$ greater than 0.50, more preferably greater than 0.55, particularly greater than 0.60.

The 26 carbon acyl chain and the 18 carbon sphingosine chain of α GalCer fit into the A' and C' pockets, respectively, with good shape complementarity ($S_c$ 0.61). The total volume of these cavities (1,400 Å$^3$) of these cavities in, the human CD binding groove is essentially filled by the hydrocarbon chains. The acyl chain fits into the A' pocket by adopting a counterclockwise circular curve as viewed from above the binding groove, filling the pocket. The sphingosine chain adopts a straighter conformation to fit into the C' pocket and terminates at the end of the binding groove. Thus it is likely that α-GalCer has the maximum lipid chain lengths that are able to fit into the antigen-binding groove of human CD1d. Accordingly we prefer the length of R$^2$ (the acyl chain) not to exceed 25 carbon-carbon single bonds in length and R$^1$ (the sphingosine chain) not to exceed 13 carbon-carbon single bonds in length. From binding studies reported in the literature, it is known that carbon-carbon double bonds may be substituted for several of the carbon-carbon single bonds, provided that the hydrophobic moieties are still able to occupy the conformations necessary for binding with their respective channels. Some studies have shown for example that the channels are able to accept relatively bulky hydrophobic residues, such as phenyl.

We prefer compounds of formula I in which R$^1$ fills at least 35%, more preferably at least 60%, yet more preferably at least 80% and especially at least 90% of the occupied volume of the C' channel as hereinbefore defined.

We prefer compounds of formula I in which R$^2$ fills at least 40%, more preferably at least 50%, yet more preferably at least 60%, particularly at least 70% and especially at least 80% of the occupied volume of the A' channel as defined hereinbefore.

From x-ray diffraction studies and modeling experiments, it appears that when the R$^2$ group is shorter than the preferred maximum length, the remaining space can be occupied by "spacer" molecules which occur naturally in the body and are sufficiently available to occupy vacant spaces in the CD1d molecule. Such spacer molecules are lipids and the like. Because of this compounds of formula I in which R$^2$ a great deal smaller than is needed for maximum occupation of the A' channel will still bind well to the CD1d molecule.

Preferably, R$^2$ is at least one carbon unit (ie methyl) in length, more preferably at least 5 carbon units in length and particularly at least 8 carbon units in length. We prefer compounds of formula 1 in which R$^2$ represents a saturated or unsaturated linear hydrocarbon chain containing from 1 to 25, more preferably 5 to 25 and particularly 8 to 25 carbon atoms.

It appears that the binding of the sphingosine chain is more dependent on the Proportion of occupation of the C' channel, than the binding of the acyl chain to the A' channel, in that occupation of this channel by spacer molecules has not, as far as the inventors are aware, been observed to date. As such, R$^1$ is preferably at least 5 carbon-carbon single bonds in length, more preferably at least 11 carbon-carbon single bonds in length and especially 12 or 13 carbon-carbon single bonds in length.

We prefer compounds of formula I, wherein either or both of $R^1$ or $R^2$ contains one or more double bonds. We particularly prefer those compounds in wherein either or both of $R^1$ or $R^2$ contains one, two or three double bonds. We prefer those compounds in which $R^2$ contains double bonds.

We prefer those compounds wherein the double bonds are cis (Z).

We prefer those compounds in which X represents CHA(CHOH)$_n$CHB$_1$B$_2$.

We prefer compounds of formula I in which X represents CH$_2$(CHOH)$_n$CHB$_1$B$_2$.

We prefer compounds of formula I in which n represents 1, 2 or 3, especially 2.

We prefer compounds of formula I and in which n represents 2 which is in the threo, as opposed to erytho configuration.

We prefer compounds of formula I in which $R^3$ represents hydrogen.

We prefer compounds of formula I in which $R^a$ and $R^b$ both represent hydrogen.

We prefer compounds of formula I in which one of $B_1$ and $B_2$ represents hydrogen and the other represents hydroxyl.

We prefer compounds of formula I in which m represents 1

We prefer compounds of formula I in which Y represents CH$_2$OH, CH$_2$PH or C(OH)(Ph). We especially prefer compounds where Y represents CH$_2$OH.

We also prefer compounds of formula I in which n represents 4, and where A and $B^1$ and $B^2$ together form a single bond and the other of $B^1$ and $B^2$ is OH or OSO$_3$H.

The ability of the compounds of formula I to modulate antigen specific immune responses enables the compounds to be useful in cancer therapy, preventive and therapeutic vaccines, allergies and autoimmune diseases.

According to the invention there is also provided a compound of formula I for use as a medicament.

According to the invention there is also provided a method of protecting a mammalian subject against, or treating, a virus, microbial infection, parasite, an autoimmune disease, cancer, allergy or asthma which comprises administering to the subject a pharmaceutically effective amount of a compound according to the invention which has pharmaceutical activity against, or in treating, such a virus, microbial infection, parasite, an autoimmune disease, cancer, allergy or asthma.

According to the invention we also provide the use of compounds of formula I and salts thereof in the preparation of a medicament for the treatment or prophylaxis of a virus, microbial infection, parasite, an autoimmune disease, cancer, allergy or asthma.

In particular, the compounds of formula I may be used in the treatment or prophylaxis of the following diseases:

Cancers: For example Basal Cell Carcinoma, Breast Cancer

Leukemia, Burkitt's Lymphoma, Colon Cancer, Esophageal Cancer, Bladder Cancer, Gastric Cancer, Head and Neck Cancer, Hepatocellular Cancer, Hodgkin's Lymphoma, Hairy Cell Leukemia Wilms' Tumor, Thyroid Cancer, Thymoma and Thymic Carcinoma, Testicular Cancer, T-Cell Lymphoma, Prostate Cancer, Non-Small Cell Lung Cancer, Liver Cancer, Renal Cell Cancer, and Melanoma.

Viral infections that may be mentioned include:

Viral Hepatitis for example HBV, HCV;

Herpes virus infection for example Herpes simplex virus.

Other skin tropic viruses like human papiloma virus.

Lung tropic viruses like influenza virus or respiratory syncytial virus.

Chronic or acute viral infections with HIV, EBV or CMV or combinations of viral infections or viral and bacterial infections.

Bacterial infections of the lung with for example *Haemophilus influenzae* or mycobacteria for example *Mycobacterium tuberculosis* and bacterial infections of the gut with for example *helicobacter pylori* or the skin like *Staphylococcus aureus*.

Asthma, allergen induced asthma, contact dermatitis, psoriasis, Crohn's disease.

More especially diseases that may be treated with compounds of formula I are virus, microbial infection, parasite, cancer.

The compounds of formula I may be used alone or in combination with other therapeutic agents. Combinations with other therapeutic agents include:

Immune modulators like anti CD40/CD40L antibody, anti-CTLA-4 blocking antibody or soluble LAG3 based immune modulators, Toll-like receptor agonists like MPL, CpG, Single-Stranded RNA, nucleotides, nucleotide analogues like CL087 or loxoribine, polyinosine-polycytidylic acid, flagellin, resiquimod or immiquimod, gardiquimod among others. NOD Ligands like Muramyl dipeptide, Murabutide or Peptidoglycan, Muramyldipeptide among others, Anti-virals like oseltamivir phosphate, antifungals like Amphotericin B and antibiotics. Antiviral antibodies like palivizumab.

Other useful combinations include other cancer immune therapeutics like herceptin, alemtuzumab, gemtuzumab, rituximab, ibritumomab tiuxetan and other monoclonal antibody based cancer treatments. Chemotherapy agents, kinase inhibitors like Imatinib or Erlotinib or cytotoxic agents like cyclophosphamide. Anti-asthmatics and antihistamines and anti-inflammatory drugs could also be used in combination. Other potential combinations include vaccine adjuvants like virus-like particles (VIPs), liposomes, and artificial antigen presenting cells. It can be used as an additive in live cell therapy for example DC-based immunotherapy.

Other potential combinations include, cytokine or chemokine blocking antibodies like infliximab, Adalimumab and basiliximab.

We also provide a pharmaceutical composition comprising a compound according to the invention in admixture with a pharmaceutically acceptable excipient, carrier or adjuvant. Such formulations are generally well known to the person skilled in the art and may be analogous to those described in EP 0 609 437B, EP-A-1 437 358 and WO 2004/028475, the contents of which are herein incorporated by reference.

Compositions in a form suitable for topical administration to the lung include aerosols, e.g. pressurised or non-pressurised powder compositions;

compositions in a form suitable for oesophageal administration include tablets, capsules and dragees;

compositions in a form suitable for administration to the skin include creams, e.g. oil-in-water emulsions or water-in-oil emulsions;

compositions in a form suitable for administration intravenously include injections and infusions; and compositions in a form suitable for administration to the eye include drops and ointments.

According to the invention there is also provided a pharmaceutical composition comprising, preferably less than 80% and more preferably less than 50% by weight of a compound of formula I. or a pharmaceutically acceptable derivative thereof, in admixture with a pharmaceutically acceptable diluent or carrier.

Examples of such diluents and carriers are:

for tablets and dragees—lactose, starch, talc, stearic acid;

for capsules—tartaric acid or lactose; and for injectable solutions—water, alcohols, glycerin, vegetable oils.

When the compound of formula I is to be administered to the lung it may be inhaled as a powder which may be pressurised or non-pressurised. Pressurised powder compositions of the compounds of formula may contain a liquified gas propellant or a compressed gas. In non-pressurised powder compositions the active ingredient in finely divided form may be used in admixture with a larger-sized pharmaceutically acceptable carrier comprising particles of up to, for example, 100 µm in diameter.

Suitable inert carriers include, e.g. crystalline lactose.

For the above mentioned uses the doses administered will, of course, vary with compound employed, the mode of administration and the treatment desired. However, in general, satisfactory results are obtained when the compound of formula I is administered at a daily dosage of from about 1 µg to about 20 mg per kg of animal body weight, preferably given in divided doses 1 to 4 times a day or in sustained release form.

For man the total daily dose is in the range of from 70 µg to 1,400 mg and unit dosage forms suitable for administration comprise from 20 mg to 1,400 mg of the compound admixed with a solid or liquid pharmaceutical diluent or carrier.

The compounds of formula I have the advantage that they are less toxic, more efficacious, are longer acting, have a broader range of activity, are more potent, produce fewer side effects, are more easily absorbed or have other useful pharmacological properties, than compounds of similar structure, for example GalCer.

Several of the analogs of the current invention exhibited excellent immunomodulatory activity as evidenced by the fact that (a) analogs acted as immunostimulants or adjuvants when injected into mice together with antigens as evidenced by the generation of antigen-specific IgG responses, or antigen-specific cytotoxic CD8+ T lymphocytes responses, or as evidenced by the protection of mice from death when analogs were injected as monotherapy into animals in both protective and established models of tumour growth.

Additionally, analogs acted as immunostimulants when injected as monotherapy into mice, as evidenced by the induction of IL-12 responses, or as evidenced by the protection of mice from weight loss and/or death in established models of influenza infection.

Additionally, analogs acted as immunostimulants or adjuvants when added to samples of human peripheral blood lymphocytes ('PBLs') as evidenced by the induction of markers of dendritic cell maturation in such PBL samples, or when added to samples of human PBLs which were pulsed by the addition of the known immunogenic MelanA26-35 peptide, ELAGIGILTV (SEQ ID NO: 1), as evidenced by the induction of CD8+ T cells which were specific for the target MelanA26-35 peptide.

Importantly, many αGal-Cer analogs of the prior art induce such strong NKT cytokine responses in vivo that NKT cells are driven into an unresponsive state and become refractory to further immunostimulation, see, Parekh et al., *J. Clin. Invest.*, 115:2572-2583 (2005).

In contrast to compounds of the prior art, certain analogs of the current invention are highly effective inducers of human dendritic cell maturation whilst producing only limited NKT cytokine responses in human NKT cells compared with αGal-Cer. Such separation of dendritic cell stimulation and consequent maturation in the absence of NKT cytokine secretion is a unique aspect of the current invention.

This unique and novel aspect is anticipated to allow repeated stimulation of dendritic cells without exhaustion or depletion of the NKT cell population following administration of compounds of the current invention.

In the examples which follow, new molecules are described, together with methods for their synthesis. These examples are followed by a showing of the immunomodulatory properties of these molecules.

The stimulation referred to supra can be seen to provide protection from conditions in which it is desirable for the immune system to respond effectively such as infectious disease or cancer.

Additionally, compounds of the invention can be used in combination with TLR ligands such as poly I:C (TLR3), MPL (TLR4), imiquimod (TLR7), 8848 (TLR8) or CpG (TLR9) to produce an enhanced immune stimulation and resulting protection from conditions in which it is desirable for the immune system to respond effectively such as infectious disease or cancer.

Compounds of the invention can also be used as immunostimulants or adjuvants in combined use with antigen materials such as, without limitation, proteins, peptides, or nucleic acids and so forth in order to produce a protective immune responses, such as a B-cell and IgG antibody response to the administered antigen.

Compounds of the invention can also be used as immunostimulants or adjuvants in combined use with antigen materials such as, without limitation, proteins, peptides, or nucleic acids and so forth in order to produce a protective immune responses, such as a T-cell or CTL response to the administered antigen.

Such antigen materials could be any materials suitable for prevention or therapy of that particular disease. Specifically, with regards to cancer, examples of tumor associated peptide and protein antigens that can be administered to induce or enhance an immune response are derived from tumor associated genes and encoded proteins including MAGE-A1, MAGE-A2, MAGE-A3, MAGE-A4, MAGE-A5, MAGE-AG, MAGE-A7, MAGE-A8, MAGE-A9, MAGE-A10, MAGE-A11, MAGE-A12, MAGE-A13, GAGE-1, GAGE-2, GAGE-3, GAGE-4, GAGE-5, GAGE-6, GAGE-7, GAGE-8, BADE-1, RAGE-1, LB33/MUM-1, PRAMS, NAG, MAGE-1×2 (MAGE-B2), MAGE-Xp3 (MAGE-B3), MAGE-Xp4 (MAGE-B4), tyrosinase, brain glycogen phosphorylase, Melan-A, MAGE-C1, MAGE-C2, NY-ESO-1, LAGE-1, SSX-1, SSX-2(HOM-MEL-40), SSX-1, SSX-4, SSX-5, SCP-1 and CT-7. For example, antigenic peptides characteristic of tumors include those listed in published PCT application WO00/20581 (PCT/US99/21230).

The compounds of the invention are efficacious both in vitro and in vivo, and in both mice and humans as has been shown. Hence, one aspect of the invention relates to stimulating an immune response in a subject, by administering one or more of the compounds of the invention with or without an antigenic molecule, in an amount sufficient to stimulate a favorable immunologic response in such subject.

It will be clear as well that compositions and or kits, comprising one or more of the derivatives of the invention, together with one or more immunogenic proteins or peptides (as compositions), or as separate portions of derivative and protein or peptide, (as kits), are another feature of the invention.

Other facets of the invention will be clear to the skilled artisan and need not be reiterated here.

There are two major parameters that determine the activation of NKT cells by its ligand CD1d, 1) The affinity of the iNKT TCR to CD1d (largely determined by the nature of the CD1d bound ligand).

2) The stability of the CD1d complex (determined by the nature of the CD1d bound ligand).

Combined structural, kinetic and functional analyses of soluble TCR binding to CD1d-lipid complexes and activation of invariant NKT (iNKT) cells have provided important insights into the identification of optimal iNKT cell agonists for clinical use. The aim of these studies was to identify iNKT cell agonists that, unlike α-GalactosylCeramide (α-GalCer), were capable of fulfilling 3 criteria: a) capable of inducing iNKT cell activation, without over-stimulating iNKT cells to minimise iNKT cell dependent Dendritic Cells (DC) lysis and cytokine storm; b) capable of ensuring DC maturation c) capable of ensuring optimal antigen specific T cell priming.

The knowledge derived from the structure of CD1d-α-GalCer specific TCRs (Gadola, Koch et al, J Exp Med, 2006, 203; 699-710) and from the structure of empty and α-GalCer loaded human CD1d molecules (Koch, Strange et al, Nat Immunol, 2005, 6; 819-26) prompted us to carry out a series of kinetic and functional experiments to assess the role of the polar head and the length and saturation of α-GalCer alkyl chains in controlling the rate of dissociation of lipids bound to CD1d molecules and the affinity of binding of lipid specific TCR.

To address these questions, we engineered two reagents: i) a soluble TCR from an iNKT cell clone and ii) an antibody specific for CD1d-α-GalCer complex. Using these two reagents we carried out combined kinetic and functional studies to compare affinity of iNKT TCR binding to human CD1d molecules loaded with either α-GalCer or its analogues with either truncated acyl and sphingosine chains or modified polar head.

Role of Lipid Length in Controlling Stability of CD1d/Lipid Complexes iNKT and in Modulating TCR Binding Affinity to CD1d-Lipid Complex.

We refolded in vitro reduced and biotinylated CD1d monomers and loaded them with a range of α-GalCer analogues with truncated acyl or sphingosine chains. We then analyzed independently the rate of dissociation of the analogues from CD1d molecules and the affinity of binding to a soluble iNKT TCR.

We tested α-GalCer and (2S,3S,4R)-1-O-(α-$_D$-galactopyranosyl)-N-tetracosanoyl-2-amino-1,3,4-nonanetriol (hereafter referred as to OCH), which has a shorter sphingosine chain than α-GalCer and had previously been shown to bind to mouse CD molecules with a shorter half-life, resulting in a weaker activation of mouse iNKT cells (Miyamoto, Miyake et al, Nature, 2001, 413; 531-4, Oki, Chiba et al, 3 Clin Invest, 2004, 113; 1631-40).

In order to measure the rate of dissociation from CD1d molecules, we generated by phage display library a Fab antibody specific for CD1d molecules loaded with α-GalCer (hereafter referred as to 9B Fab), Initial Biacore measurements and FACS staining of lipid pulsed C1R-CD1d cells demonstrated that the 9B Fab recognised specifically human CD1d molecules loaded with all the tested compounds while it failed to stain unpulsed C1R-CD1d cells (data not shown). Using the 9B Fab we looked at the rate of dissociation of all the tested compounds from soluble human CD1d molecules using surface plasmon resonance. Biotinylated CD1d-lipid complexes were immobilized to streptavidin-coated chips and the level of binding of the 9B Fab was measured over time. The loss of binding of the antibody over time was used to determine the rate of lipid dissociation from CD1d molecules.

Figure 1:
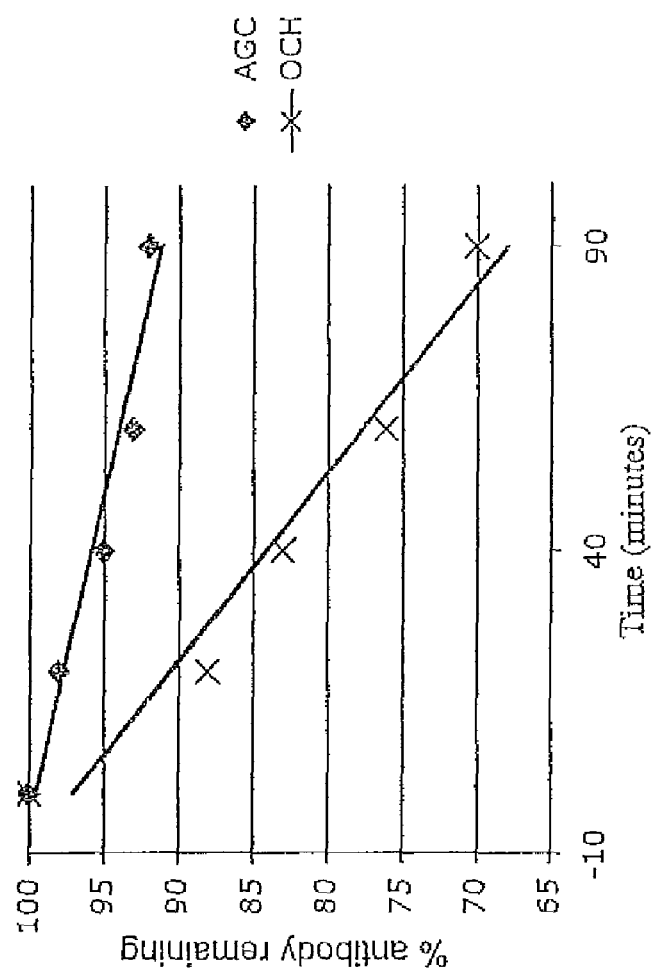
FIG. 1. Comparison of dissociation rate of OCH and α-GalCer. Dissociation of ligand from hCD1d. The indicated hCD1d (α-Gal Cer or OCH) complex was loaded onto a Surface Plasmon resonance (Biacore) sensor surface at t=0 and the amount of hCD1d remaining at the indicated time point measured using the Fab 9B.

Results: OCH had a rate of dissociation 3.9 fold faster than α-GalCer, respectively (FIG. 1). These results were consistent with previously published data, demonstrating that the stability of glycolipids bound to CD1d molecules depends on the length of the alkyl chains (Old, Chiba et al, J Clin Invest, 2004, 113; 1631-40).

Figure 2:
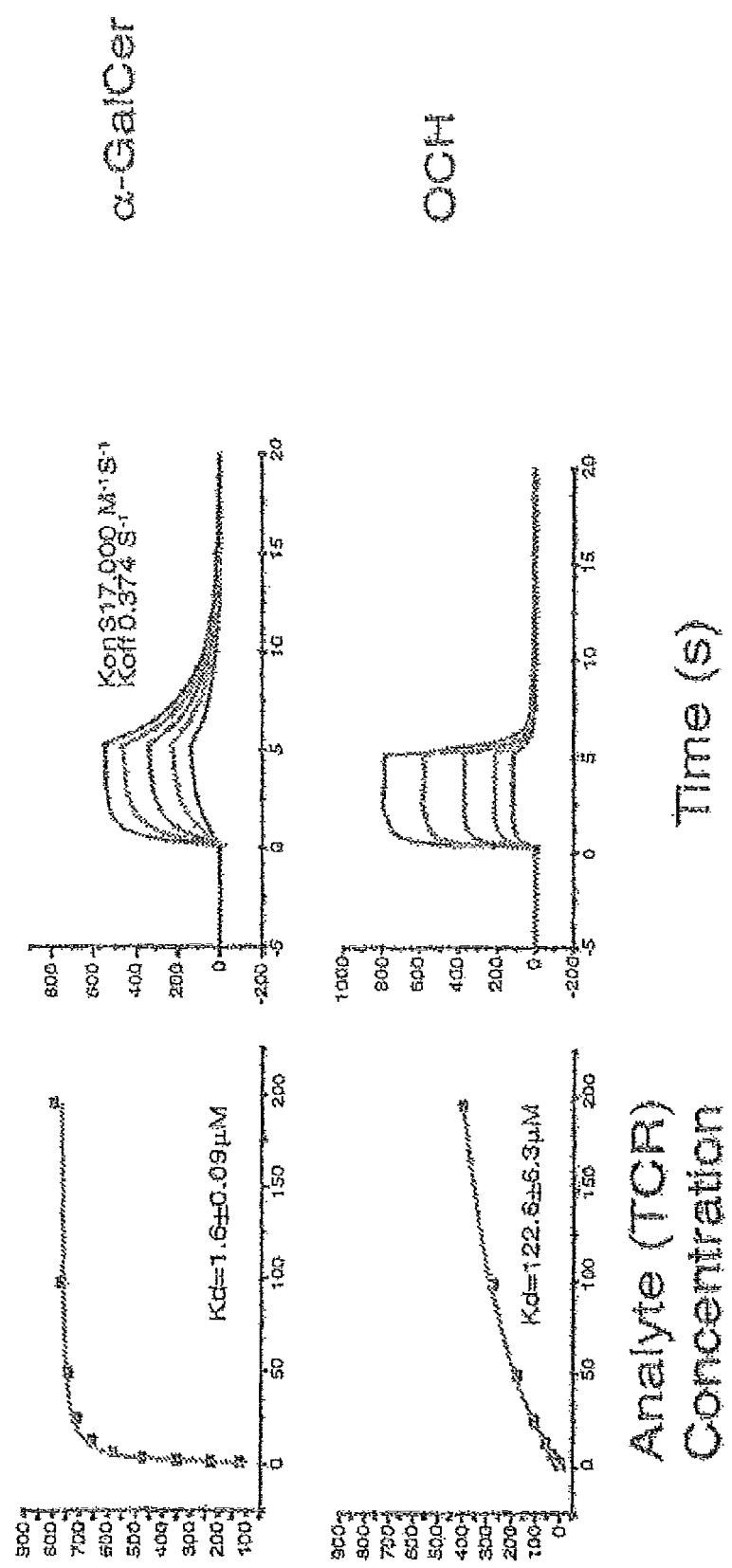
FIG. 2 Comparison of TCR Binding Affinity for OCH and α-GalCer.

We then assessed whether the length of the acyl and sphingosine chains could affect the affinity of iNKT TCR binding to glycolipid-CD1d complex. We refolded Vα24 and Vβ11 chains of the iNKT TCR as previously described (Gadola, Koch et al, J Exp Med, 2006, 203; 699-710) and used the purified and refolded iNKT TCR in surface plasmon resonance studies against immobilized biotinylated CD1d monomers loaded with either α-GalCer or OCH. The results of these experiments demonstrated that an increase in the sphingosine chain length correlated with an increase in TCR binding affinity, suggesting that a reduction of the lipid chain length negatively affects TCR binding affinity to lipid-CD Id complexes (FIG. 2).

Conclusions: The crystal structure of human CD1d-GalCer demonstrated that α-GalCer exploits fully the binding capacity of CD1d. Using surface plasmon resonance, we found that: i) shortening of either alkyl chains significantly reduced the stability of CD1d/lipid complexes (FIG. 1 and data not shown); ii) shortening of the sphingosine chain of α-GalCer reduces the iNKT cell TCR affinity by 1.00 fold (FIG. 2), resulting in changes to the iNKT cell immunological synapse, polarization of iNKT cell cytotoxic granules and iNKT cell activation (data not shown). In contrast, variations in either the length or saturation of the acyl chain do not alter iNKT cell TCR affinity (data not shown). Analysis of previously reported structures of empty and loaded human CD1d molecules suggests that incomplete occupation of the binding groove by a shortened sphingosine chain could result in conformational differences at the TCR recognition surface. This indirect effect provides a general mechanism by which the length of the lipid chain occupying the CD1d C' channel plays a role in controlling the affinity of lipid specific CD restricted T cells.

The observed modulation of TCR binding affinity of the OCH/CD1d complex is therefore achieved at the cost of greater instability of the CD1d lipid complex, caused by the shortened sphingosine chain. Since NKT cell agonists with shorter sphingosine chains will have a shorter lifespan in vivo, we aimed to define a new family of compounds capable of binding with high affinity to CD1d. Such new class of molecules would provide us with an opportunity to fine-tune the range of binding affinity between the NKT TCR and the CD1d/lipid complexes.

Modification of the Polar Head.

i. Glycerol Ceramide Derivatives

Lower Affinity of the Invariant TCR for α-GalCer Analogs.

To characterize the affinity of analogs of α-GalCer, biotinylated hCD1d monomers were generated using previously described protocols (Karadimitris, Gadola et al, Proc Natl Acad Sci USA, 2001, 98; 3294-8) bound to the different analogs. Surface plasmon resonance (Biacore) analysis was performed using a soluble disulphide-linked human invariant Vα24$^+$/Vβ11$^+$ TCR (Gadola, Koch et al, Exp Med, 2006, 203; 699-710) to measure the equilibrium dissociation constants ($K_d$) of binding of the TCR to different monomers (FIG. 3).

The $K_d$ of the TCR binding to the α-GalCer containing monomer was 1.29M, while that of threitolceramide was lower affinity at 5.74 µM. Binding of the TCR to the 4S and 4R threitolceramide monomers was of slightly higher than to the unmodified threitolceramide at 3.84 µM and 4.25 µM respectively.

Differences in the kinetic measurement of the rate of dissociation ($K_{off}$) between the TCR and the different monomers were of similar magnitude between the analogs as in the equilibrium studies (FIG. 3) with 0.37 $s^{-1}$ for α-GalCer and 0.506 and 0.650 $s^{-1}$ for the 4R and 4S threitolceramide derivatives respectively. The quickest $K_{off}$ of those tested was with the unmodified threitolceramide analog at 1.04 $s^{-1}$ indicative of a lower affinity interaction. It is tempting to speculate that the difference in affinity observed between the 4S and 4R variants was due to increased stability of the phenyl-threitol head group interacting with the TCR. These data suggest that the structure previously generated can be useful in the rational design of CD1d-binding analogs that may have different properties to α-GalCer.

In an effort to identify the minimal residues required to stimulate iNKT cells, we decided to generate a family of compounds retaining high affinity to CD1d molecules (i.e. with maximum length of both alkyl chains), and containing either a 3-carbon (i.e. glycerol-mimic head group), a 4-carbon (i.e. threitol-mimic head group, hereafter referred as to threitol-ceramide) or a 5-carbon (i.e. arabinitol mimic head group).

Immature human DC were cultured in the presence of a human iNKT cell clone with or without analogs or vehicle at different concentrations. After 24 hours, DC were assessed by flow cytometry for the upregulation of different maturation markers. α-GalCer induced significant upregulation of all the markers examined (CD83, CD86 and CD38) (FIG. 4 and unpublished data). In each case the degree of maturation observed with an analog was reduced compared with α-GalCer. Threitolceramide was more potent than glycerolceramide and arabinitolceramide, while modifications in the phenyl-variants 4R-threitolceramide and 4S-threitolceramide do not seem to have affected their function. Interestingly arabinitolceramide appeared to be only weakly functional in this system, which may be significant and indicate the degree of interaction necessary to stimulate through the human invariant TCR.

Release of IL-12p40 (and bioactive p75) by DC is a marker of activation and is thought to play an important role in regulating the profile of the immune response generated in response to those DC (Trinchieri et al, Nat Rev Immunol, 2003, 3; 133-46). IL-12p40 was measured from the supernatants of the mixed cultures and the concentration of 11-12p40 released (FIG. 4B) reflected the maturation responses previously described (FIG. 4A). α-GalCer induced significant levels of IL-12p40, while threitolceramide and glycerolceramide induced approximately 50% of the level seen in the presence of α-GalCer. Both 4R and 4S threitolceramide induced a less potent response while little IL-12p40 was detected in the presence of arabinitolceramide.

Similar responses were obtained when iNKT cell activation was examined. Release of IFN-γ by the iNKT cells in response to stimulation by analogs presented by DC induced approximately 40 ng/ml IFN-γ in the presence of α-GalCer, 20 ng/ml with threitolceramide and glycerolceramide and no detectable IFNγ when arabinitolceramide was added to the culture (FIG. 4C).

From these assays, threitolceramide was found to be a potent, lower affinity analog of α-GalCer. To compare the functions of high affinity α-GalCer, intermediate affinity threitolceramide with the known, low affinity analog OCH, the three compounds were titrated onto DC and used to present to iNKT cells. Maturation of DC and DC viability were examined after 48 h. Although α-GalCer induced maximal DC maturation at only 0.8 ng/ml compared with 67 ng/ml for threitolceramide or OCH, at the same concentrations (FIG. 4D) only 10% of DC were still viable when stimulated with α-GalCer, while a significantly greater proportion of DC were propidium iodide negative when either analog was used (FIG. 4E). These data show that threitolceramide can induce good functional responses from iNKT cells in vitro, while maintaining significant DC viability compared with α-GalCer.

These data suggest that lower affinity analogs of α-GalCer can stimulate potent iNKT-cell dependent DC maturation without the significant DC killing observed with α-GalCer. Unlike OCH, threitolceramide should have the same binding affinity for CD1d as the sphingosine and acyl chains are identical to those in α-GalCer.

The following Experiments further exemplify potential uses of this new class of CD1d ligands:

Stimulation of iNKT cells by α-GalCer in the context of CD1d rapidly induces release of significant levels of a number of cytokines including IFN-γ and IL-4 (Burdin, Brossay et al, J Immunol, 1998, 161; 3271-81), IL-3 and GM-CSF (Leite-de-Moraes, Lisbonne et al, Eur J Immunol, 2002, 32; 1897-904) with other downstream cell-types including DC (Kitamura, Iwakabe et al, J Exp Med, 1999, 189; 1121-8) and NK cells (Carnaud, Lee et al, J Immunol, 1999, 163; 4647-50) being activated. Analogs such as OCH (Miyamoto, Miyake et al, Nature, 2001, 413; 531-4) and 20:2 (Yu, Inn et al, Proc Natl Acad Sci USA, 2005, 102; 3383-8) have been shown to induce a modified cytokine response, with IL-4 release but little or no IFN-γ. Injection of glycerolceramide into wild type mice did not induce any detectable cytokine release (FIG. 5. B and C) as would be expected by the lack of iNKT cell-dependent DC (FIG. 5A). However when threitolceramide or arabintolceramide were injected, IL-4 (FIG. 4B), IFN-γ (FIG. 5C) and IL-12p40/70 (data not shown) were detected in the serum with a similar time-course to that seen with α-GalCer. Both compounds were less potent than α-GalCer at equivalent doses. Neither compound showed a skewed Th2 cytokine response as seen with OCH (Miyamoto, Miyake et al, Nature, 2001, 413; 531-4, Silk, Hermans et al, J Clin Invest, 2004, 114; 1800-11).

Adjuvant Function of α-GalCer Analogs Induces Effective Tumour Specific T Cell Responses In Vivo.

Previously we, and others have shown that co-injection of model antigens such as OVA (Silk, Hermans et al, J Clin Invest, 2004, 114; 1800-11, Fujii, Shimizu et al, J Exp Med, 2003, 198; 267-79, Hermans, Silk et al, Immunol, 2003, 171; 5140-7) and β-galactosidase (Silk, Hermans et al, J Clin Invest, 2004, 114; 1800-11) together with α-GalCer induces enhanced CD8$^+$, CD4$^+$ T cell and B cell responses. These were effective for therapy against tumour cells expressing the target antigen. The various analogs were co-injected with OVA into wild type mice and 6 days later the blood examined for the presence of antigen-specific CD8$^+$ T cells using fluorescent $K^b$-SIINFEKL tetramers. Both arabintolceramide and threitolceramide induced a significant CD8$^+$ T cell response after 6 days, although less potently than α-GalCer, while glycerolceramide did not (FIG. 6A). Sera from the mice were examined for the presence of OVA-specific antibodies using ELISA and showed responses of similar ranking order to those seen with CD8$^+$ T cells (FIGS. 7B and 7C).

B Cell Responses.

Non-glycolipid analogs of α-GalCer stimulate B cell maturation in the presence of iNKT cells in vivo and subsequent antibody production. (A) C57BL/6 or iNKT$^{-/-}$ mice were injected i.v. with 1 μg of vehicle, α-GalCer, analog or 25 μg MPL. Twenty hours after injection splenocytes were stained with antibodies against B220 and CD86 and analyzed by flow cytometry. Maturation was assessed by the upregulation of CD86 at the cell surface, gating on B cells (B220$^+$) (FIG. 7A). Mean fluorescence intensity for each histogram is indicated. (B) Simultaneous administration of 1 μg α-GalCer or analogs and 400 μg OVA induces significant OVA-specific IgGs. Mice were bled 11-14 d after administration and the serum tested by ELISA for antibodies (FIG. 7 B).

Priming of antigen specific T cell responses using human in vitro priming Model.

Experiments carried out with human peripheral blood lymphocytes demonstrated that threitol-ceramide is superior than glycerol-ceramide in expanding Melan-A$_{26-35}$ specific T cell responses. (FIG. 8)

II. Inositol Derivative Analogs of α-GalCer

Subsequently, a new panel of novel α-GalCer analogs was generated. The first was an inositolceramide with a 25-carbon fatty acid chain (INOC-25). INOC-25 induced detectable DC maturation and cytokine production from iNKT cells. (Data not shown). Further structural modifications were made to generate 6-Sulfono-myo-inositolceramide and 6-Deoxy-myo-inositolceramide. These compounds were tested for their effects on DC maturation in the human co-culture system (FIG. 9A) and in mice in vivo (unpublished data). While the inositol derivative INOC-25 induced little DC maturation (data not shown) by upregulation of CD83 and CD86, both 6-Deoxy and 6-Sulfono-myo-inositolceramide induced significant DC maturation in an iNKT cell dependent manner (FIG. 9A.) to a similar extent to that observed with α-GalCer.

Similar to that observed with DC maturation (FIG. 9A.), IL-12p40 production by the DC was almost identical between et-GalCer and 6-Deoxy-myo-inositolceramide, while the 6-Sulfono derivative was slightly weaker (FIG. 9B). However the amount of IL-12p40 produced by the DC in response to iNKT cells stimulated by the 6-Deoxy and 6-Sulfono derivative analogs was significantly above that from the INOC-25 (not shown) and also greater than that observed with LPS. The supernatants from the DC co-cultures with the inositol derivative compounds were examined for IFN-γ as a measure of iNKT cell activation. While the 6-Deoxy compound induced similar IFN-γ release to that observed with addition of α-GalCer (FIG. 9C), 6-Sulfono-myo-inositolceramide induced very little IFN-γ release from the iNKT cells.

The three inositol compounds were titrated on C1R cells expressing human CD1d and used to stimulate an iNKT cell clone. From both the IFN-γ (FIG. 9D.) and the IL-4 release (FIG. 9E.) it appears that while the INOC-25 induced little or no IFN-γ and IL-4, 6-Deoxy inositolceramide stimulated release of significant levels of both cytokines from the iNKT cells. Interestingly, as observed when co-cultured with DC (FIG. 9C), while 6-Sulfono inositolceramide stimulated little or no IFN-γ release (FIG. 9D), detectable IL-4 was produced when higher concentrations of the compound were used (FIG. 9E).

In comparison with α-GalCer, each of the inositol derivative compounds appeared to have lower affinity. Both in terms of IFN-γ (FIG. 9C) and IL-4 (FIG. 9B) α-GalCer induces release of significantly higher concentrations of cytokines. IFN-γ and IL-4 appeared to be approaching a plateau when stimulated with 200 ng/ml α-GalCer. Although IFN-γ and IL-4 induced by the inositol derivatives also appear to be titrating with increasing concentration of compound, they did not approach the levels induced by α-GalCer.

It is possible that while C1R cells are effective at presenting higher affinity ligands such as α-GalCer, they are less effective at presenting lower affinity compounds than professional APCs such as DC. This may explain the difference in the magnitude of cytokine production observed between analogs presented by DC and by CD1d-transfected C1R cells.

Conclusions: Fine tuning the affinity of binding of the iNKT TCR to the CD1d/lipid complex and the stability of lipid ligands to CD1d molecules has led to the identification of a new group of compounds capable of inducing iNKT cell activation, without over-stimulating iNKT cells. This novel class of compounds is efficient in stabilizing CD1d molecules and it is optimized for NKT stimulation since it minimizes NKT cell dependent DC lysis and cytokine release, while ensuring DC maturation and antigen-specific T and B cell priming. This novel combination of useful molecular and biological attributes was achieved by designing a class of CD1d ligands that optimize the iNKT/CD1d interaction without compromising the stability of the CD1d/ligand complex. Such compounds can therefore be used in broader effective dose range than existing compounds.

EXAMPLE A

These experiments describe the priming of dendritic cells ("DC"s hereafter). In this, and the following examples, Compound 1, arabinitol ceramide; Compound 2, glycerol ceramide; or Compound 3, threitol ceramide derivatives) were used.

The methodology of Salio, et al., *J. Immunol.*, 167:1188-1197 (2001), incorporated by reference, was followed. In brief, 2×105 human monocyte derived DCs were pulsed with 100 ng/ml of one of Compounds 2, 3, αGal-Cer, or vehicle solution, as a control. For DC pulsing, each of arabinitol ceramide (Compound 1), threitol ceramide (Compound 3), glycerol ceramide (Compound 2) and αGal-Cer was solubilized in vehicle solution (0.5% Tween 20/PBS), and added to the medium of the DC cultures. NKT cells were also added to the DC cultures at a ratio of 10 DC/NKT cell. After 36 hours, supernatant was removed from cultures and analyzed for the presence of known DC maturation markers CD83, CD80, CD86, CD25, and CD38, all of which were analyzed via FACS, using well known methods.

The results indicated that when DCs are combined with NKTs in the presence of either Compound 1 (arabinitol ceramide) or Compound 2 (glycerol ceramide) or Compound 3 (threitol ceramide) DC maturation markers are induced. Levels of maturation marker induction are similar to those seen with αGal-Cer. No upregulation was seen with controls.

In addition, interleukin-12 levels (IL-12, were measured as an indication of DC stimulation by detecting the p40 form of IL-12 via ELISA, using standard methods. As NKT cells do not produce IL-12 this indicates a DC specific response. All compounds produced secretion of IL-12 in this assay. Compound 3 was seen to be approximately 50% as potent as αGal-Cer in this assay whilst Compounds 1 and 2 were approximately 1000 fold less potent than Compound 3 confirming differing biological activities of these compounds in this assay system.

EXAMPLE B

In these experiments, T cell expansion was measured, by pulsing human DCs from PBLs with 100 nM of the known, immunogenic peptide MelanA26-35, ELAGIGILTV. The peptide was added to the DCs together with syngeneic PBLs from the same donor. To detail these experiments more fully, samples of DCs were irradiated with 3000 rads followed by a 3 hour pulse with the peptide, in serum free medium.

The cells were then washed thoroughly and incubated with autologous, PBLs, at a 1:10 ratio, in RPMI 1640/5% human serum. Recombinant human IL-2 was added at 10 U/ml from day 4 to day 7. At day 10, following the addition of the PBLs, cells were analyzed. Cultured cells were stained with anti-CD8 and A2/MelanA2S-35 tetramer. The percentage of MelanA specific CD8 T cells out of total CD8 positive cells was measured by FACS analysis.

The results indicated that when human DCs were incubated in the presence of NKT cells, threitol and glycerol cross-priming occurs and that both compounds were more potent stimulators of antigen specific CTL responses, in vitro, than αGal-Cer. This confirms that both Compound 2, glycerol ceramide and Compound 3, threitol ceramide are likely to be useful as CD8+ CTL immunostimulants and suggests that other compounds of the invention may behave similarly.

EXAMPLE C

These animal experiments detail work designed to study the impact of the compounds of the invention in vivo.

Subject animals, five mice per group, received an intravenous injection of 400 µg of ovalbumin (OVA) together with 1 µg of one of the compounds of the invention under examination or an equivalent volume of PBS diluted vehicle solution. A subset of mice were injected with 25 µg of the molecule MPL (Sigma-Aldrich; extracted from *Salmonella* Minnesota) solubilized in PBS.

Following the injections, blood was obtained from lateral tail veins, and PBLs were isolated, using standard methods. The PBLs were then stained, directly, in vivo, with tetrameric, H-2 Kb/OVA 257-264, H-2 Kb complexes, following Palmowski, et al., *J. Immunol.*, 168:4391-4398 (2002), incorporated by reference. The tetramers were prepared in accordance with Whilan, et al., *J. Immunol.*, 163:4342-4348 (1999), incorporated by reference.

When the PBLs from naïve animals were compared to those from animals stained with irrelevant tetramers the background stainings were equivalent.

There was an enhancement of the OVA specific response when αGal-Cer, Compound 1, arabinitol ceramide, or Compound 3, threitol ceramide were used. Enhancement was weakest with Compound 2, glycerol ceramide.

When MPL was coinfected with either αGal-Cer or Compound 3, threitol ceramide, there was an enhancement of the CTL response as might be expected from Silk et al., *J. Clin. Invest.*, 114:1800-1811, 2004.

EXAMPLE D

These experiments assessed the presence of OVA specific IgG antibodies in the serum of mice which had been injected with the OVA protein.

OVA protein coated ELISA plates, were prepared, using well known methods. Then, blood samples were taken, ten days following immunization, and serum was prepared.

The samples were taken from mice that had been immunized with OVA only, OVA and Compound 1, arabinitol ceramide, OVA and αGal-Cer, or OVA and Compound 2, glycerol ceramide. Additionally, mice were immunized with each of these schedules with MPL added. Serum IgG titers were measured by adding serial dilutions of mouse serum were detected using horseradish peroxidase (HRP) conjugated α-mouse IgG.

The data indicated that the compounds of the invention produce OVA specific antibody responses. Compound 1, arabinitol ceramide and αGal-Cer were seen to be more effective as adjuvants than MPL whereas Compound 2, glycerol ceramide, was less effective than MPL whilst still producing OVA specific antibodies.

Additionally, when MPL was added strong enhancement of the response was seen in all cases demonstrating that compounds of the invention when used in combination with a TLR4 ligand are extremely efficient in expanding the titer of antigen specific antibodies.

EXAMPLE E

In these experiments, the DCs obtained from the spleen of subject animals were phenotyped.

In brief, in each experiment, 1 µg of one of a selection of compounds of the invention was injected into the tail vein of subject mice. 24 h later spleen tissue was removed from the animals and gently teased through gauze into complete medium, supplemented with 5 mM of EDTA. Cells were enriched for CD11c by anti-CD11, magnetic beads using published techniques. Once enriched, they were assayed for maturation markers using antibody staining and flow cytometry. Non-specific staining was addressed by using an antibody specific for the Fc-RIII/II receptor.

Compound 1, arabinitol ceramide, and Compound 2, threitol ceramide and αGal-Cer all induced CD86 in vivo similarly, confirming that both these compounds in mice are highly efficient at producing T cell as well as B cell responses. In contrast, Compound 3, glycerol ceramide, did not induce the DC86 marker significantly. These results show that while the MPL and glycerol combination is effective in driving antigen specific B cell responses (Examples 25 and 26) in mice, DC maturation and T cell expansion do not appear to be significantly enhanced by Compound 2, glycerol ceramide. This contrasts to the finding in humans where Compound 2, glycerol ceramide, matures DC cells in the presence of NKT cells which then serve as efficient primers of human CTLs.

EXAMPLE F

These experiments were performed to determine the effect of selected compounds of the invention in stimulating the production of IL-12 production in subject animals. The animals received 1 µg or 10 µg of threitol, glycerol or Gal-Cer. One group of animals also received 50 µg of MPL. Six hours following injection, tail blood samples were collected and the IL-12 p70 protein was determined using an ELISA all in accordance with standard procedures.

Dose dependent increases in IL-12/p70 secretion were observed with Compound 3, threitol ceramide treated mice, confirming the potency of this molecule in inducing IL-12/p70 release. The effectiveness of Compound 3 compares extremely favorably with MPL.

DETAILED DESCRIPTION OF PREFERRED EMBODIMENTS

Compound 1: Arabinitol Ceramide (a) L(+) arabinose was converted into the arabinitol triflate compound, i.e.

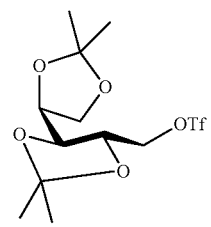

in accordance with well known procedures. See, Zinner, et al., *Chem. Ber.*, 92:1614 (1959); Qin, et al., *Can. J. Chem.*, 77:481 (1999); and, Yann, et al., *Carbohydr. Res.*, 74:323 (1979), all incorporated by reference. This compound was combined with a sphingosine component, i.e.,

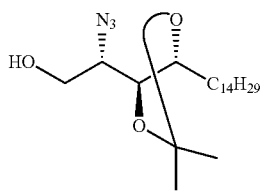

which was synthesized from 4,6-O-benzylidene-D-galactose (Gros, et al., *J. Org. Chem.*, 29:3647 (1941)), following any of Zimmermann, et al., *Liebigs Ann. Chem.*, 663 (1988); Schmidt, et al., *Carbohydr. Res.*, 172:169 (1988) and Figueroa-Perez, et al., *Carbohydr. Res.*, 328:95 (2000).

Once these two compounds were available, a solution of the sphingosine component (220 mg, 0.575 mmol), in 3 ml of anhydrous THF, and 95% NaH (17 mg, 0.708 mmol) was added at 0° C. After 15 minutes of stirring, a solution of the arabinitol triflate compound (251 mg, 0.690 mmol), in 2 mL, of anhydrous THF was added at the same temperature. The resulting mixture was warmed, slowly, to room temperature, and then stirred overnight. The reaction mixture was quenched with an aqueous solution of $NH_4Cl$, taken up into EtOAc, and the layers were separated.

The organic layer was washed with water, dried over anhydrous $MgSO_4$, and evaporated to dryness. Crude material was purified via flash chromatography (1:9, ethylacetate:petroleum ether, yielding:

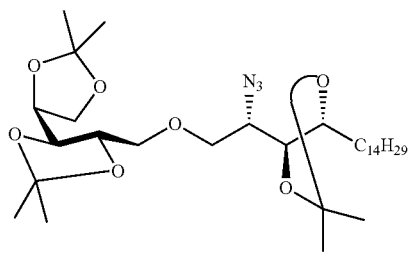

as a colourless liquid (yield: 95%). $R_f$=0.54 (1:9, ethyl acetate:petroleum ether). $[\alpha]_D^{25}$=+5.2 (c 1.0, $CHCl_3$). $^1$H NMR (250 MHz, $CDCl_3$): δ 4.19-4.00 (m, 5H), 3.99-3.86 (m, 2H), 3.84-3.61 (m, 5H), 1.60-1.25 (m, 26H), 1.41 (s, 3H), 1.40 (br s, 6H), 1.38 (s, 3H), 1.33 (s, 3H), 1.30 (s, 3H), 0.87 (t, J=6.5 Hz, 3H). $^{13}$C NMR (62.5 MHz, $CDCl_3$): δ 109.6, 108.2, 96.0, 79.7, 77.7, 77.07, 77.3, 75.7, 72.8, 71.8, 67.5, 60.0, 31.9, 29.6, 29.5, 29.66, 29.62 29.59, 29.56, 29.4, 29.3, 28.1, 26.9, 26.6, 26.4, 25.6, 25.2, 22.6, 14.1. MALDI-MS (positive mode, Matrix CHCA): m/z 620.2 $[M+Na]^+$. Anal. Calcd for $C_{32}H_{59}N_3O_7$ (597.43): C, 64.29; H, 9.95; N, 7.03. Found: C, 64.35; H, 10.01; N, 7.15

(b) The product of (a) above (150 mg, 0.251 mmol), and 10% Pd/C (100 mg) in 4 ml methanol with a drop of acetic acid was stirred, under an $H_2$ atmosphere, for 20 hours, at room temperature. Then the mixture was filtered, concentrated, and co-evaporated with toluene. The resulting syrup was dissolved in 5 ml of dry DMF, and then hexacosanoic acid (Fluka) (120 mg, 0.303 mmol), N-hydroxy-benzotriazole (40 mg, 0.301 mmol), and 1-[3-(dimethylamino-propyl]-3 ethyl-carbodiimide hydrochloride (EDC, 58 mg, 0.303 mmol) were added successively, and the resulting mixture was stirred at 45° C. for 1 day. The mixture was taken in ethyl acetate washed with water, saturated brine solution, dried over anhydrous $MgSO_4$, and concentrated. Residue was purified by flash chromatography to yield 182 mg of

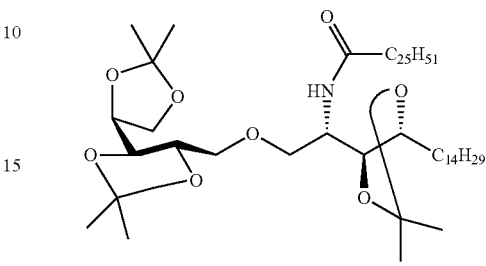

as a colourless solid (yield: 75%). mp 89° C. $R_f$=0.46 (2:8, ethyl acetate:petroleum ether). $[\alpha]_D^{25}$=+11.4 (c 1.0, $CHCl_3$). NMR (250 MHz, $CDCl_3$): δ 5.84 (d, J=8.5 Hz, 1H), 4.25-4.00 (m, 1H), 3.98-3.92 (m, 1H), 3.85-3.74 (m, 2H), 3.70-3.62 (m, 1H), 3.56-3.49 (m, 2H), 2.17-2.11 (m, 2H), 1.60-1.24 (m, 72H), 1.41 (s, 3H), 1.38 (s, 6H), 1.36 (s, 3H), 1.32 (br s, 6H), 0.86 (t, J=6.7 Hz, 3H). $^{13}$C NMR (62.5 MHz, $CDCl_3$): δ 172.4, 109.6, 107.8, 79.8, 77.9, 77.8, 77.1, 76.1, 72.4, 71.3, 67.6, 48.3, 36.9, 29.69, 29.64, 29.5, 29.3, 29.0, 28.0, 27.1, 27.0, 26.7, 26.4, 25.77, 25.72, 25.2, 22.6, 14.0. MALDI-MS (positive mode, Matrix CHCA): m/z 972.6 $[M+Na]^+$. Anal. Calcd for $C_{58}H_{111}NO_8$ (949.83): C, 73.29; H, 11.77; N, 1.47. Found: C, 73.59; H, 11.99; N, 1.41

(c) The product of (b) above (120 mg, 0.123 mmol) in $MeOH:CH_2Cl_2$ (10:1, 22 ml) containing TFA (100 µl), was stirred at room temperature for 3 days. The solid resulting was filtered and dried to give

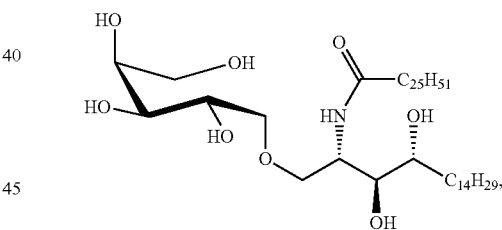

hereinafter referred to as Compound 1 ('arabinitol-ceramide'), 63 mg, 60% yield, mp 125° C., $^1$H NMR (400 MHz, $C_5D_5N$): δ 8.66 (d, J=8.8 Hz, 1H), 5.30-5.25 (m, 2H), 4.98-4.94 (m, 1H), 4.66-4.58 (m, 2H), 4.44-4.22 (m, 2.57-2.53 (m, 2H), 2.07-1.37 (m, 72H), 0.99 (t, =6.7 Hz, 6H). $^{13}$C NMR (150.9 MHz, $C_5D_5N$): δ 173.3, 78.1, 76.3, 74.6, 73.2, 72.7, 71.3, 70.0, 65.4, 51.8, 36.8, 32.1-29.6 (in), 26.4, 22.9, 14.1. MALDI-MS (positive mode, Matrix CHCA): m/z 853.3 $[M+Na]^+$. Anal. Calcd for $C_{49}H_{99}NO_8$ (830.73): C, 70.88; H, 12.02; N, 1.69. Found: C, 73.59, H, 11.99; N, 1.41.

Compound 2: Glycerol Ceramide

The procedure of 1(a) above was repeated using

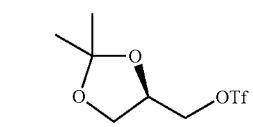

as the triflate starting material (Cassel, et al., *Eur. J. Org Chem.*, 875 (2001)) to give

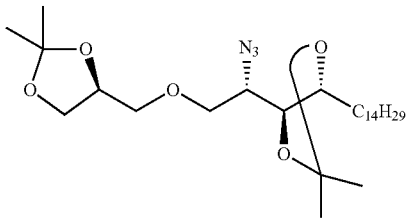

as a colourless solid (yield: 90%). $R_f$=0.47 (1:9, ethyl acetate: petroleum ether). $[\alpha]_D^{25}$=+24.6 (c 1.0, CHCl$_3$). $^1$H NMR (250 MHz, CDCl$_3$): δ 4.32-4.23 (m, 1H), 4.16-4.04 (m, 2H), 3.96 (d, J=7.8 Hz, 1H), 3.87-3.76 (m, 2H), 3.68-3.48 (m, 4H), 1.57-1.18 (m, 26H), 1.42 (s, 3H), 1.40 (s, 3H), 1.36 (s, 3H), 1.30 (s, 3H), 0.87 (t, J=6.5 Hz, 3H). $^{13}$C NMR (62.5 MHz, CDCl$_3$): δ 109.3, 108.2, 77.7, 75.6, 74.5, 72.8, 72.4, 66.7, 59.8, 31.8, 29.6, 29.5, 29.4, 29.3, 29.1, 28.0, 26.7, 26.3, 25.6, 25.3, 22.6, 14. 1. MALDI-MS (positive mode, Matrix CHCA): m/z 520.1 [M+Na]$^+$. Anal. Calcd for C$_{27}$H$_{51}$N$_3$O$_5$ (497.38): C, 65.16; H, 10.33; N, 8.44. Found: C, 65.25; H, 10.41; N, 8.50.

(b) The procedure of 1(b) was repeated using product of (a) above to give

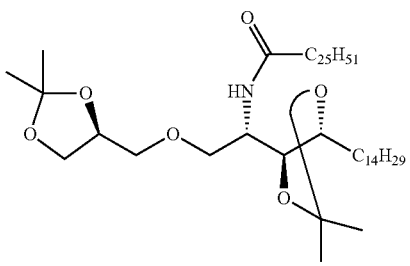

as a colorless solid (yield 72%). mp 81° C. $R_f$=0.43 (2:8, ethyl acetate:petroleum ether). $[\alpha]_D^{25}$=+13.5 (c 1.0, CHCl$_3$). $^1$H NMR (400 MHz, CDCl$_3$): δ 5.75 (d, J=9.0 Hz, 1H), 4.27-4.00 (m, 5H), 3.74 (dd, J=9.3, 3.1 Hz, 1H), 3.69 (dd, J=8.2, 6.2 Hz, 1H), 3.54-3.45 (m, 3H), 2.20-2.07 (m, 2H), 1.60-1.23 (m, 72H), 1.40 (s, 6H), 1.34 (s, 3H), 1.31 (s, 3H), 0.86 (t, J=6.8 Hz, 6H). $^{13}$C NMR (100 MHz, CDCl$_3$): δ 172.4, 109.4, 107.8, 77.7, 75.9, 74.7, 72.5, 66.4, 48.1, 36.9, 31.8, 29.6, 29.5, 29.39, 29.34, 29.2, 28.9, 27.9, 26.7, 26.4, 25.7, 25.3, 22.6, 14.1. MALDI-MS (positive mode, Matrix CHCA): m/z 873.2 [M+Na]$^+$. Anal. Calcd for C$_{53}$H$_{103}$NO$_6$ (849.77): C, 74.86; H, 12.21; N, 1.65. Found: C, 74.81; H, 12.26; N, 1.70.

(c) The procedure of 1(c) above was repeated using the product of (b) above to give

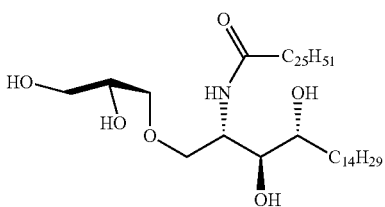

as a colorless solid, hereinafter referred to as Compound 2 ('glycerol ceramide'). Yield 70%, mp 140° C. $^1$H NMR (400 MHz, C$_5$D$_5$N): δ 8.64 (d, J=8.67 Hz, 1H), 4.92-4.83 (m, 1H), 4.60-4.56 (m, 1H), 4.41-4.31 (m, 2H), 4.12-3.96 (m, 6H), 2.57 (t, J=7.2 Hz, 2H), 2.03-1.37 (m, 72H), 0.99 (t, J=6.8 Hz, 6H). MALDI-MS (positive mode, Matrix CHCA): m/z 793.6 [M+Na]$^+$. Anal. Calcd for C$_{47}$H$_{95}$NO$_6$ (769.72): C, 73.29; H, 12.43; N, 1.82. Found: C, 73.33; H, 12.47; N, 1.91.

Compound 3: Threitol Ceramide

Compound (100 mg, 0.4 mmol) as prepared according to in accordance with well known procedures (see, Wagner, et al., *J. Chem. Soc., Perkin Trans.* 1, 780 (2001))

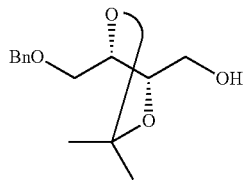

was added to 2,6-di-tert-butylpyridine (92 mg, 0.48 mmol) in anhydrous CH$_2$Cl$_2$ mL), Tf$_2$O (0.08 mL, 0.48 mmol) dissolved in anhydrous CH$_2$Cl$_2$ (1 mL) with stirring at 0° C. The reaction mixture was stirred at the same temperature for 1 hour. The reaction mixture was taken in ethyl acetate and washed with cold water (2×15 mL). The combined organic layers were washed with brine solution, dried and evaporated to get the crude product which was purified by silica gel column chromatography (1:10, ethyl acetate:petroleum ether containing drops of Et$_3$N) to give

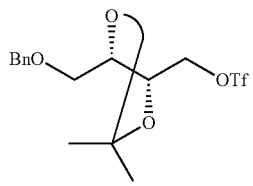

(145 mg, 95%). $R_f$ 0.41 (1:10, ethyl acetate:petroleum ether). NMR (250 MHz, CDCl$_3$): δ 7.41-7.27 (m, 5H), 4.71 (dd, J=10.9, 2.8 Hz, 1H), 4.57 (s, 2H), 4.50 (dd, J=10.9, 4.9 Hz, 1H), 4.14 (ddd, J=8.0, 4.9, 2.8 Hz, 1H), 4.05 (ddd, J=8.1, 6.3, 4.5 Hz, 1H), 3.73 (dd, J=9.7, 4.5 Hz, 1H), 3.55 (dd, J=9.7, 6.3 Hz, 1H), 1.42 (s, 6H). $^{13}$C NMR (62.5 MHz, CDCl$_3$): δ 128.6, 128.5, 128.0, 127.7, 110.7, 76.8, 75.03, 75.00, 73.8, 69.9, 26.9, 26.6.

(b) The procedure of 1(a) above was followed using the product of (a) above to give

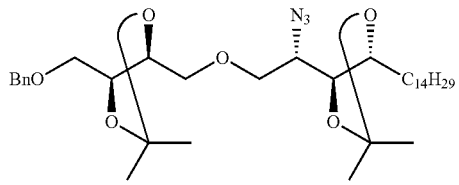

which was purified by flash chromatography (1:9, ethyl acetate:petroleum ether) yielding a colorless liquid (306 mg, 94%). $R_f$=0.46 (1:9, ethyl acetate:petroleum ether). $[\alpha]_D^{25}$=+ 7.3 (c 1.0, CHCl$_3$). $^1$H NMR (250 MHz, CDCl$_3$): δ 7.36-7.23 (m, 5H), 4.50 (s, 2H), 4.17-3.98 (m, 3H), 3.94 (dd, J=9.8, 2.0 Hz, 1H), 3.83 (dd, J=9.2, 5.6 Hz, 1H), 3.70-3.53 (m, 6H), 1.62-1.21 (m, 26H), 1.43 (s, 6H), 1.40 (s, 3H), 1.30 (s, 3H), 0.88 (t, J=6.2 Hz, 3H). $^{13}$C NMR (62.5 MHz, CDCl$_3$): δ 138.0, 128.3, 127.63, 128.60, 109.6, 108.2, 77.8, 77.5, 77.4, 75.7, 73.5, 72.9, 72.2, 70.6, 60.0, 31.9, 29.7, 29.62, 29.57, 20.5, 29.4, 29.3, 28.1, 27.0, 26.4, 25.6, 22.7, 14.1, 4.8. MALDI-MS (positive mode, Matrix DHB): m/z 640.9 [M+Na]$^+$.

(c) The procedure of 1(b) above was followed using the product of (b) above to yield

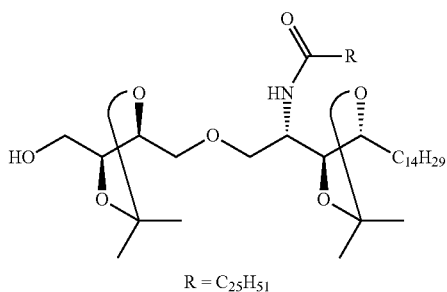

R = C$_{25}$H$_{51}$ which was purified by flash chromatography (4:6, ethyl acetate:petroleum ether) to yield a colorless solid (116 mg, 81%). R$_f$=0.23 (3:7, ethyl acetate:petroleum ether). $^1$H NMR (250 MHz, CDCl$_3$): δ 5.74 (d, I=8.7 Hz, 1H), 4.27-4.14 (m, 1H), 4.13-3.99 (m, 3H), 3.93-3.87 (m, 1H), 3.81 (3.55 (m, 6H), 2.20-2.13 (m, 2H), 1.65-1.20 (m, 72H), 1.42 (s, 9H), 1.33 (s, 3H), 0.88 (t, J=6.3 Hz, 6H). $^{13}$C NMR (62.5 MHz, CDCl$_3$): δ 172.6, 109.2, 107.9, 79.2, 77.7, 76.7, 76.2, 71.9, 71.6, 62.4, 48.1, 36.9, 31.9, 29.6, 29.5, 29.4, 29.3, 29.0, 27.9, 26.9, 26.4, 25.7, 25.6, 22.6, 14.4, 14.0. MALDI-MS (positive mode, Matrix DHB): m/z 902.4 [M+Na]$^+$.

(d) The procedure of 1(c) above was repeated using the products of (c) above to yield

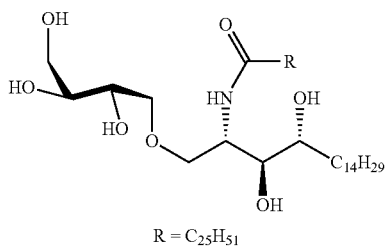

R = C$_{25}$H$_{51}$ a colorless solid (71 mg, yield 71%), hereinafter referred to as Compound 3 ('threitol ceramide'). $^1$H NMR (250 MHz, C$_5$D$_5$N): δ 8.62 (d, J=8.6 Hz, 1H), 4.81-4.05 (m, 9H), 2.52-2.39 (m, 2H), 2.35-1.15 (m, 72H), 0.87-0.83 (m, 6H). MALDI-MS (positive mode, Matrix CHCA): m/z 822.9 [M Na]$^+$.

Compound 4: Threitol Ceramide C$_{15}$ acyl (a) The product of 3(b) above e.g.

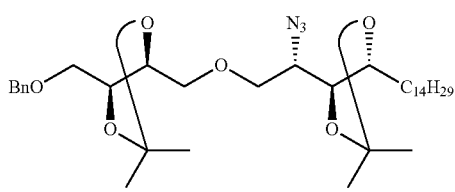

(175 mg, 0.284 mmol) and 10% Pd/C (1.50 mg) in methanol (3 mL) containing a drop of acetic acid was stirred under H$_2$ atmosphere (balloon) at room temperature for 22 hours. Then the mixture was filtered, concentrated and co-evaporated with toluene. The resulting syrup was dissolved in dry DMF (4 mL). Palmitic acid (Fluka) (73 mg, 0.284 mmol), N-hydroxybenzotriazole (38 mg, 0.284 mmol) and 1-[3-(dimethylamino)-propyl]-3-ethylcarbodiimide hydrochloride (54 mg, 0.284 mmol) were added successively and the resulting mixture was stirred at 45° C. for 1 clay. Then it was taken in ethyl acetate washed with water, saturated brine solution, dried over anhydrous MgSO$_4$, and concentrated. The residue was purified by silica gel chromatography (4:6, ethyl acetate: petroleum ether) to yield

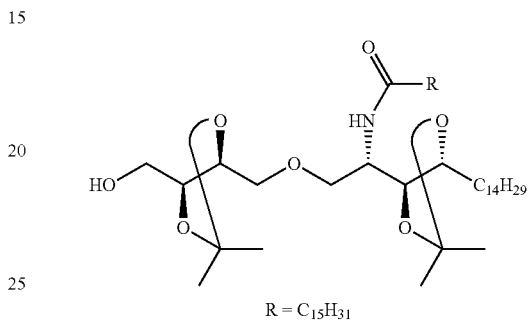

R = C$_{15}$H$_{31}$ (168 mg, 80%). R$_f$=0.16 (7:3 ethyl acetate:petroleum ether). [α]$_D^{25}$=+11.6 (c 1.0, CHCl$_3$). $^1$H NMR (250 MHz, CDCl$_3$): δ 5.77 (d, J=9.4 Hz, 1H), 4.27-4.14 (m, 1H), 4.13-3.99 (m, 3H), 3.93-3.87 (m, 1H), 3.81-3.55 (m, 6H), 2.20-2.13 (m, 2H), 1.75-1.20 (m, 52H), 1.42 (s, 9H), 1.33 (s, 3H), 0.88 (t, J=6.4 Hz, 6H). MALDI-MS (positive mode, CHCA): m/z 762.9 [M+Na]$^+$. 778.8 [M+K]$^+$.

(b) The product of (a) above (120 mg, 0.162 mmol) is MeOH/CH$_2$Cl$_2$ (10:1, 22 mL) containing TFA (100 μL) was stirred at room temperature for 65 hours. The solid that dropped out, was filtered and dried to obtain

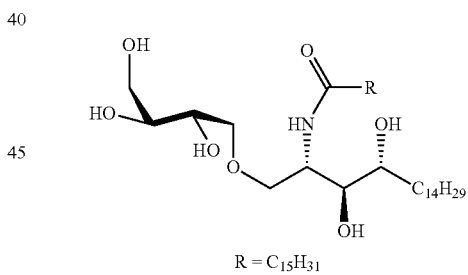

R = C$_{15}$H$_{31}$ (70 mg, yield 65%) hereinafter referred to as Compound 4, ('threitol ceramide C15 acyl') $^1$H NMR (250 MHz, DMSO-d$_6$): δ 5.45-5.35 (m, 1H), 4.60-3.75 (m, 10H), 2.04-1.89 (m, 2H), 1.57-1.02 (m, 52H), 0.83-0.72 (m, 6H). MALDI-MS (positive mode, CHCA): m/z 682.8 [M+Na]$^+$, 698.6 [M+K]$^+$.

Synthesis 22-(Z)-Hexacosanoic acid (a) THP-protected-11-bromoundecanol (10.0 g, 29.85 mmol) e.g.

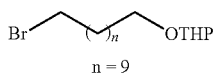

n = 9 and magnesium (1.0 g, 41.66 mmol) in dry THF (150 mL), were heated under reflux for a 3-4 hour period to make the Grignard reagent. This was added to 11-bromoundecanoic acid (8.0 g, 30.22 mmol) e.g.

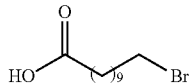

in dry THF (100 mL) under argon at −20° C. Methylmagnesium chloride in THF (−10.2 mL, 3 M) was added until cessation of gas evolution stopped, $Li_2CuCl_4$ was then added, stirring at −20° C. continued for 1 hour, and then temperature was allowed to rise to room temperature. After 15 hours, the reaction mixture was carefully neutralized with 10% $H_2SO_4$ and extracted with ethyl acetate (2×150 mL). The organic layer was dried over $MgSO_4$, and concentrated to give colourless solid, which was purified by flash chromatography (1:9 ethyl acetate:petroleum ether) give

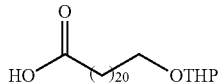

(10.9 g, 82% yield). This compound was dissolved in THF (50 mL) and esterified with diazomethane. The solvent was evaporated, and purified by chromatography (5:95 ethyl acetate:petroleum ether) to give the ester of THP-protected-11-bromoundecanol e.g.

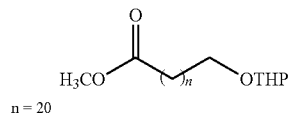
n = 20 as a colourless solid (10.9 g, 97% yield). $R_f$=0.65 (5:95, ethyl acetate:petroleum ether). $^1$H NMR (250 MHz, $CDCl_3$): δ 4.56 (t, J=3.3 Hz, 1H), 3.90-3.81 (m, 1H), 3.76-3.65 (m, 1H), 3.65 (s, 3H), 3.52-3.45 (m, 1H), 3.40-3.31 (m, 1H), 2.28 (t, J=7.5 Hz, 2H), 1.62-1.51 (m, 10H), 1.23 (br. s, 321-1). $^{13}$C NMR (62.5 MHz, $CDCl_3$): δ 174.3, 98.8, 67.7, 62.3, 51.4, 34.1, 30.7, 29.7, 29.68, 29.63, 29.60, 29.49, 29.44, 29.2, 29.1, 26.2, 25.5, 24.9, 19.6. MALDI-MS (positive mode, CHCA): m/z 477.3 [M+Na]$^+$.

(b) The product of (a) above (8.0 g, 17.62 mmol) in methanol (200 mL) was treated with p-toluenesulfonic acid (6.7 g, 35.26 mmol). The reaction mixture was stirred for 3-4 hours. After completion of reaction, (TLC monitoring) solvent was evaporated and the residue was dissolved in chloroform and washed with saturated $NaHCO_3$ solution. The chloroform layer was dried and concentrated to give colourless solid, which was recrystallized (petroleum ether/ethyl acetate) to give

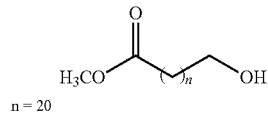
n = 20 as colourless crystals (6.4 g, 98% yield). $R_f$=0.21 (2:8, ethyl acetate:petroleum ether). $^1$H NMR (250 MHz, $CDCl_3$): δ 3.66 (s, 3H), 3.63 (t, J=6.5 Hz, 2H), 2.30 (t, J=7.5 Hz, 1H), 1.64-1.53 (m, 4H), 1.25 (br. s, 32H). $^{13}$C NMR (62.5 MHz, $CDCl_3$): δ 174.3, 63.0, 51.4, 34.1, 32.8, 29.6, 29.59, 29.58, 29.4, 29.2, 29.1, 25.7, 24.9. MALDI-MS (positive mode, CHCA): m/z 393.8 [M+Na]$^+$.

(c) The product of (b) above (6.0 g, 16.21 mmol) in dry $CH_2Cl_2$ (200 mL), was treated with Dess-Martin periodinane (DMP) (13.74 g, 32.42 mmol). The reaction mixture was stirred for 3-4 hours at room temperature. After completion of reaction, solvent was evaporated; residue was suspended in diethyl ether and filtered off. The filtrate was washed with $NaHCO_3$ solution, then brine solution. The ether layer was dried and concentrated to give solid, which was purified by flash chromatography (5:95, ethyl acetate:petroleum ether) to give

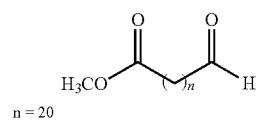
n = 20 as a colourless solid (5.5 g, 92% yield). $R_f$=0.62 (5:95, ethyl acetate:petroleum ether). $^1$H NMR (250 MHz, $CDCl_3$): δ 9.73 (t, J=1.8 Hz, 1H), 3.63 (s, 3H), 2.39 (dt, J=14.0, 7.5, 2.0 Hz, 2H), 2.26 (t, J=7.5 Hz, 2H), 1.66-1.56 (m, 4H), 1.21 (br. s, 32H). $^{13}$C NMR (62.5 MHz, $CDCl_3$): δ 202.8, 174.2, 51.3, 43.8, 34.0, 29.65, 29.61, 29.5, 29.49, 29.42, 29.40, 29.3, 29.2, 29.1, 24.9, 22.0. MALDI-MS (positive mode, CHCA): m/z 391.9 [M+Na]$^+$.

(d) A suspension of n-butyltriphenylphosphonium bromide (8.66 g, 21.73 mmol) in dry THF (80 mL) under argon at −78° C., was treated with sodium bis(trimethylsilyl) amide (21.73 mL, 1.0 M). The reaction mixture was stirred for 15 minutes, at the same temperature, before a solution of the product from of (c) above (5 g, 13.58 mmol) in dry THF (30 mL) was added, and then temperature was allowed to rise to room temperature. After completion of reaction, it was quenched with aqueous $NH_4Cl$ solution and then extracted with diethyl ether (2×80 mL). The ether layer washed with brine, dried and evaporated to give residue, which was purified by flash chromatography (5:95, ethyl acetate:petroleum ether) to give

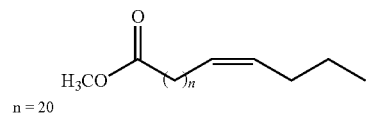
n = 20 as a colourless solid (5.42 g, 98% yield). $R_f$=0.65 (5:95, ethyl acetate:petroleum ether). $^1$H NMR (250 MHz, $CDCl_3$): δ 5.38-5.33 (m, 2H), 3.66 (s, 3H), 2.30 (t, 7.5 Hz, 2H), 2.04-196 (m. 4H), 1.67-1.56 (m, 2H), 1.40-1.25 (m, 36H), 0.90 (t, J=7.5 Hz, 3H). $^{13}$C NMR (62.5 MHz, $CDCl_3$): δ 174.3, 130.0, 129.5, 51.3, 34.1, 29.7, 29.69, 29.64, 29.59, 29.56, 29.4, 29.3, 29.28, 29.25, 29.1, 27.2, 24.9, 22.8, 13.7. MALDI-MS (positive mode, CHCA): m/z 431.8 [M+Na]$^+$.

(e) The product of (d) above (2 g, 4.893 mmol) and sodium hydroxide (2.3 g, 5.872 mmol) in methanol was heated to reflux for 2 hours after cooling with ice, the precipitate was collected, suspended in water and acidified with concentrated hydrochloric acid (~pH 1). The product was filtered off and recrystallized from glacial acetic acid to give 22-(Z)-hexacosanoic acid e.g.

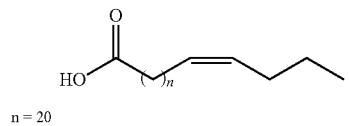

n = 20 as colourless crystals (1.9 g, 98%). $^1$H NMR (250 MHz, CDCl$_3$): δ 12.11 (s, 1H), 5.38-3.33 (m, 2H), 2.26 (t, J=7.5 Hz, 2H), 2.02-1.99 (m, 4H), 1.64-1.58 (m, 2H), 1.38-1.26 (m, 36H), 0.90 (t, J=7.5 Hz, 3H). $^{13}$C NMR (62.5 MHz, CDCl$_3$): δ 176.6, 129.8, 129.3, 33.9, 29.5, 29.49, 29.41, 29.38, 29.35, 29.31, 29.2, 29.1, 29.0, 28.9, 26.9, 24.7, 22.6, 13.5.

Compound 5: Threitol-22-(Z)-Ceramide (a) The procedure of 1(b) above was repeated using 22-(Z)-hexacosanoic acid and the product of 3(b) e.g.

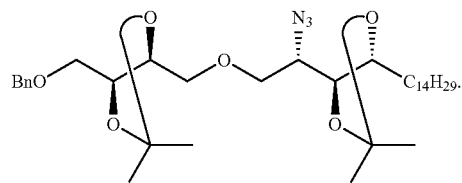

to give

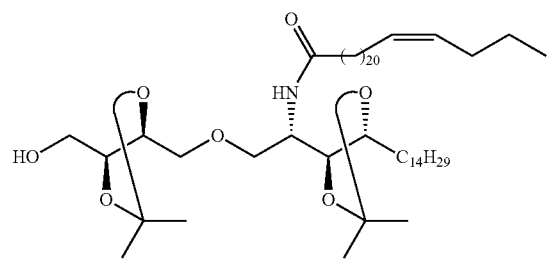

as a colourless solid (yield: 68%). R$_f$=0.23 (3:7, ethyl acetate:petroleum ether). [α]$_D^{25}$=12.7 (c 1.0, CHCl$_3$). $^1$H NMR (250 MHz, CDCl$_3$): δ 5.71 (d, J=9.5 Hz, 1H), 5.35-5.31 (m, 2H), 4.21-3.97 (m, 4H), 3.91-3.84 (m, 1H), 3.78-3.63 (m, 5H), 3.59-3.52 (m, 1H), 2.35 (br. t, J=6.7 Hz, 1H), 2.14 (dt, J=10.5, 7.5, 3.0 Hz, 2H), 2.01-1.94 (m, 4H), 1.61-1.22 (m, 76H), 0.90-0.82 (m, 6H). $^{13}$C NMR (62.5 MHz, CDCl$_3$): δ 172.5, 130.0, 129.5, 109.2, 107.9, 79.1, 77.7, 76.6, 76.1, 71.8, 71.6, 62.3, 48.1, 36.8, 31.8, 29.66, 29.60, 29.5, 29.37, 29.32, 29.28, 29.26, 29.23, 28.9, 27.8, 27.1, 26.9, 26.4, 25.69, 25.64, 22.8, 22.6, 14.0, 13.7. MALDI-MS (positive mode, DHB): m/z 902.3 [M+Na]$^+$. Anal. Calcd for C$_{54}$H$_{103}$NO$_7$ (877.77): C, 73.84; H, 11.82; N, 1.59. Found: C, 73.97; H, 11.96; N, 1.67.

(b) The procedure of 1(c) above was followed using the product of (a) above to give

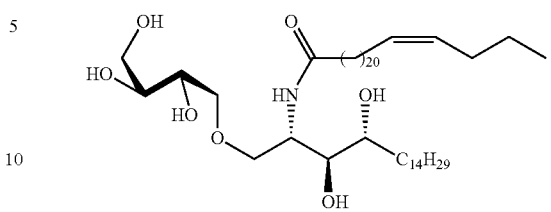

as a colourless solid, hereafter referred to as Compound 5 ('Threitol-22-(Z)-Ceramide') (yield: 81%). $^1$H NMR (250 MHz, C$_5$D$_5$N): δ 8.48 (d, J=8.7 Hz, 1H), 5.39-5.30 (m, 2H), 4.39-4.35 (m, 1H), 4.42-4.08 (m, 8H), 3.97-3.95 (m, 2H), 2.32 (t, J=7.5 Hz, 2H), 1.99-1.87 (m, 4H), 1.81-1.64 (m, 4H), 1.77-1.12 (m, 60H), 0.78-0.71 (m, 6H). MALDI-MS (positive mode, Matrix CHCA): m/z 820.8 [M+Na]. Anal. Calcd for C$_{48}$H$_{95}$NO$_7$ (797.71): C, 72.22; H, 12.00; N, 1.75: C, 72.29; H, 11.93; N, 1.80.

Compound 6: 4-Deoxy-4-Phenyl-Threitol-Ceramide (a) Compound

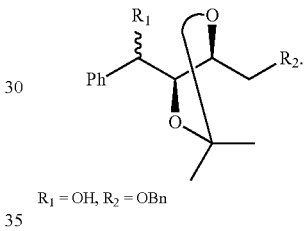

R$_1$ = OH, R$_2$ = OBn was prepared with well known procedures (see, Su, et al., Tetrahedron, 57:2147 (2001)); Surivet, et al., Tetrahedron Lett., 39:7299 (1998) and Surivet, et al., Tetrahedron, 55:1311 (1999)). The above compound (1 g, 3.048 mmol) in CH$_2$Cl$_2$ (20 mL) was treated with pyridine (1.48 mL, 18.291 mmol) and 4-dimethylamino pyridine (4-DMAP) (110 mg, 0.901 mmol) followed by phenoxythiocarbonyl chloride (0.630 mL, 4.56 mmol) at room temperature. After 30 min, the reaction mixture was diluted with CH$_2$Cl$_2$, washed with 10% NaHCO$_3$ solution, water, dried over MgSO$_4$ and co-evaporated with toluene to give residue. The crude product was dissolved in toluene (30 mL), tributyltin hydride (2.45 mL, 9.144 mmol) and AIBN (150 mg, 0.914 mmol) were added, and the reaction mixture was refluxed under argon atmosphere for 4 hours. Concentrated and purified by flash chromatography (1:9, ethyl acetate:petroleum ether) to give the reduction product

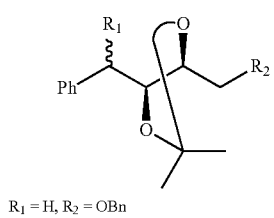

R$_1$ = H, R$_2$ = OBn as a colourless liquid (900 mg, 95% yield). R$_f$=0.40 (1:9, ethyl acetate:petroleum ether). [α]$_D^{25}$=−10.2 (c 1.0, CHCl$_3$). $^1$H NMR (250 MHz, CDCl$_3$): δ 7.31-7.13 (m, 10H), 3.99 (br. s, 2H), 4.01-3.93 (m, 2H), 3.87-3.80 (m, 2H), 3.31-3.18 (m, 2H), 2.92 (dd, 13.7, 6.5 Hz, 1H), 2.77 (dd, J=13.7, 6.5 Hz, 1H), 1.31 (s, 6H). $^{13}$C NMR (62.5 MHz, CDCl$_3$): δ 137.9, 137.2, 129.3, 128.2, 127.5, 126.4, 108.9, 79.6, 78.4, 76.4, 73.3, 70.3, 39.4, 27.1, 26.9. MALDI-MS (positive mode, CHCA): m/z 335.1 [M+Na].

(b) The product from (a) above (890 mg, 2.852 mmol) and 10% Pd/C (200 mg) in ethyl acetate:methanol (3:2, 20 mL), stirred under H$_2$ atmosphere (balloon) at room temperature for 8 and then the mixture was filtered, concentrated and purified by flash chromatography (2:8, ethyl acetate:petroleum ether) to obtain

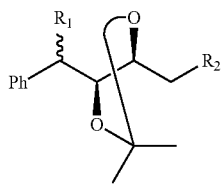

R$_1$ = H, R$_2$ = OH (608 mg, 96% yield). R$_f$=0.20 (2:8, ethyl acetate:petroleum ether). [α]$_D^{25}$=−19.0 (c 1.0, CHCl$_3$). $^1$H NMR (250 MHz, CDCl$_3$): δ 7.28-7.19 (m, 5H), 4.12 (dt, J=12.5, 8.2, 6.2 Hz, 1H), 3.80 (ddd, J=8.0, 4.7, 3.0 Hz, 1H), 3.51 (dd, J=12.0, 3.0 Hz, 1H), 3.28 (dd, J=12.0, 4.7 Hz, 1H), 3.04 (dd, J=14.0, 6.5 Hz, 1H), 2.82 (dd, J=14.0, 6.5 Hz, 1H), 1.40 (s, 6H). $^{13}$C NMR (62.5 MHz, CDCl$_3$): δ 136.9, 129.2, 128.4, 126.6, 108.7, 81.1, 77.06, 61.9, 39.3, 27.2, 27.0. MALDI-MS (positive mode, CHCA): m/z 345.0 [M+Na]$^+$.

(c) The product of (b) above, was converted into the triflate product using the method mentioned in procedure 1(a) above to give

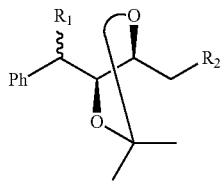

R$_1$ = H, R$_2$ = OTf as a colourless liquid (yield: 78%). [α]$_D^{25}$=−15.5 (c 1.0, CHCl$_3$). $^1$H NMR (250 MHz, CDCl$_3$): δ 7.32-7.19 (m, 5H), 4.23-4.08 (m, 2H), 4.01-3.91 (m, 2H), 3.16 (dd, J=13.5, 6.0 Hz, 1H), 2.81 (dd, J=13.5, 6.0 Hz, 1H), 1.42 (s, 3H), 1.39 (s, 3H). $^{13}$C NMR (62.5 MHz, CDCl$_3$): δ 211.4, 135.8, 129.1, 128.8, 127.2, 110.0, 77.7, 76.9, 74.5, 39.2, 27.2, 26.6.

(d) The procedure of 1(a) above was repeated using the product of (c) above to give

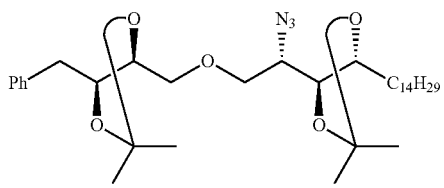

which was purified by flash chromatography (1:9, ethyl acetate:petroleum ether) as a colourless liquid (yield: 93%). R$_f$=0.42 (15:85, ethyl acetate:petroleum ether). [α]$_D^{25}$=+4.9 (c 1.0, CHCl$_3$). $^1$H NMR (250 MHz, CDCl$_3$): δ 7.30-7.22 (m, 5H), 4.13-4.05 (m, 2H), 3.92-3.80 (m, 3H), 3.61-3.53 (m, 2H), 3.45-3.34 (m, 2H), 3.03 (dd, J=14.0, 6.7 Hz, 1H), 2.88 (dd, J=14.0, 6.7 Hz, 1H), 1.53-1.24 (m, 26H), 1.37 (br. s, 12H), 0.86 (t, J=6.5 Hz, 3H). $^{13}$C NMR (62.5 MHz, CDCl$_3$): δ 137.3, 129.3, 128.3, 127.6, 126.5, 108.9, 108.2, 79.7, 78.2, 77.7, 75.6, 72.7, 71.9, 59.8, 39.5, 31.9, 29.67, 29.64, 29.58, 29.54, 29.4, 29.3, 28.1, 27.2, 26.9, 26.4, 25.6, 22.6, 14.1. MALDI-MS (positive mode, CHCA): m/z 610.9 [M+Na]$^+$.

(e) The procedure of 1(b) was repeated using the product of (d) above to give

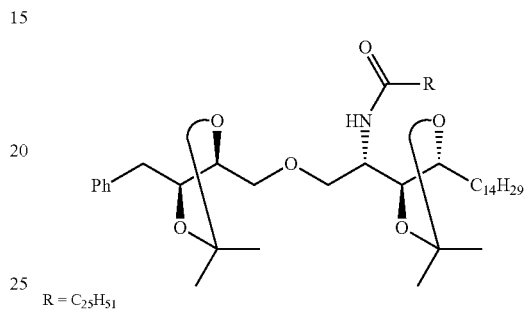

R = C$_{25}$H$_{51}$ which was purified by flash chromatography (15:85, ethyl acetate:petroleum ether) as a colourless solid (yield: 72%). R$_f$=0.35 (2:8, ethyl acetate:petroleum ether). [α]$_D^{25}$=+9.2 (c 1.0, CHCl$_3$). $^1$H NMR (250 MHz, CDCl$_3$): δ 7.31-7.23 (m, 5H), 5.70 (d, J=9.0 Hz, 1H), 4.19-4.00 (m, 4H), 3.95-3.88 (m, 1H), 3.71 (dd, J=9.7, 3.0 Hz, 1H), 3.46-3.33 (m, 3H), 3.03 (dd, J=14.0, 6.5 Hz, 1H), 2.88 (dd, J=14.0, 6.5 Hz, 1H), 2.14 (dt, J=10.5, 7.2, 2.7 Hz, 1H), 1.66-1.27 (m, 84H), 0.90 (t, J=6.5 Hz, 6H). $^{13}$C NMR (62.5 MHz, CDCl$_3$): δ 172.3, 137.2, 129.3, 128.3, 126.5, 109.0, 107.8, 79.7, 78.4, 77.7, 75.9, 72.1, 48.1, 39.6, 36.9, 31.9, 29.6, 29.5, 29.4, 29.35, 29.32, 29.0, 28.0, 27.3, 27.1, 26.4, 25.79, 25.72, 22.6, 14.1. MALDI-MS (positive mode, DHB): m/z 962.4 [M+Na]. Anal. Calcd for C$_{60}$H$_{109}$NO$_6$ (939.83): C, 76.62; H, 11.68; N, 1.49. Found: C, 76.70; H, 11.59; N, 1.53.

(f) The procedure of 1(c) was repeated using the product of (e) above to give

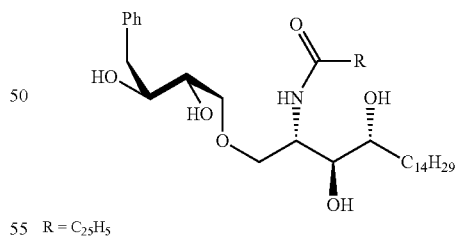

R = C$_{25}$H$_5$ as a colourless solid (yield: 70%), hereafter referred to as Compound 6 ('4-Deoxy-4-Phenyl-Threitol-Ceramide Analog'). $^1$H NMR (250 MHz, C$_5$D$_5$N): δ 8.46 (d, J=8.5 Hz, 1H), 7.37-7.13 (m, 5H), 4.22-4.04 (m, 7H), 3.94-3.92 (m, 2H), 3.17 (dd, J=14.0, 4.6 Hz, 1H), 3.03 (dd, J=14.0, 7.5 Hz, 1H), 2.31 (br. t, J=7.2 Hz, 2H), 1.73-1.70 (m, 4H), 1.19-1.13 (m, 68H), 0.74 (t, J=6.7 Hz, 6H). MALDI-MS (positive mode, DHB): m/z 882.9 [M+Na]$^+$. Anal. Calcd for C$_{54}$H$_{101}$NO$_6$ (859.76): C, 75.38; H, 11.83; N, 1.63. Found: C, 75.36; H, 12.03; N, 1.68.

Compound 7: 4-Deoxy-4-Phenyl-Threitol-22-(Z)-Ceramide
(a) The procedure of 1(b) was repeated using 22-(Z)-hexacosanoic acid and the product of 6(d) above e.g.

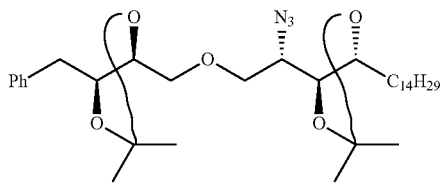

to give

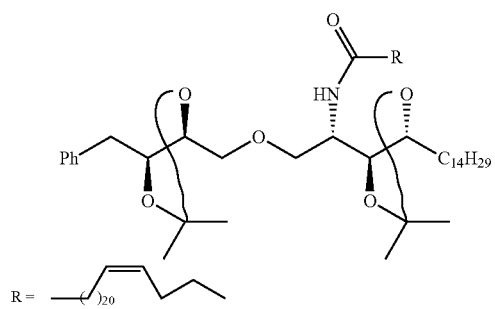

as a colourless solid (yield: 72%). R$_f$=0.38 (2:8, ethyl acetate: petroleum ether). [α]$_D^{25}$=+8.0 (c 1.0, CHCl$_3$). $^1$H NMR (250 MHz, CDCl$_3$): δ 7.31-7.22 (m, 5H), 5.66 (d, J=9.2 Hz, 1H), 5.36-5.31 (m, 2H), 4.12-3.98 (m, 4H), 3.91-3.84 (m, 1H), 3.67 (dd, J=10.0, 3.5 Hz, 1H), 3.43-3.28 (m, 3H), 2.99 (dd, J=14.0, 6.6 Hz, 1H), 2.84 (dd, J=14.0, 6.5 Hz, 1H), 2.00 (dt, J=10.5, 7.2, 2.7 Hz, 2H), 2.02-1.97 (m, 4H), 1.57-1.23 (m, 76H), 0.91-0.81 (m, 6H). $^{13}$C NMR (62.5 MHz, CDCl$_3$): δ 172.3, 137.2, 130.1, 129.5, 129.3, 128.4, 126.6, 109.0, 107.8, 79.7, 78.4, 77.7, 75.9, 72.2, 71.2, 48.1, 39.6, 36.9, 31.9, 29.76, 29.71, 29.5, 29.4, 29.36, 29.31, 29.2, 29.0, 28.0, 27.3, 27.2, 27.1, 26.4, 25.8, 25.7, 22.8, 22.6, 14.1, 13.8. MALDI-MS (positive mode, DRS): m/z 960.1 [M+Na]$^+$. Anal. Calcd for C$_{60}$H$_{107}$NO$_6$ (937.81): C, 76.79; H, 11.49; N, 1.49. Found: C, 76.86; H, 11.57; N, 1.55.

(b) The procedure of 1(c) was repeated using the product of (a) above to give

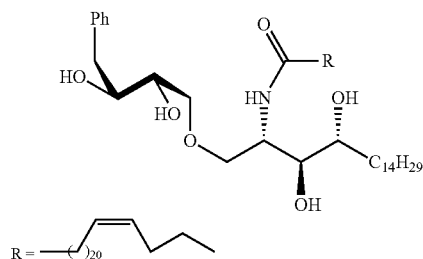

as a colourless solid hereafter referred to as Compound 7 ('4-Deoxy-4-Phenyl-Threitol-22-(Z)-Ceramide') (yield: 68%). $^1$H NMR (250 MHz, C$_5$D$_5$N): δ 8.46 (d, J=8.4 Hz, 1H), 7.37-7.13 (m, 5H), 5.41-5.25 (m, 2H), 4.22-4.05 (m, 7H), 3.94-3.92 (m, 2H), 3.17 (dd, J=14.0, 4.6 Hz, 1H), 3.05 (dd, J=14.0, 7.5 Hz, 1H), 2.31 (br. t, J=7.2 Hz, 2H), 1.99-1.87 (m, 4H), 1.80-1.64 (m, 4H), 1.17-1.13 (m, 60H), 0.79-0.71 (m, 6H). MALDI-MS (positive mode, DHB): m/z 881.1 [M+Na]$^+$. Anal. Calcd for C$_{54}$H$_{99}$NO$_6$ (857.75): C, 75.56; H, 11.63; N, 1.63. Found: C, 75.47; H, 11.58; N, 1.68.

Compound 8: D-Glycerol-phosphate Ceramide
(a) A solution of

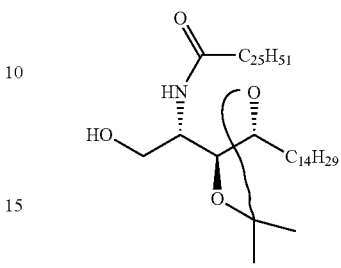

(150 mg, 0.204 mmol) in CH$_2$Cl$_2$ (4 mL), was prepared as described by Mayer, et al., *Angew. Chem.*, 106:2289 (1994); *Angew. Chem., Int. Ed.*, 33:2177 (1994) and Kratzer, et al., *Eur. J. Org. Chem.*, 291 (1998), and combined with 0.45 M solution of tetrazole in acetonitrile (1.16 mL, 0.50 mmol) at room temperature. After being stirred for 10 minutes, a solution of compound

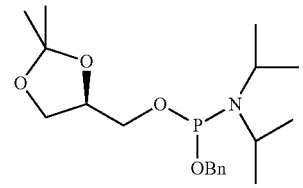

as described by Chen, et al., *J. Org. Chem.*, 63:6511 (1998), (97 mg, 0.265 mmol), in dry CH$_2$Cl$_2$ (3 mL) was added at the same temperature. The reaction mixture was stirred for 2.5 hours, and then t-Butyl hydroperoxide (0.26 mL, 0.266 mmol) was added to the reaction mixture. The reaction mixture was further stirred for 15 minutes and the mixture was extracted with CH$_2$Cl$_2$ and water, the organic layer was washed with saturated NaHCO$_3$ and brine, dried aver anhydrous MgSO$_4$. The solvent was evaporated to give crude material, which was purified by flash chromatography (4:6, ethyl acetate:petroleum ether) to give pure

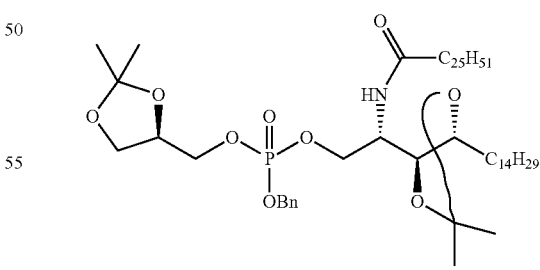

as a colorless solid (191 mg, 92%) mp 87° C. R$_f$ 0.40 (6:4, ethyl acetate:petroleum ether). [α]$_D^{25}$=+4.0 (c 1.0, CHCl$_3$). $^1$H NMR (400 MHz, CDCl$_3$, mixture of diastereomers): δ 7.36-7.32 (m, 5H), 6.01 (d, J=8.9 Hz, 1H), 5.89 (d, J=9.3 Hz, 1H), 5.07 (d, J=8.5 Hz, 2H), 5.04 (d, J=8.6 Hz, 2H), 4.29-4.19 (m, 3H), 4.10-3.86 (m, 6H), 3.76-3.69 (m, 1H), 2.11-2.03 (m, 2H), 1.55-1.18 (m, 72H), 1.38 (s, 6H), 1.37 (s, 3H), 1.36 (s, 3H), 1.31 (s, 6H), 1.28 (s, 3H), 1.27 (s, 3H), 0.85 (t, J=6.6 Hz, 61-1). $^{13}$C NMR (100 MHz, CDCl$_3$): δ 172.64, 172.61, 135.6, 135.5, 128.6-127.7 (m), 109.9, 108.0, 77.5, 75.3, 73.9, 65.9, 48.2, 36.7, 31.9, 29.6, 29.5, 29.3, 27.8, 26.5, 25.5, 25.1, 22.6, 14.1. $^{31}$P NMR (162 MHz, CDCl$_3$): δ 0.1, 0.04. MALDI-MS (positive mode, Matrix CHCA): m/z 1043.2 [M+Na]$^+$. Anal. Calcd for C$_{60}$H$_{110}$NO$_9$P (1019.79): C, 70.62; H, 10.86; N, 1.37. Found: C, 70.66; H, 10.94; N, 1.41.

(b) The product of (a) above (160 mg, 0.157 mmol) and 10% Pd/C (50 mg) in methanol (8 mL) was stirred under H$_2$ atmosphere at room temperature for 1 hour. To this reaction mixture triethyl amine (26 µL, 0.188 mmol) was added, and after being stirred for 15 minutes, it was filtered through celite and evaporated to give crude material which was submitted to subsequent reaction without any further purification. The resulting compound

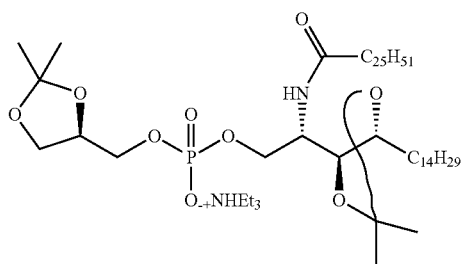

was dissolved in MeOH/CH$_2$Cl$_2$ (10:1, 22 mL) containing TFA (150 µL), and was stirred at room temperature for 3 days. The solvent was evaporated to give a solid. The solid was filtered and washed thoroughly with ethyl acetate and CH$_2$Cl$_2$ (to remove soluble organic material). This solid was dissolved in dioxane (1 mL), a few drops MeOH and triethyl amine where added (26 µL, 0.188 mmol) with heating to 60° C. This mixture was lyophilized to give unprotected target molecule

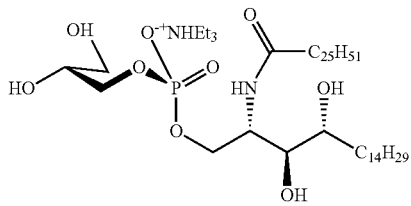

hereinafter referred to as Compound 8 ('D-Glycerol-phosphate Ceramide'); as a colorless solid (97 mg, 60%). $^1$H NMR (250 MHz, C$_5$D$_5$N): δ 9.09 (d, J=8.5 Hz, 1H), 5.24-5.09 (m, 2H), 4.96-4.90 (m, 1H), 4.80-4.75 (m, 2H), 4.60-4.52 (m, 2H), 4.44-4.40 (m, 1H), 4.28 (br. d, J=5.5 Hz, 2H), 3.10 (q, J=7.5 Hz, 6H), 2.60 (t, J=6.7 Hz, 2H), 2.05-1.32 (m, 81H), 0.97-0.95 (m, 6H). $^{13}$C NMR (150.9 MHz, C$_5$D$_5$N): δ 173.4, 75.5, 72.67, 72.65, 72.5, 68.3, 65.94, 65.92, 65.8, 45.7, 36.8, 33.3, 32.1, 30.3, 30.2, 30.0, 29.8, 29.6, 29.2, 6.4, 22.9, 14.2. $^{31}$P NMR (162 MHz, C$_5$D$_5$N): δ 3.0. MALDI-MS (negative mode, Matrix ATT): m/z 929.1 [M-HNEt$_3$)]$^-$. Anal. Calcd for C$_{59}$H$_{119}$NO$_9$P (1031.86): C, 68.70; H, 11.63; N, 2.72. Found: C, 68.75; H, 10.99; N, 2.79.

Compound 9: L-Glycerol-phosphate Ceramide

The procedure described in 8(a) above was followed using isomer

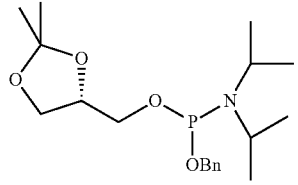

to give a crude material which was purified by flash chromatography (4:6, ethyl acetate:petroleum ether) to give pure

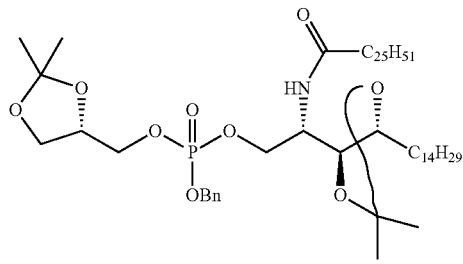

as a colorless solid (195 mg, 94%) mp 85° C. R$_f$ 0.47 (6:4, ethyl acetate:petroleum ether). [α]$_D^{25}$=2.5 (c 1.0, CHCl$_3$). $^1$H NMR (400 MHz, CDCl$_3$, mixture of diastereomers): δ 7.40-7.30 (m, 5H), 6.05 (d, J=9.1 Hz, 1H), 5.99 (d, J=9.2 Hz, 1H), 4.32-4.20 (m, 3H), 4.13-3.93 (m, 6H), 3.75 (br. dd, J=8.8, 5.6 Hz, 1H), 2.20-2.09 (m, 2H), 1.58-1.13 (m, 72H), 1.38 (s, 6H), 1.34 (s, 3H), 1.35 (s, 3H), 1.31 (s, 6H), 1.29 (s, 3H), 1.25 (s, 3H), 0.93 (1, J=6.6 Hz, 6H). $^{13}$C NMR (100 MHz, CDCl$_3$): δ 172.64, 172.61, 135.6, 135.5, 128.6-127.7 (m), 109.9, 108.0, 108.0, 77.65, 77.63, 75.46, 75.43, 73.9, 73.8, 65.9, 48.2, 36.7, 31.9, 29.6, 29.5, 29.3, 28.9, 27.9, 27.8, 26.6, 26.5, 25.5, 25.1, 22.6, 14.1. $^{31}$P NMR (162 MHz, CDCl$_3$): δ 0.3, 0.2. MALDI-MS (positive mode, Matrix CHCA): m/z 1043.2 [M+Na]$^+$. Anal. Calcd for C$_{60}$H$_{110}$NO$_9$P (1019.79): C, 70.62; H, 10.86; N, 1.37. Found: C, 70.69; H, 10.98; N, 1.47.

(b) The procedure described for in 8(a) above was used to give

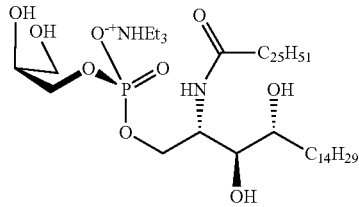

hereinafter referred to as Compound 9 ('L-Glycerol-phosphate Ceramide'); as a colorless solid (83 mg, 55%). $^1$H NMR (250 MHz, C$_5$D$_5$N): δ 9.09 (d, J=8.4 Hz, 1H), 4.87-4.65 (m, 5H), 4.59-4.33 (m, 3H), 4.28 (br. d, J=5.0 Hz, 2H), 3.10 (q, J=7.5 Hz, 6H), 2.63 (t, J=6.7 Hz, 2H), 2.05-1.37 (m, 81H), 0.99-0.96 (m, 6H). $^{13}$C NMR (150.9 MHz, C$_5$D$_5$N): δ 173.4, 75.6, 72.65, 72.5, 68.4, 65.96, 65.7, 46.0, 36.9, 33.4, 32.1, 31.6, 31.2, 31.0, 29.8, 29.6, 29.2, 26.4, 22.9, 14.2. $^{31}$P NMR (162 MHz, C$_5$D$_5$N): δ 3.6. MALDI-MS (negative mode, Matrix ATT): m/z 929.1 [M-HNEt$_3$)]$^-$. Anal. Calcd for C$_{59}$H$_{119}$NO$_9$P (1031.86): C, 68.70; H, 11.63; N, 2.72. Found: C, 68.79; H, 10.95; N, 2.78.

Compound 10: Inositol ceramide (a) A stirred solution of (366 mg, 0.691 mmol) of compound

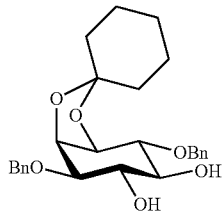

obtained in accordance with well known procedures, see Mayer, et al., *Liebigs Ann./Recueil*, 859 (1997) and Jiang, et al., *J. Carbohydr. Chem.*, 6:319 (1987), was mixed, with 2,6-di-tert-butylpyridine (159 mg, 0.83 mmol) in anhydrous $CH_2Cl_2$ (3 ml) and $Tf_2O$ (136 µl, 0.83 mmol) which was dissolved in 2 ml of $CH_2Cl_2$, at 0° C. The reaction mixture was stirred at the same temperature for 3 hours. The reaction mixture was taken in ethyl acetate and washed with cold water (2×25 mL). The combined organic layers were washed with brine, dried and evaporated to get the crude product which was purified by flash chromatography (8:92 ethyl acetate:petroleum ether containing drops of $Et_3N$) to give (413 mg, 90%) of

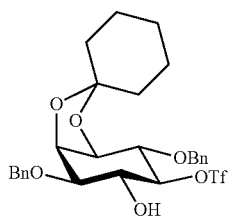

Rf 0.41 (1:9, ethyl acetate:petroleum ether). $^1H$ NMR (250 MHz, $CDCl_3$): δ 7.41-7.28 (m, 15H), 4.88 (d, J=11.9 Hz, 1H), 4.78-4.67 (m, 5H), 4.30 (dd, J=6.0, 3.7 Hz, 1H), 4.17 (t, J=6.4 Hz, 1H), 4.03 (t, J=7.6 Hz, 1H), 3.97 (dd, J=9.1, 6.5 Hz, 1H), 3.77 (dd, J=8.0, 3.6 Hz, 1H), 1.83-1.30 (m, 10H). $^{13}C$ NMR (62.5 MHz, $CDCl_3$): δ 137.6, 137.32, 137.29, 128.4, 128.3, 128.2, 128.1, 128.0, 127.9, 127.7, 111.1, 87.7, 79.0, 77.83, 77.77, 76.4, 74.6, 73.6, 73.3, 37.0, 34.5, 25.0, 23.9, 23.6.

(b) The procedure of 1(a) above was repeated using a solution of NaH (60%, 7 mg, 0.181 mmol), 58 mg (0.151 mmol) of sphingosine component i.e.

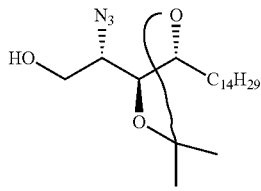

in 1 ml of anhydrous DMF. After thirty minutes of stirring, a solution of the product of (a) above, (100 mg, 0.151 mmol) in anhydrous DMF (1.5 ml), was added, at this same temperature. After stirring overnight, the reaction mixture was quenched by adding an aqueous solution of $NH_4Cl$. It was taken in EtOAc and the layers were separated. The organic layer was washed with water, dried over anhydrous $MgSO_4$ and evaporated to dryness. The crude material was purified by flash chromatography (1:9, ethyl acetate:petroleum ether) to give the pure compound

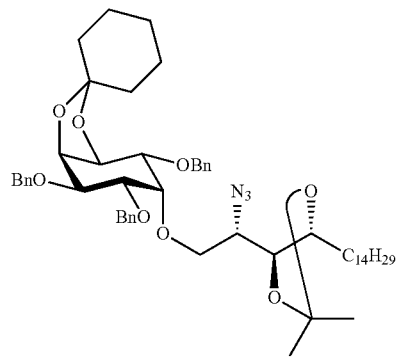

as a colorless liquid (108 mg, 80%), $R_f$=0.44 (1:9, ethyl acetate:petroleum ether). $^1H$ NMR (250 MHz, $CDCl_3$): δ 7.45-7.23 (m, 15H), 4.88-4.63 (m, 6H), 4.30-3.83 (m, 8H), 3.75-3.69 (m, 1H), 3.56-3.47 (m, 1H), 3.40-3.35 (m, 1H), 1.72-1.26 (m, 36H), 1.37 (s, 3H), 1.35 (s, 3H), 0.88 (t, J=7.2 Hz, 3H). $^{13}C$ NMR (62.5 MHz, $CDCl_3$): δ 139.0, 138.8, 138.7, 138.6, 138.4, 138.3, 128.3, 128.22, 128.18, 128.1, 128.0, 127.59, 127.55, 127.5, 127.4, 127.3, 109.7, 108.0, 79.2, 79.1, 78.9, 78.8, 78.7, 78.0, 77.9, 77.8, 77.2, 76.25, 76.20, 75.4, 75.3, 74.2, 73.9, 73.7, 73.4, 73.3, 73.13, 73.09, 71.7, 71.5, 60.22, 60.16, 37.9, 35.3, 31.9, 29.64, 29.61, 29.5, 29.3, 28.13, 28.10, 26.4, 25.7, 25.1, 24.0, 23.5, 22.6, 14.0. MALDI-MS (positive mode, DHB): m/z 919.8 [M Na]$^+$. Anal. Calcd for $C_{54}H_{77}N_3O_8$ (896.20): C, 72.37; H, 8.66; N, 4.69. Found: C, 71.91; H, 8.36; N, 4.68.

(c) The product of (b) above 160 mg (0.178 mmol), and a pinch of $Pd(OH)_2/C$ in $MeOH/CH_2Cl_2/H_2O$ (7.5:7.5:1, 3 mL) was stirred under $H_2$ atmosphere at room temperature overnight. Then the mixture was filtered, concentrated and co-evaporated with toluene. The resulting syrup was dissolved in dry DMF (4 mL). Hexacosonoic acid (71 mg, 0.178 mmol), N-hydroxybenzotriazole (24 mg, 0.178 mmol) and 1-[3-(dimethylamino)-propyl]-3-ethylcarbodiimide hydrochloride (34 mg, 0.178 mmol) were added successively and the resulting mixture was stirred at 45° C. for 1 day. Then it was taken in ethyl acetate washed with water, saturated brine solution, dried over anhydrous $MgSO_4$, and concentrated. The residue was purified by flash column chromatography (7:3, ethyl acetate:petroleum ether) to give the compound

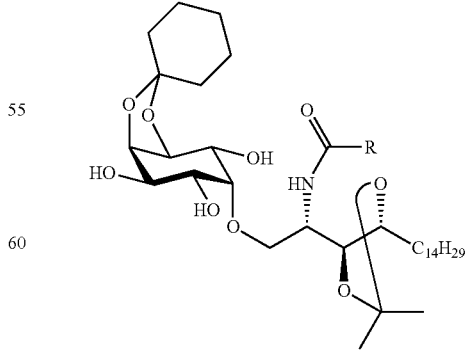

$R = C_{25}H_{51}$ (75 mg, 43%). $R_f$=0.23 (7.5:2.5, ethyl acetate:petroleum ether). $^1$H NMR (250 MHz, CDCl$_1$): δ 6.09 (t, J=9.5 Hz, 1H), 4.47-4.40 (m, 1H), 4.27-3.68 (m, 10H), 2.36-111 (m, 2H), 1.72-1.18 (m, 82H), 1.44 (s, 3H), 1.34 (s, 3H), 0.88 (t, J=6.4 Hz, 6H). MALDI-MS (positive mode, DHB): 1002.0 [M+Na]$^+$. Anal. Calcd for $C_{59}H_{111}NO_9$ (978.51): C, 72.42; H, 11.43; N, 1.43. Found: C, 72.16; H, 11.46; N, 1.36.

(d) A solution of the product (c) above (46 mg, 0.047 mmol), in MeOH/CH$_2$Cl$_2$ (1:1, 2 ml), with a few crystals of CSA were stirred, at room temperature, for 2 days. The solid thrown out was dried to give 22 mg of the compound

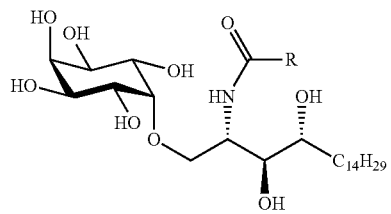

R = C$_{25}$H$_{51}$ hereinafter referred to as Compound 10 ('inositol-ceramide'); (55% yield). $^1$H NMR (250 MHz, C$_5$D$_5$N): δ 5.20-4.15 (m, 11H), 2.49-2.38 (m, 2H), 2.38-1.10 (m, 72H), 0.91-0.80 (m, 6H). MALDI-MS (positive mode, DHB): m/z 881.6 [M+Na]$^+$. Anal. Calcd for $C_{50}H_{99}NO_9$ (858.32): C, 69.97; H, 11.63; N, 1.63. Found: C, 70.07; H, 11.70; N, 1.67.

Compound 11: Inositol ceramide C$_{15}$ acyl (a) The product of 10(b) (114 mg (0.127 mmol) e.g.

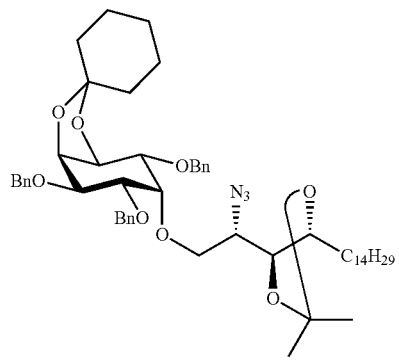

was combined with 10% Pd/C (100 ng) in MeOH/CH$_2$Cl$_2$/H$_2$O (7.5:7.5:1, 3 mL) and stirred under an H$_2$ atmosphere at room temperature overnight. Then the mixture was filtered, concentrated and co-evaporated with toluene. The resulting syrup was dissolved in dry DMF (4 mL). Palmitic acid (33 mg, 0.127 mmol), N-hydroxybenzotriazole (17 mg, 0.127 mmol) and 1-[3-(dimethylamino)-propyl]-3-ethylcarbodiimide hydrochloride (24 mg, 0.127 mmol) were added successively and the resulting mixture was stirred at 45° C. for 1 day. Then it was taken in ethyl acetate washed with water, saturated brine solution, dried over anhydrous MgSO$_4$, and concentrated. The residue was purified by flash chromatography (7:3, ethyl acetate:petroleum ether) to give

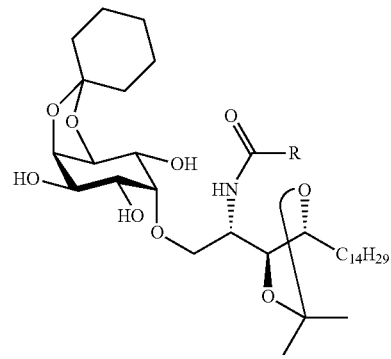

R = C$_{15}$H$_{31}$ (48 mg, 45%). Rf=0.24 (3:4, ethyl acetate:petroleum ether). $^1$H NMR (250 MHz, CDCl$_3$): δ 6.05 (t, J=9.3 Hz, 1H), 4.47-4.39 (m, 1H), 4.27-3.67 (m, 10H), 2.28-2.13 (, 2H), 1.72-1.20 (m, 62H), 1.44 (s, 3H), 1.34 (s, 3H), 0.88 (t, J=6.4 Hz, 6H). MALDI-MS (positive mode, DHB): 861.7 [M+Na]$^+$. Anal. Calcd for $C_{49}H_{91}NO_9$ (838.24): C, 70.11; H, 10.94; N, 1.67. Found: C, 70.19; H, 11.03; N, 1.69.

(b) The product of (a) above (44 mg, 0.047 mmol) in MeOH:CH$_2$Cl$_2$ (1:12 ml) containing a few crystals of CSA was stirred at room temperature for 36 hours. The solid thrown out was filtered and dried to give

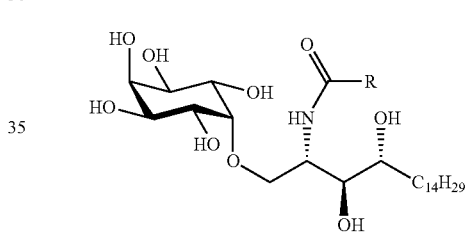

R = C$_{15}$H$_{31}$ hereinafter referred to as Compound 11 ('inositol-ceramide C$_{15}$ acyl'); (19 mg, 50%). $^1$H NMR (250 MHz, C$_5$D$_5$N): δ 5.35-4.25 (m, 11H), 2.48-2.37 (m, 2H), 2.37-1.10 (m, 52H), 0.90-0.78 (m, 6H). MALDI-MS (positive mode, DHB): 741.2 [M+Na]$^+$. Anal. Calcd for $C_{40}H_{79}NO_9$ (718.05): C, 66.91; H, 11.09; N, 1.95. Found: C, 66.98; H, 11.47; N, 1.39.

Compound 12: D-myo-Inositol Ceramide (a) Compound

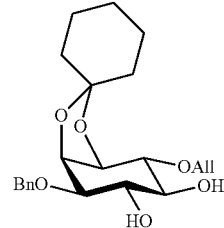

was prepared with well known procedures, see Stadelmaier, et al., *Carbohydr. Res.*, 338:2557 (2003). The above compound (2.66 g, 6.820 mmol) in dry toluene (25 mL), was treated with NaH (95% in mineral oil, 200 mg, 8.333 mmol), benzyl bromide (900 µL, 7.578 mmol). The reaction mixture was refluxed for 10 hours. The reaction mixture was cooled room temperature, and diluted with ethyl acetate, washed with water, dried over MgSO4 and evaporated to give residue, which was purified by flash chromatography (15:85, ethyl acetate:petroleum ether) from a mixture of isomers (~1:1.4) (75% yield) to give

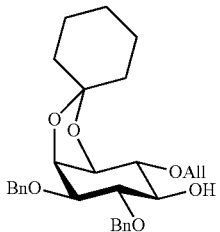

$R_f$=0.32 (15:85, ethyl acetate:petroleum ether). $^1$H NMR (600 MHz, CDCl$_3$): δ 7.37-7.28 (m, 10H), 5.96-5.90 (m, 1H), 5.29 (dd, J=17.4, 1.8 Hz, 1H), 5.18 (dd, J 10.8, 1.8 Hz, 1H), 4.87 (d, J=11.4 Hz, 1H, benzyl-H)), 4.76-4.71 (m, 3H, benzyl-H), 4.38-4.36 (m, 1H, allyl-H), 4.29 (dd, J=6.0, 4.2 Hz, 1H, H-4), 4.23-4.21 (m, 1H, allyl-H), 4.01 (dd, J=7.2, 6.0 Hz, 1H, H-5), 3.79 (t, =8.1 Hz, 1H, H-2), 3.68 (dd, J=8.1, 3.9 Hz, 1H, H-3), 3.59 (dd, J=9.6, 7.2 Hz, 1H, H-6), 3.44 (dd, J=9.6, 8.1 Hz, 1H, H-1), 2.32 (br. s, 1H, —OH), 1.80-1.41 (m, 10H). $^{13}$C NMR (150 MHz, CDCl$_3$): δ 138.5, 138.1, 135.0, 128.59, 128.57, 128.47, 128.43, 128.0, 127.98, 127.94, 127.8, 127.7, 117.2, 110.4, 81.4 (C-6), 80.6 (C-2), 78.4 (C-5), 77.4 (C-3), 74.6, 74.0 (C-4), 73.3 (C-1), 72.8, 72.2, 37.3, 35.0, 25.0, 23.9, 23.6. MALDI-MS (positive mode, DHB): m/z, 503.5 [M Na]$^+$.

(b) The procedures of 1(a) and 1(b) were repeated using the product of (a) above to give

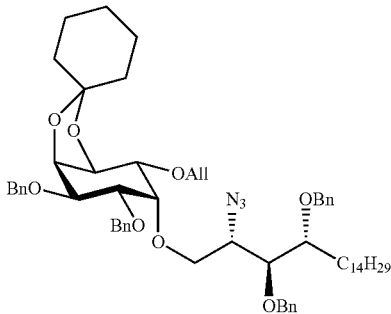

which was purified by flash chromatography (5:95, ethyl acetate:petroleum ether), (yield: 87%). $R_f$=0.54 (1:9, ethyl acetate:petroleum ether). $[α]_D^{25}$=+1.4 (c 1.0, CHCl$_3$). $^1$H NMR (600 MHz, CDCl$_3$): δ 7.39-7.23 (m, 20H), 5.96-5.90 (m, 1H), 5.20 (dd, J=17.4, 1.8, Hz, 1H), 5.10 (dd, J=10.8, 1.8 Hz, 111), 4.84-4.81 (m, 2H, benzyl-H), 4.72 (d, J=12.0 Hz, 1H, benzyl-H), 4.68-4.64 (m, 2H, benzyl-H), 4.59-4.54 (m, 2H, benzyl-H), 4.46 (d, J=11.4 Hz, 1H, benzyl-H), 4.26 (t, J=4.8 Hz, 1H, H-4), 4.19-4.16 (m, 3H, H-5, allyl-H), 4.14-4.06 (m, 2H, H-1', allyl-H), 3.99-3.96 (m, 1H, H-1'), 3.81 (d, J=1.8 Hz, 1H, H-1), 3.75 (dd, J=9.6, 1.8 Hz, 1H, H-2), 3.72-3.70 (m, 1H, H-2), 3.58-3.56 (m, 2H, H-3', H-4'), 3.33 (dd, J=8.4, 2.4 Hz, 1H, H-6), 1.61-1.41 (m, 10H), 1.26-1.24 (m, 26H), 0.88 (t, J=7.2 Hz, 1H, 3H). $^{13}$C NMR (150 MHz, CDCl$_3$): δ 138.5-127.4 (m, 24C), 135.1, 116.8, 109.7, 79.6 (C-4'), 79.1 (C-1, C-6), 78.8 (C-2), 78.7 (C-3'), 78.0 (C-5), 76.3 (C-3), 73.8 (C-4), 73.6, 73.5 (C-1'), 73.3, 71.9, 70.9, 62.4 (C-2'), 37.5, 35.0, 25.0, 23.9, 23.6, 22.7, 14.1. MALDI-MS (positive mode, DHB): m/z 1009.1 [M+Na]$^+$. Anal. Calcd for C$_{61}$H$_{83}$N$_3$O$_8$ (985.62): C, 74.28; H, 8.48; N, 4.26. Found: C, 74.19; H, 8.42; N, 4.28.

(c) The product of (b) above (700 mg, 0.710 mmol) in a mixture of toluene/ethanol/1 M aq. HCl (3:6:1, 15 mL) was heated at 60° C. for 3 hours. The solvent was co-evaporated with toluene, dried in vacuo, the residue was dissolved in dry DMF (10 mL), NaH (60% mineral oil, 85 mg, 3.553 mmol) was added and stirred for 30 minutes, at room temperature, and then benzyl bromide (220 μL, 1.77 mmol) was added. The reaction mixture was stirred another 5 hours, and then extracted with diethyl ether (2×20 mL), the ether layer was washed with and water, dried over MgSO$_4$ and evaporated to give crude material, which was purified by flash chromatography (5:95, ethyl acetate:petroleum ether) to give

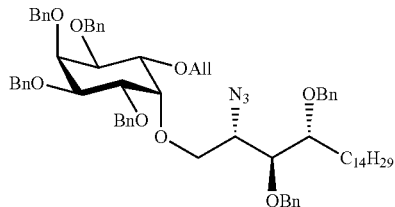

(655 mg, 85% yield). $R_f$=0.40 (5:95, ethyl acetate:petroleum ether). $[α]_D^{25}$=+2.8 (c 1.0, CHCl$_3$). $^1$H NMR (600 MHz, CDCl$_3$): δ 7.44-7.28 (m, 30H), 5.96-5.90 (m, 1H), 5.32 (dd, J=17.4, 1.8 Hz, 1H), 5.14 (dd, J=10.8, 1.8 Hz, 1H), 4.88-4.62 (m, 11H), 4.54 (d, J=11.4 Hz, 1H), 4.29-4.27 (m, 1H), 4.22-4.12 (m, 3H), 4.08 (br. s, 1H), 3.96 (br. s, 3H), 3.87-3.83 (m, 3H), 3.68-3.66 (m, 2H), 1.49-1.32 (m, 26H), 0.94 (t, J=7.2 Hz, 3H). $^{13}$C NMR (1.50 MHz, CDCl$_3$): δ 138.5-127.2 (m, 36C), 135.4, 116.2, 79.8, 79.2, 79.0, 78.9, 78.7, 78.38, 78.36, 76.0, 74.6, 74.4, 73.8, 73.17, 73.15, 73.0, 72.18, 72.10, 62.5, 32.0, 29.9, 29.89, 29.80, 29.79, 29.76, 29.4, 27.0, 25.7, 22.7, 14.2. MALDI-MS (positive mode, DHB): m/z 1110.4 [M+Na]$^+$. Anal. Calcd for C$_{69}$H$_{57}$N$_3$O$_8$ (1085.65): C, 76.28; H, 8.07; N, 3.87. Found: C, 76.36; H, 8.17; N, 3.95.

(d) The product of (c) above (650 mg, 0.598 mmol) in diethyl ether (5 mL) was added to a suspension of LiAlH$_4$ (46 mg, 1.210 mmol) in diethyl ether (10 mL) at 0° C. dropwise. The reaction mixture was slowly brought to the room temperature and refluxed for 1 hour. The reaction mixture was quenched with methanol and extracted with ethyl acetate (2×15 mL) and Water. The organic layer was washed with brine and dried over MgSO$_4$. Removal of the solvent gave a crude amine. The procedure in 1(b) above was repeated for the coupling of this amine to the carboxylic acid to give

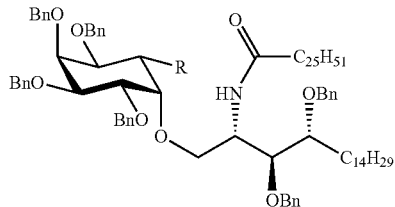

R = OAll (yield: 65%). $R_f$=0.57 (15:85, ethyl acetate:petroleum ether). $[α]_D^{25}$=+1.6 (c 1.0, CHCl$_3$). NMR (600 MHz, CDCl$_3$): δ 7.37-7.17 (m, 30H), 7.04 (d, J=8.6 Hz, 1H), 5.96-5.91 (m, 1H), 5.27 (dd, J=17.4, 1.8 Hz, 1H), 5.15 (dd, J=10.8, 1.8 Hz, 1H), 4.83-4.43 (m, 13H, benzyl-H, H-1'), 4.33-4.31 (m, 1H), 4.23-4.21 (m, 1H), 4.19-4.02 (m, 2H, H-4, H-2'), 3.91 (dd, J=9.6, 2.4 Hz, H-2), 3.88-382 (m, 3H, H-3', H-6, H-1), 3.73 (dd, =9.6, 3.0 Hz, 1H, H-3), 3.70 (dd, J=10.2, 2.4 Hz, 1H, H-5), 3.66-3.62 (m, 1H, H-1'), 3.48-3.44 (m, 1H, H-4'), 2.21-2.17 (m, 2H), 1.57-1.27 (m, 72H), 0.91 (t, J=7.2 Hz, 6H). $^{13}$C NMR (150 MHz, CDCl$_3$): δ 172.8, 139.2-1272 (m, 36C), 135.1, 117.1, 80.8 (C-4'), 80.0 (C-1), 79.6 (C-3), 79.44 (C-2), 79.41, 79.3 (C-5, C-6), 78.2 (C-3'), 75.3 (C-4), 74.6, 74.4, 73.8, 73.8 (C-1'), 73.6, 73.1, 72.8, 72.7, 71.6, 51.0 (C-2'), 36.8, 32.0, 29.9, 29.79, 29.77, 29.72, 29.6, 29.44, 29.43, 26.4, 25.9, 25.8, 22.7, 14.1. MALDI-MS (positive mode, DHB): m/z 1464.2 [M+Na]$^+$. Anal. Calcd for C$_{95}$H$_{139}$NO$_9$ (1438.04): C, 79.29; 9.74; N, 0.97. Found: C, 79.35; H, 9.81; N, 1.09.

(e) The compound of (d) above (650 mg, 0.452 mmol) as a solution in ethanol (15 mL), was treated with DBU (10 µL, 0.065 mmol), and tris(triphenylphospine) ruthenium (H) chloride (130 mg, 0.135 mmol). The reaction mixture was heated to reflux at 90° C. for 30 minutes. The solvent was evaporated to give isomerized product (R$_f$=0.54, 15:85, ethyl acetate:petroleum ether), which was dissolved in 1 M aq. HCl in acetone (1:9, 15 ml) and the reaction mixture was heated to reflux at 70° C. for 15 minutes. The mixture was cooled to room temperature, neutralized with Et$_3$N and extracted with ethyl acetate (2×20 mL), the organic phase was washed with water and brine, dried over MgSO$_4$ and evaporated to give crude material. Purified by flash chromatography (18:82, ethyl acetate:petroleum ether) to give

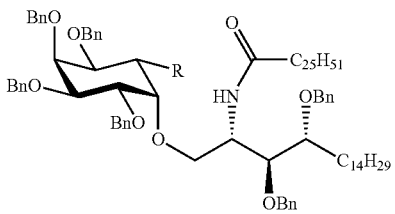

R = OH (655 mg, 78% yield). R$_f$=0.2 (15:85, ethyl acetate:petroleum ether). [α]$_D^{25}$=-6.4 (c 1.0, CHCl$_3$). $^1$H NMR (600 MHz, CDCl$_3$): δ 7.37-7.23 (m, 30H), 7.16 (d, J=8.7 Hz, 1H), 4.88 (d, J=12.0 Hz, 1H), 4.78-4.68 (m, 5H), 4.59-4.54 (m, 4H), 4.47-4.42 (m, 3H), 4.09-4.06 (m, 3H), 3.95-3.93 (m, 2H), 3.76-3.3.73 (m, 2H), 3.66 (br. d, J=8.4 Hz, 1H), 3.51-3.46 (m, 2H), 1.97-2.14 (m, 2H), 1.52-1.24 (m, 72H), 0.89 (t, J=7.2 Hz, 6H). $^{13}$C NMR (150 MHz, CDCl$_3$): δ 172.9, 138.9-127.3 (m, 36C), 80.7, 80.3, 79.9, 79.3, 79.1, 74.4, 74.2, 74.0, 73.9, 73.5, 73.3, 72.0, 71.7, 70.2, 51.9, 36.9, 31.9, 29.9, 29.77, 29.75, 29.70, 29.5, 29.42, 29.4, 26.3, 25.8, 22.7, 14.1. MALDI-MS (positive mode, DHB): m/z 1424.7 [M+Na]$^+$. Anal. Calcd for C$_{92}$H$_{135}$NO$_9$ (1398.01): C, 78.98; H, 9.73; N, 1.00. Found: C, 79.08; H, 9.84; N, 1.13.

(f) The procedure of 6(a) for reducing an OH group was repeated using the product of (e) above to give

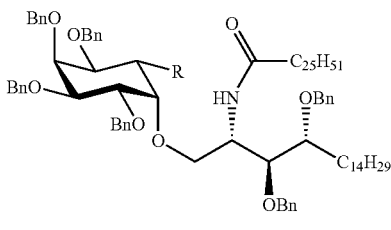

R = H which was purified by flash chromatography (2:98 ethyl acetate:toluene) as colourless solid (60%). R$_f$=0.57 (4:96, ethyl acetate:toluene). [α]$_D^{25}$=+11.2 (c 1.0, CHCl$_3$). $^1$H NMR (600 MHz, CDCl$_3$): δ 7.38-7.17 (m, 30H), 6.36 (d, J=8.6 Hz, 1H, —NH), 4.83-4.36 (m, 12H, benzyl-H), 4.18-4.14 (m, 2H, H-2', H-4), 4.00 (br. d, J=9.0 Hz, 1H, H-1'), 3.93 (dd, J=10.0, 3.0 Hz, 1H), H-2), 3.84 (t, J=4.0 Hz, 1H, H-3'), 3.78 (d, J=3.0 Hz, 1H, H-1), 3.76 (br. t, J=9.0 Hz, 1H, H-5), 3.72 (dd, J=10.0, 2.0 Hz, 1H, H-3), 3.66 (br. d, J=9.0 Hz, 1H, H-1'), 3.51 (ddd, J=12.0, 8.0, 4.0 Hz, 1H, H-4'), 1.98-1.94 (m, 1H, H-6), 1.82-1.72 (m, 2H), 1.63-1.61 (m, 1H, H-6), 1.43-1.24 (m, 72H), 0.86 (t, J=6.5 Hz, 6H). $^{13}$C NMR (150 MHz, CDCl$_3$): δ 173.3, 139-127.2 (m, 36C), 80.2 (C-2, C-3'), 79.8 (C-3, C-4'), 75.9 (C-4), 75.8 (C-1), 75.1 (C-5), 74.0, 73.8, 72.5, 71.9, 71.0 (C-1), 51.3 (C-2'), 36.6, 31.9, 30.5, 30.2, 29.8, 29.75, 29.73, 29.69, 29.65, 29.5, 29.4, 29.3, 26.0, 25.7, 22.7, 14.1. MALDI-MS (positive mode, DHB): m/z 1408.6 [M+Na]$^+$. Anal. Calcd for C$_{92}$H$_{135}$NO$_8$ (1382.02): C, 79.89; H, 9.84; N, 1.01. Found: C, 79.98; H, 9.99; N, 1.18.

(g) The product of (f) above (150 mg, 0.108 mmol) and 20% Pd(OH)$_2$/C (150 mg) in MeOH/CH$_2$Cl$_2$/H$_2$O (7.5:7.5:1, 6 mL) was stirred under H$_2$ atmosphere at room temperature for 2 hours. The product precipitated and was dissolved by the addition of a mixture of solvents methanol/CH$_2$Cl$_2$/petroleum ether and with warming. After filtration, the filtrate was concentrated to give colourless solid

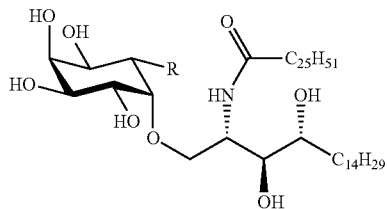

R = H hereafter referred to as Compound 12 ('D-myo-inositol Ceramide Analog') (86 mg, 95% yield). $^1$H NMR (250 MHz, C$_5$D$_5$N): δ 8.45 (d, J=8.5 Hz, 1H), 5.16 (dd, J=8.0, 4.2 Hz, 1H), 4.58-4.43 (m, 4H), 4.33-4.22 (m, 5H), 2.45-2.30 (m, 3H), 1.91-1.77 (m, 3H), 1.28-1.21 (m, 70H), 0.83 (t, J=6.7 Hz, 6H). MALDI-MS (positive mode, DHB): m/z 864.4 [M+Na]$^+$. Anal. Calcd for C$_{50}$H$_{99}$NO$_8$ (841.74): C, 71.30; H, 11.85; N, 1.66. Found: C, 71.41; H, 11.98; N, 1.73.

Compound 13: D-myo-Inositol Ceramide Salt (a) To stirred solution of the product of 12(e) above e.g.

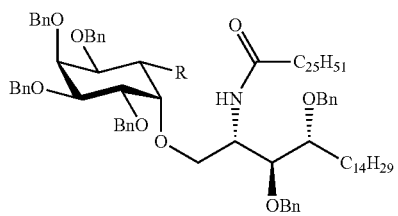

R = OH (200 mg, 0.143 mmol) in DMF/THF (1:1, 2 mL), SO$_3$.NMe$_3$-complex (40 mg, 0.287 mind) was added, and the reaction mixture was stirred for 24 hours at room temperature. After completion of reaction, it was extracted with CH$_2$Cl$_2$ (2×10 mL) and the organic phase was dried and concentrated, which was purified by flash chromatography to give colourless solid. Which was dissolved in MeOH/CH$_2$Cl, (1:1, 2 mL) and passed through the Dowex 50×8H$^+$ ion exchange resin (Na$^+$-form) and eluted with mixture of MeOH/CH$_2$Cl9 (1:1, 100 mL). The solvent was evaporated to obtain solid,

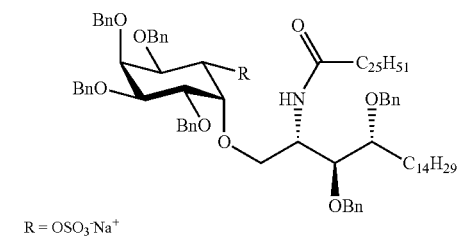

R = OSO$_3$·Na$^+$ which was purified by flash chromatography to give a colourless solid (203 mg, 95% yield). This compound debenzylated using similar procedure as described for compound 12(f) above, to give a colourless solid

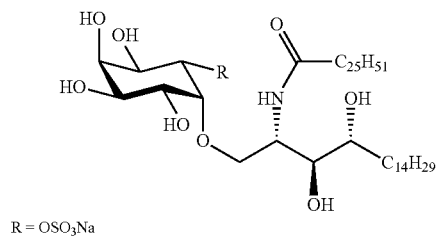

R = OSO$_3$Na

Hereafter referred to as Compound 13 ('D-myo-Inositol Ceramide') (yield: 40% yield). $^1$H NMR (400 MHz, C$_5$D$_5$N:CD$_3$OD): δ 8.50 (d, J=8.5 Hz, 1H), 5.10 (dd, J=10.0, 2.0 Hz, 1H), 4.58-4.55 (m, 2H), 4.48-4.42 (m, 2H), 4.26-4.17 (m, 3H), 4.06-3.99 (m, 2H), 3.91-3.88 (m, 1H), 2.31-2.26 (m, 2H), 1.63-1.10 (m, 72H), 0.90 (t, J=5.7 Hz, 6H). MALDI-MS (negative mode, ATT): m/z 938.7 [M−Na]$^-$. Anal. Calcd for C$_{50}$H$_{98}$NNaO$_{12}$S (959.67): C, 62.53; H, 10.29; N, 1.46. Found: C, 62.59; H, 10.38; N, 1.51.

Compound 14: 4-(S)-Phenyl Threitol Ceramides (a) L-(+)-tartaric acid was converted to a corresponding triflate in accordance with well known procedures, see Wagner, et al., *J. Chem. Soc. Perkins Trans.*, 1, 780 (2001); Su, et al., *Tetrahedron.*, 57 2147 (2001); Surivet, et al., *Tetrahedron Lett.*, 39:7249 (1998) and Surivet, et al., *Tetrahedron.*, 55:1311 (1999), all of which are incorporated by reference. The synthesis of the triflate results in a diastereomeric mixture. This mixture is separated, following the references cited supra, to yield two compounds.

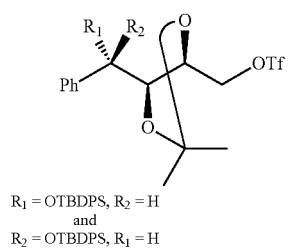

R$_1$ = OTBDPS, R$_2$ = H
and
R$_2$ = OTBDPS, R$_1$ = H (b) The procedure of 1(a) above was repeated with the triflate from (a) above, where R$_1$=OTBDPS and R$_2$=H e.g.

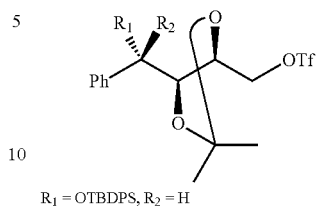

R$_1$ = OTBDPS, R$_2$ = H to give

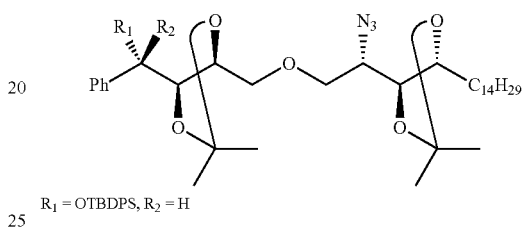

R$_1$ = OTBDPS, R$_2$ = H which was purified via flash chromatography to give as a colorless liquid, in a yield of 84%. R$_f$=0.62 (1:9, ethyl acetate:petroleum ether). [α]$_D^{25}$=+20.5 (c 1.0, CHCl$_3$). $^1$H NMR (250 MHz, CDCl$_3$): δ 7.71-7.17 (m, 15H), 4.90 (d, J=4.5 Hz, 1H), 4.27-4.20 (m, 1H), 4.15-4.06 (m, 1H), 3.95 (dd, J=8.0, 4.5 Hz, 1H), 3.79-3.70 (m, 2H), 3.52 (dt, J=8.7, 2.0 Hz, 1H), 3.40 (t, J=9.0 Hz, 1H), 3.28-3.16 (m, 2H), 1.54-1.20 (m, 26H), 1.42 (s, 3H), 1.37 (s, 3H), 1.32 (s, 3H), 1.28 (s, 3H), 1.06 (s, 9H), 0.88 (t, J=6.5 Hz, 3H). $^{13}$C NMR (62.5 MHz, CDCl$_3$): δ 140.4, 136.07, 136.02, 133.5, 133.2, 129.5, 129.4, 127.7, 127.4, 127.3, 127.2, 127.0, 109.2, 108.1, 81.1, 77.7, 76.8, 75.7, 75.5, 72.8, 72.6, 59.7, 31.9, 29.6, 29.59, 29.53, 29.4, 29.3, 28.0, 27.0, 26.88, 26.82, 26.4, 25.6, 22.6, 19.3, 14.1. MALDI-MS (positive mode, CHCA): m/z 865.2 [M Na]$^+$. Anal. Calcd for C$_{50}$H$_{75}$N$_3$O$_6$Si (842. 23): C, 71.30; H, 8.98; N, 4.99. Found: C, 71.39; H, 9.03; N, 5.07.

(c) The procedure of 1(b) above was repeated using the product of (b) above to give

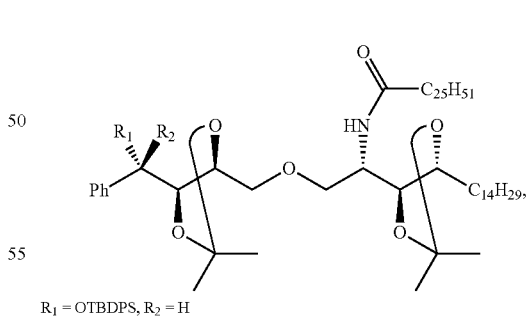

R$_1$ = OTBDPS, R$_2$ = H which was purified via flash chromatography (8:9.2 ethyl acetate:petroleum either), as a colorless solid, in 72% yield. R$_f$=0.52 (1:9, ethyl acetate:petroleum ether). [α]$_D^{25}$=17.9 (c 1.0, CHCl$_3$). NMR (250 MHz, CDCl$_3$): δ 7.69-7.16 (m, 15H), 5.72 (d, J=8.7 Hz, 1H), 4.84 (d, J=4.7 Hz, 1H); 4.19-4.08 (On, 4H), 3.87 (dd, J=7.6, 4.5 Hz, 1H), 3.59 (br. d, J=9.2 Hz, 1H), 3.33 (br, d, =10.5 Hz, 1H), 3.17 (br. d, J=4.5 Hz, 2H), 2.12-2.06 (m, 2H), 1.56-1.25 (m, 72H), 1.40 (s, 3H), 1.31 (s, 3H), 1.30 (s, 3H), 1.19 (s, 3H), 1.05 (s, 9H), 0.89 (t, J=6.7 Hz, 6H). $^{13}$C NMR (62.5 MHz, CDCl$_3$): δ 170.4, 139.5-127.1 (in), 109.1, 108.1, 80.3, 77.6, 77.1, 75.7, 72.6, 71.7, 65.2, 58.9, 31.8, 29.6, 29.5, 29.3, 29.2, 28.0, 26.9, 26.6, 26.5, 26.3, 25.5, 22.6, 20.6, 14.0. MALDI-MS (positive mode, DHB): m/z 1217.7 [M+Na]$^+$. Anal. Calcd for C$_{76}$H$_{27}$NO$_7$Si (1194. 90): C, 76.39; H, 10.71; N, 1.17. Found: C, 76.45; H, 10.81; N, 1.21.

(d) The product of (c) above (200 mg, 0.169 mmol) in THF and 1.0M solution of TBAF (0.2 ml, 0.203 mmol), was stirred at room temperature for 24 hours. The reaction mixture was then taken up in ethyl acetate, washed with water, then a saturated brine solution, and then dried over anhydrous MgSO$_4$, and concentrated. The residue was purified, via flash chromatography, to give

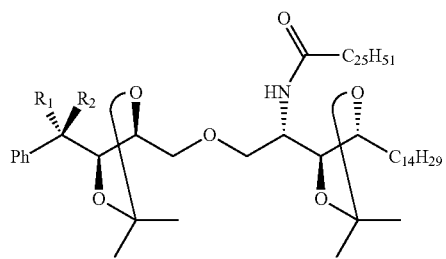

R$_1$ = OH, R$_2$ = H as a colorless solid (132 mg, 82% yield). R$_f$=0.42 (4:6, ethyl acetate:petroleum ether). J=6.7 (c 0.5, CHCl$_3$). $^1$H NMR (250 MHz, CDCl$_3$): δ 7.41-7.32 (m, 5H), 5.68 (d, J=9.0 Hz, 1H), 4.87 (d, J=5.5 Hz, 1H), 4.32-3.96 (m, 5H), 3.60 (dd, J=10.0, 3.8 Hz, 1H), 3.39 (dd, J=10.0, 2.5 Hz, 1H), 3.24 (dd, J=10.5, 5.5 Hz, 1H), 3.14 (dd, J=10.5, 4.0 Hz, 1H), 2.12 (dt, J=7.5, 3.5 Hz, 2H), 1.54-1.25 (m, 72H), 1.43 (s, 3H); 1.41 (s, 3H), 1.38 (s, 3H), 1.33 (s, 3H), 0.88 (t, J=6.7 Hz), 6H). $^{13}$C NMR (62.5 MHz, CDCl$_3$): δ 172.5, 139.5, 128.3, 127.8, 126.1, 109.3, 107.9, 81.0, 77.6, 76.1, 73.0, 72.1, 71.2, 48.1, 36.9, 31.9, 29.6, 29.5, 29.3, 29.0, 27.05, 27.01, 26.4, 25.7, 22.6, 14.1. MALDI-MS (positive mode, CHCA): m/z 979.4 [M+Na]$^+$. Anal. Calcd for C$_{60}$H$_{109}$NO$_7$ (956.51): C, 75.34; H, 11.49; N, 1.46. Found: C, 75.40; H, 11.55; N, 1.51

(e) The procedures of 1(c) above was repeated using the product of (d) above, yielding a colorless solid,

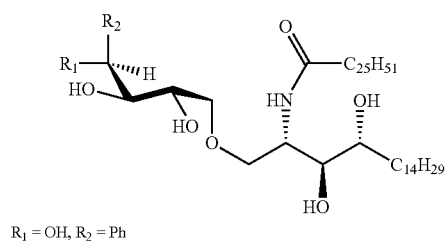

R$_1$ = OH, R$_2$ = Ph hereafter referred to as Compound 14 ('4-(S)-Phenyl Threitol Ceramide'), at a yield of 68%. $^1$H NMR (600 MHz, C$_5$D$_5$N): δ 8.52 (d, J=8.5 Hz, 1H), 7.79-7.27 (m, 5H), 5.39 (d, J=7.8 Hz, 1H), 5.18-4.94 (m, 1H), 4.93-4.91 (m, 1H), 4.30-4.19 (m, 5H), 4.12-4.08 (m, 2H), 2.41 (br. t, J=7.5 Hz, 2H), 1.92-1.25 (m, 72H), 0.87 (t, J=6.5 Hz, 6H). $^{13}$C NMR (150.9 MHz, C$_5$D$_5$N): δ 173.3, 114.4, 128.3, 128.1, 127.2, 76.2, 75.4, 75.2, 74.6, 72.8, 71.3, 70.0, 51.8, 36.8, 32.1, 30.3, 30.0, 29.7, 29.6, 26.6, 26.4, 22.9, 14.3. MALDI-MS (positive mode, CHA): m/z 899.1 [M+Na]$^+$. Anal. Calcd for C$_{54}$H$_{101}$NO$_7$ (876.38): C, 74.01; H, 11.62; N, 1.60. Found: C, 73.98; H, 11.59; N, 1.62.

Compound 15: 4-(R)-Phenyl Threitol Ceramide (a) The procedure of 1(a) above was repeated using the product of 14(a) above, where R$_1$=H and R$_2$=OTBDPS e.g.

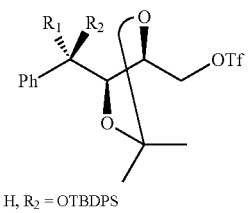

R$_1$ = H, R$_2$ = OTBDPS to give

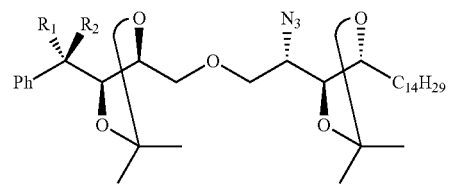

R$_1$ = H, R$_2$ = OTBDPS, 86% which was purified by flash chromatography (7:9.3 ethyl acetate/petroleum ether), as a colorless liquid, in a yield of 86%. R$_f$=0.59 (1:9, ethyl acetate:petroleum ether). [α]$_D^{25}$=−15.0 (c 1.0, CHCl$_3$). $^1$H NMR (250 MHz, CDCl$_3$): δ 7.76-7.14 (m, 15H), 4.82 (d, J=6.5 Hz, 1H), 4.21-4.06 (m, 3H), 3.86 (dd, J=9.5, 5.5 Hz, 1H), 3.87-3.68 (m, 3H), 3.51 (dt, J=9.5, 2.2 Hz, 1H), 3.34 (dd, J=1.0.0, 8.5 Hz, 1H), 1.58-1.25 (m, 26H), 1.41 (s, 3H), 1.36 (s, 3H), 1.33 (s, 3H), 1.31 (s, 3H), 1.04 (s, 9H), 0.87 (t, J=6.7 Hz), $^{13}$C NMR (62.5 MHz, CDCl$_3$): δ 139.5, 136.1, 135.9, 133.6, 133.3, 129.4, 129.3, 127.88, 127.80, 127.4, 127.2, 127.1, 109.1, 108.1, 80.3, 77.7, 77.5, 77.1, 75.7, 72.6, 71.7, 59.7, 31.8, 29.6, 29.5, 29.55, 29.50, 29.47, 29.41, 29.3, 29.2, 28.0, 27.0, 26.6, 26.4, 26.3, 25.5, 25.4, 22.6, 19.3, 14.1. MALDI-MS (positive mode, CHCA): m/z 865.4 [M+Na]$^+$. Anal. Calcd for C$_{50}$H$_{75}$N$_3$O$_6$Si (842. 23): C, 71.30; H, 8.98; N, 4.99. Found: C, 71.42; H, 9.07; N, 5.04.

(b) The procedures of 14(b) above was repeated but using the product of (a) above to give

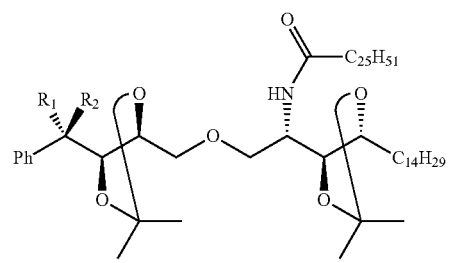

R$_1$ = H, R$_2$ = OTBDPS which was purified by flash chromatography (1:9 ethyl acetate/petroleum ether) the pure compound was obtained as a colorless solid in a yield of 69%. $R_f$=0.49 (1:9, ethyl acetate: petroleum ether). $[\alpha]_D^{25}$=−5.9 (c 1.0, CHCl$_3$). $^1$H NMR (250 MHz, CDCl$_3$): δ 7.77-7.18 (m, 15H), 5.88 (d, J=9.0 Hz, 1H), 4.74 (d, J=6.5 Hz, 1H), 4.10-4.07 (m, 3H), 3.97 (dd, J=8.0, 6.5 Hz, 1H), 3.77 (dt, 5.7, 2.2 Hz, 1H), 3.55 (br. d, J=9.0 Hz, 1H), 3.27 (br. d, J=8.5 Hz, 1H); 3.00-2.97 (m, 2H), 2.16-2.08 (m, 2H), 1.58-1.25 (M, 72H), 1.39 (s, 3H), 1.33 (s, 3H), 1.29 (s, 3H), 1.18 (s, 3H), 1.04 (s, 9H), 0.88 (t, J=6.5 Hz, 6H). $^{13}$C NMR (62.5 MHz, CDCl$_3$): δ 172.6, 139.6, 136.1, 135.9, 133.6, 133.2, 129.4, 127.9, 127.4, 127.3, 127.2, 109.2, 107.7, 80.6, 77.7, 77.1, 76.9, 75.7, 72.0, 70.8, 49.4, 36.9, 31.9, 29.7, 29.5, 29.3, 29.2, 28.4, 27.0, 26.6, 26.4, 26.3, 25.5, 25.4, 22.6, 19.3, 14.1. MALDI-MS (positive mode, DHB): m/z 1217.7 [M+Na]$^+$. Anal. Calcd for C$_{76}$H$_{127}$NO$_7$Si (1194. 90): C, 76.39; H, 10.71; N, 1.17. Found: C, 76.41; H, 10.75; N, 1.22.

(c) The procedures of 14(c) above was repeated but using the product of (b) above to give

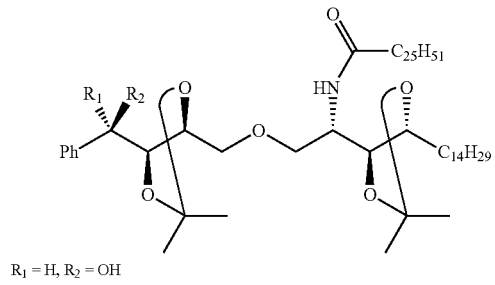

R$_1$ = H, R$_2$ = OH which was purified by flash chromatography (3:7 ethyl acetate/petroleum ether), the compound was obtained as a colourless solid, in a yield of 85%. $R_f$=0.40 (4:6, ethyl acetate: petroleum ether). $[\alpha]_D^{25}$=−3.1 (c 0.5, CHCl$_3$). $^1$H NMR (250 MHz, CDCl$_3$): δ 7.38-7.36 (m, 5H), 5.58 (d, J=9.0 Hz, 1H), 4.69 (d, J=5.2 Hz, 1H), 4.13-3.91 (m, 5H), 3.60 (dd, J=9.7, 3.2 Hz, 1H), 3.33 (dd, J=9.7, 2.5 Hz, 1H), 3.21 (dd, J=10.5, 5.2 Hz, 1H), 3.10 (dd, J=10.5, 3.5 Hz, 1H), 2.12 (dt, =7.5, 3.2 Hz, 2H), 1.58-1.24 (m, 72H), 1.42 (s, 6H), 1.39 (s, 3H), 1.31 (s, 3H), 0.87 (t, J=6.5 Hz, 6H). $^{13}$C NMR (62.5 MHz, CDCl$_3$): δ 172.4, 139.6, 128.5, 128.3, 126.9, 109.9, 107.8, 81.9, 77.7, 77.2, 76.8, 75.9, 74.9, 71.7, 71.1, 48.1, 36.9, 31.9, 29.7, 29.5, 29.3, 28.9, 28.0, 27.3, 27.2, 26.4, 25.8, 25.7, 22.6, 14.1. MALDI-MS (positive mode, CHCA): m/z 979.5 [M+Na]$^+$. Anal. Calcd for C$_{60}$H$_{109}$NO$_7$ (956.51): C, 75.34; H, 11.49; N, 1.46. Found: C, 75.43; H, 11.48; N, 1.44.

(d) The procedures of 14(d) above was repeated but using the product of (c) above to give

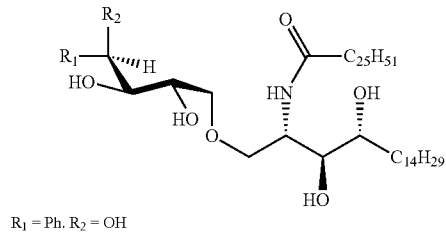

R$_1$ = Ph, R$_2$ = OH as a colourless solid, hereafter referred to as Compound 15 ('4-(R)-Phenyl Threitol Ceramide') obtained at a yield of 60%. $^1$H NMR (600 MHz, C$_5$D$_5$N): δ 8.46 (d, J=8.5 Hz, 1H), 7.82-7.28 (m, 5H), 5.46 (d, J=5.4 Hz, 1H), 5.14-511 (m. 1H), 4.25-4.00 (m, 8H), 2.38 (m, 2H), 1.88-1.25 (m, 72H), 0.86 (t, J=6.5 Hz, 6H). $^{13}$C NMR (150.9 MHz, C$_5$D$_5$N): δ 173.3, 144.4, 128.4, 127.7, 127.3, 76.6, 76.2, 75.3, 74.4, 72.7, 71.2, 71.0, 51.7, 36.8, 33.8, 32.1, 30.3, 30.1, 30.0, 29.8, 29.7, 29.6, 26.6, 26.3, 22.9, 14.2. MALDI-MS (positive mode, CHCA): m/z 899.5 [M+Na]$^+$. Anal. Calcd for C$_{54}$H$_{101}$NO$_7$ (876.38): C, 74.01; H, 11.62; N, 1.60. Found: C, 74.05; H, 11.68; N, 1.65.

Compound 16: 4-(S)-Phenyl Threitol-22-(Z)-Ceramide (a) The procedure of 1(b) above was repeated using 22-(Z)-hexacosenoic acid with the product of 9(b) above e.g.

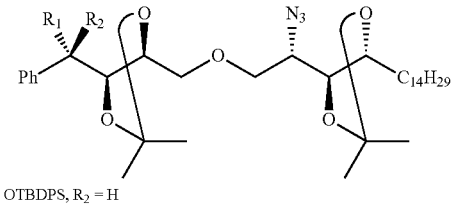

R$_1$ = OTBDPS, R$_2$ = H to give

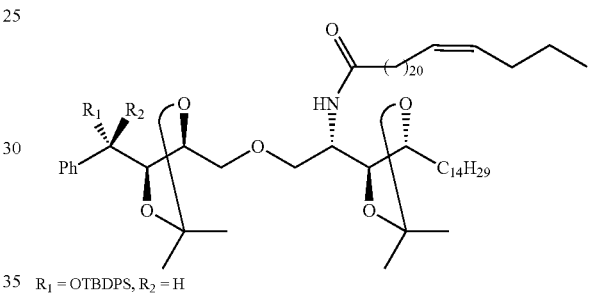

R$_1$ = OTBDPS, R$_2$ = H which was purified by flash chromatography (5:9.5, ethyl acetate:toluene) as a colourless solid (yield: 72%). $R_f$=0.53 (5:9.5, ethyl acetate:toluene). $[\alpha]_D^{25}$=+24.6 (c 1.0, CHCl$_3$). $^1$H NMR (250 MHz, CDCl$_3$): δ 7.70-7.15 (m, 15H), 5.65 (d, J=8.5 Hz, 1H), 5.36-5.31 (m, 2H), 4.83 (d, J=4.5 Hz, 1H), 4.17-4.06 (m, 4H), 3.84 (dd, J=7.5, 4.5 Hz, 1H), 3.58 (dd, J=9.2, 2.2 Hz, 1H), 3.38 (dd, J=9.7, 2.1 Hz, 1H), 3.16 (br, d, J=4.5 Hz, 2H), 2.13-1.94 (m, 6H), 1.61-1.17 (m, 76H), 1.04 (s, 9H), 0.91-0.83 (m, 6H). $^{13}$C NMR (62.5 MHz, CDCl$_3$): δ 172.2, 140.3-127.0 (m, 17C), 109.2, 107.6, 81.5, 77.7, 76.8, 75.8, 75.6, 73.0, 70.9, 60.2, 48.1, 36.8, 31.8, 29.7, 29.6, 29.5, 29.4, 29.35, 29.31, 29.2, 28.9, 28.0, 27.15, 27.11, 27.0, 26.8, 26.4, 25.7, 25.6, 22.8, 22.6, 14.1, 13.8. MALDI-MS (positive mode, DHB): m/z 1214.3 [M+Na]$^+$.

(b) The procedure of 14(c) above was repeated using the product of (a) above and purified by flash chromatography (4:6 ethyl acetate:petroleum ether) to give

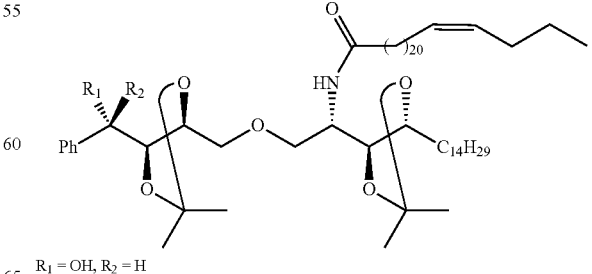

R$_1$ = OH, R$_2$ = H as colourless solid (yield: 98%). $R_f$=0.31 (3:7, ethyl acetate: petroleum ether). $[\alpha]_D^{25}$=+14.9 (c 1.0, CHCl$_3$). $^1$H NMR (250 MHz, CDCl$_3$): δ 7.40-7.26 (m, 5H), 5.66 (d, J=9.0 Hz, 1H), 5.37-5.33 (m, 2H), 4.88 (dd, J=5.5, 2.7 Hz, 1H), 4.23-3.96 (m, 5H), 3.60 (dd, J=10.0, 4.0 Hz, 1H), 3.39 (dd, J=9.5, 2.2 Hz, 1H), 3.23 (dd, J=10.5, 5.2 Hz, 1H), 3.13 (dd, J=10.5, 4.0 Hz, 1H), 3.09 (d, J=2.7 Hz, 1H), 2.12 (dt, J=10.5, 7.5, 3.5 Hz, 2H), 2.05-1.96 (m, 4H), 1.60-1.25 (m, 76H), 0.92-0.85 (m, 6H). $^{13}$C NMR (62.5 MHz, CDCl$_3$): δ 172.4, 139.6, 130.0, 129.5, 128.2, 126.1, 109.2, 107.8, 80.9, 77.6, 76.6, 76.0, 73.0, 72.0, 71.1, 48.1, 36.8, 31.8, 29.7, 29.67, 29.60, 29.5, 29.38, 29.33, 29.27, 29.24, 28.8, 27.9, 27.1, 27.0, 26.9, 26.4, 25.69, 25.67, 22.8, 22.6, 14.0, 13.7. MALDI-MS (positive mode, DHB): m/z 976.7 [M+Na]$^+$.

(c) The procedure of 14(d) above was repeated using the product of (b) above to obtain a colourless solid

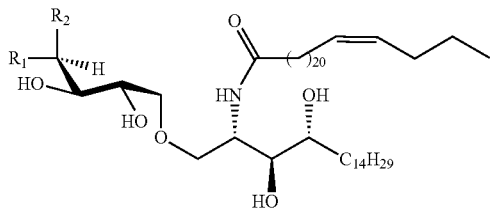

$R_1$ = OH, $R_2$ = Ph hereafter referred to as Compound 16 ('4-(S)-Phenyl Threitol-22-(Z)-Ceramide'), (yield: 67%). $^1$H NMR (250 MHz, C$_5$D$_5$N): δ 8.43 (d, J=8.7 Hz, 1H), 7.70-7.16 (m, 5H), 5.39-5.28 (m, 3H), 5.08-5.02 (m, 1H), 4.89-4.79 (m, 1H), 4.23-4.07 (m, 5H), 4.05-3.95 (m, 2H), 2.30 (br. t, J=7.5 Hz, 2H), 1.99-1.87 (m, 4H), 1.80-1.67 (m, 4H), 1.17-1.13 (m, 60H), 0.78-0.73 (m, 6H). MALDI-MS (positive mode, DHB): m/z 897.1 [M+Na]$^+$. Anal. Calcd for C$_{54}$H$_{99}$NO$_7$ (873.74): C, 74.18; H, 11.41; N, 1.60. Found: C, 74.16; H, 11.49; N, 1.68.

Compound 17: 4-(R)-Phenyl Threitol-22-(Z)-Ceramide (a) The procedure of 1(b) was repeated using 22-(Z)-hexacosenoic acid with the product of 15(b) above e.g.

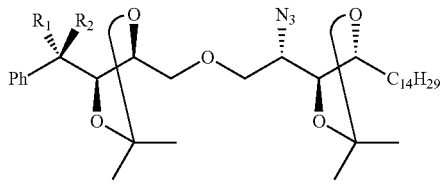

$R_1$ = H, $R_2$ = OTBDPS to give

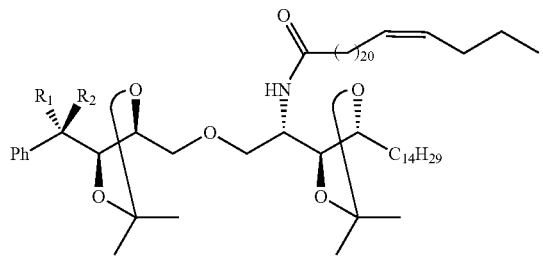

$R_1$ = H, $R_2$ = OTBDPS which was purified by flash chromatography (5:9.5, ethyl acetate:toluene) as a colourless solid (yield: 75%). $R_f$=0.57 (5:9.5, ethyl acetate:toluene). $[\alpha]_D^{25}$=−6.0 (c 1.0, CHCl$_3$). $^1$H NMR (250 MHz, CDCl$_3$): δ 7.75-7.18 (m, 15H), 5.68 (d, J=8.0 Hz, 1H), 5.40-5.33 (m, 2H), 4.72 (d, J=6.5 Hz, 1H), 4.12-4.00 (m, 3H), 3.93 (dd, J=8.0, 6.5 Hz, 1H), 3.79-3.72 (m, 1H), 3.53 (br. d, J=9.5 Hz, 1H), 3.24 (br. d, J=9.5 Hz, 1H), 3.02-2.91 (m, 2H), 2.16-1.96 (m, 6H), 1.60-1.25 (m, 76H), 1.04 (s, 9H), 0.92-0.85 (, 6H). $^{13}$C NMR (62.5 MHz, CDCl$_3$): δ 172.3, 139.6-127.2 (m, 17C), 109.1, 107.7, 80.6, 77.7, 77.1, 76.9, 75.7, 72.1, 70.8, 48.1, 36.9, 31.9, 29.74, 29.70 29.6, 29.5, 29.39, 29.35, 29.30, 29.2, 29.0, 28.0, 27.2, 26.9, 26.7, 26.4, 25.8, 25.7, 22.8, 22.6, 14.1, 13.7. MALDI-MS (positive mode, DHB): m/z 1214.4 [M+Na]$^+$.

(b) The procedure of 15(c) was repeated using the product of (a) above and purified by flash chromatography (4:6 ethyl acetate:petroleum ether) to give pure

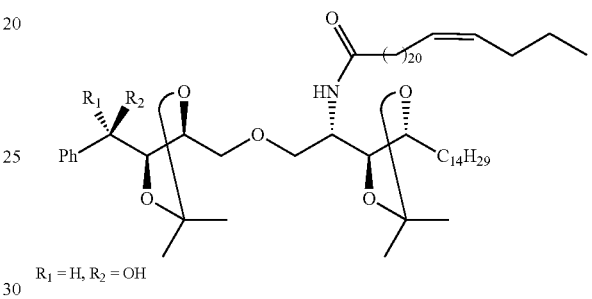

$R_1$ = H, $R_2$ = OH as a colourless solid (yield: 98%). $R_f$=0.32 (3:7, ethyl acetate: petroleum ether). $[\alpha]_D^{25}$=+5.5 (c 1.0, CHCl$_3$). $^1$H NMR (250 MHz, CDCl$_3$): δ 7.39-7.30 (m, 5H), 5.56 (d, J=9.2 Hz, 1H), 5.37-5.32 (m, 2H), 4.68 (t, J=4.5 Hz, 1H), 4.13-3.94 (m, 5H), 3.59 (dd, J=9.5, 3.5 Hz, 1H), 3.32 (dd, J=9.5, 3.5 Hz, 1H), 3.20 (dd, J=10.5, 5.2 Hz, 1H), 3.10 (dd, J=10.2, 3.8 Hz, 1H), 2.92 (d, J=4.5 Hz, 1H), 2.11 (dt, =10.5, 7.5, 3.5 Hz, 2H), 2.03-1.95 (m, 4H), 1.60-1.24 (m, 76H), 0.91-0.84 (m, 6H). $^{13}$C NMR (62.5 MHz, CDCl$_3$): δ 172.3, 139.6, 130.0, 129.5, 128.4, 126.9, 109.8, 107.7, 81.8, 77.6, 76.7, 75.8, 74.9, 71.7, 71.1, 48.0, 36.8, 31.8, 29.7, 29.69, 29.60, 29.5, 29 38, 29.32, 29.28, 29.27, 29.24, 28.9, 27.9, 27.29, 27.22, 27.1, 26.4, 25.7, 25.6, 22.8, 22.6, 14.0, 13.7. MALDI-MS (positive mode, DHB): m/z 976.6 [M+Na]$^+$.

(c) The procedure of 15(d) was repeated using the product of (b) above to obtain a colourless solid

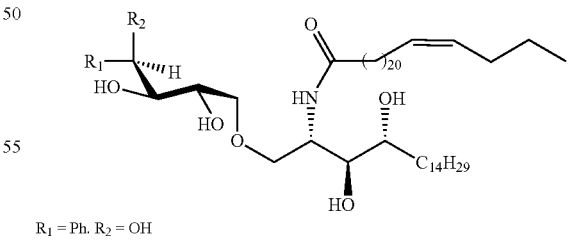

$R_1$ = Ph, $R_2$ = OH hereafter referred to as Compound 17 ('4-(R)-Phenyl Threitol-22-(Z)-Ceramide'), (yield: 63%). $^1$H NMR (250 MHz, C$_5$D$_5$N): δ 8.42 (d, J=8.7 Hz, 1H), 7.73-7.16 (m, 5H), 5.38-5.30 (m, 3H), 5.05-5.00 (m, 1H), 4.19-3.98 (m, 7H), 3.92-3.86 (m, 1H), 2.28 (br. t, J=7.5 Hz, 2H), 1.98-1.87 (m, 4H), 1.80-1.65 (m, 4H), 1.17-1.12 (m, 60H), 0.78-0.71 (m, 6H). MALDI-MS (positive mode, DHB): m/z 897.4 [M+Na]$^+$.

Anal. Calcd for $C_{54}H_{99}NO_7$ (873.74): C, 74.18; H, 11.41; N, 1.60. Found: C, 74.11; H, 11.51; N, 1.66.

Synthesis of (19Z,22Z)-Hexacosadienoic Acid (a) The procedure for 'Synthesis 22-(Z)-Hexacosanoic acid', step (a) above was repeated from 11-bromoundecanoic acid to give

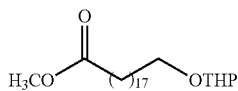

in 97% yield, $^1$H NMR (250 MHz, CDCl$_3$): δ 4.58 (t, J=3.2 Hz, 1H), 3.92-3.83 (m, 1H), 3.78-3.72 (m, 1H), 3.65 (s, 3H), 3.52-3.46 (m, 1H), 3.42-3.36 (m, 1H), 2.30 (t, J=7.5 Hz, 2H), 1.88-1.15 (m, 10H), 1.25 s, 28H). $^{13}$C NMR (62.5 MHz, CDCl$_3$): δ 174.2, 98.7, 67.6, 62.2, 51.3, 34.0, 30.7, 29.7, 29.63, 29.60, 29.5, 29.45, 29.40, 29.2, 29.1, 26.2, 25.4, 24.9, 19.6. MALDI-MS (positive mode, CHCA): m/z 436.1 [M+Na]$^+$.

(b) The procedure from the 'Synthesis 22-(Z)-Hexacosanoic acid', step (b) above, was repeat for (a) above to give

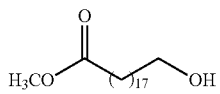

in 98% yield, $^1$H NMR (250 MHz, CDCl$_3$): δ 3.67 (s, 3H), 3.63 (t, J=6.5 Hz, 2H), 2.30 (t, J=7.5 Hz, 1H), 1.64-4.51 (m, 4H), 1.25 (br. s, 26H). $^{13}$C NMR (62.5 MHz, CDCl$_3$): δ 174.3, 63.0, 51.4, 34.0, 32.7, 29.63, 29.60, 29.5, 29.58, 29.56, 29.4, 29.2, 29.1, 25.7, 24.9. MALDI-MS (positive mode, CHCA): m/z 351.9 [M+Na]$^+$.

(c) The procedure from the 'Synthesis 22-(Z)-Hexacosanoic acid', step (c) above, was repeat for (b) above to give

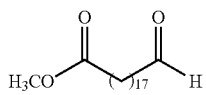

in 90% yield, $^1$H NMR (250 MHz, CDCl$_3$): δ 9.76 (s, 1H), 3.66 (s, 3H), 2.39 (dt, J=14.0, 7.5, 2.0 Hz, 2H), 2.26 (t, J=7.5 Hz, 2H), 1.66-1.56 (m, 4H), 1.25 (br. s, 26H). $^{13}$C NMR (62.5 MHz, CDCl$_3$): δ 202.6, 173.4, 50.7, 43.4, 315, 29.29, 29.23, 29.08, 29.01, 28.9, 28.79, 28.76, 24.5, 21.6. ESI-MS (positive mode) (326.2): 349.3 [M+Na]$^+$.

(d) The procedure from the 'Synthesis 22-(Z)-Hexacosanoic acid', step (d) above, was repeat for (c) above to give

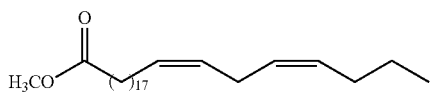

in 98% yield, $^1$H NMR (250 MHz, CDCl$_3$): δ 5.37-5.34 (m, 4H), 3.66 (s, 3H), 2.78 (t, J=6.2 Hz, 2H), 2.30 (t, J=7.5 Hz, 2H), 2.08-1.99 (m. 4H), 1.64-1.58 (m, 2H), 1.42-1.25 (m, 30H), 0.91 (t, 7.5 Hz, 31-1). $^{13}$C NMR (62.5 MHz, CDCl$_3$): δ 174.1, 130.0, 129.7, 128.0, 127.8, 51.2, 34.0, 29.64, 29.60, 29.55, 29.51, 29.4, 29.27, 29.22, 29.1, 27.1, 25.5, 24.8, 22.7, 13.7.

(e) The product of (d) above (1.23 g, 3.022 mmol) in THF (10 mL) and 2 N potassium hydroxide (12 mL) was heated to reflux for 8 h, and acidified with 2 N hydrochloric acid (~pH 1-2). Extracted with diethyl ether (2×30 mL), dried and concentrated to give colorless solid which was recrystallized from glacial acetic acid to give colorless crystals (yield: 52%), and mother liquid was concentrated and purified by flash chromatography to give

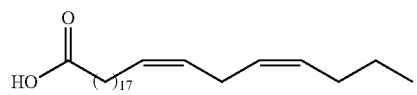

(19Z,22Z)-Hexacosadienoic acid as colorless crystals in 42% yield, $^1$H NMR (250 MHz, CDCl$_3$): δ 5.37-3.32 (m, 4H), 2.76 (t, J=6.2 Hz, 2H), 2.33 (t, J=7.5 Hz, 2H), 2.06-1.98 (m, 4H), 1.67-1.55 (m, 2H), 1.32-1.23 (m, 30H), 0.90 (t, J=7.5 Hz, 3H). $^{13}$C NMR. (62.5 MHz, CDCl$_3$): δ 180.1, 130.1, 129.8, 128.1, 127. 9, 34.0, 29.6, 29.59, 29.55, 29.4, 29.3, 29.2, 29.0, 27.2, 25.6, 24.6, 22.8, 13.8. BSI-MS (negative mode) (392.3): 391.4 [M-H]$^-$.

Compound 18: Threitol-(19Z,22Z)-Ceramide (a) The procedure of 1(b) above was repeated using with (19Z,22Z)-Hexacosadienoic acid and the product of 3(b) e.g.

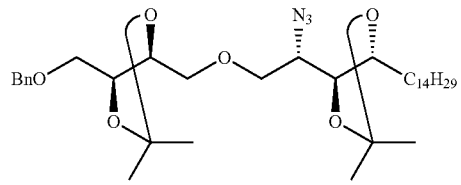

to give

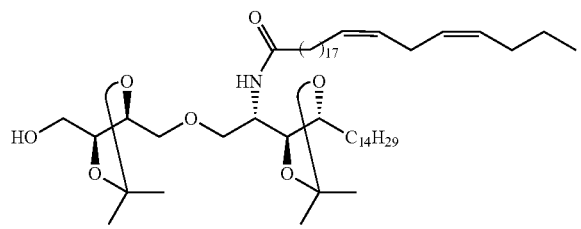

colourless liquid, which is solidifies upon standing. (yield: 71%). R$_f$=0.24 (3:7, ethyl acetate:petroleum ether). $[α]_D^{25}$=+13.6 (c 1.0, CHCl$_3$). $^1$H NMR (250 MHz, CDCl$_3$): δ 5.73 (d, J=9.5 Hz, 1H), 5.43-5.33 (m, 4H), 4.24-4.15 (m, 1H), 4.08-3.99 (m, 3H), 3.92-3.86 (m, 1H), 3.80-3.65 (m, 5H), 3.60-3.54 (m, 2H), 2.77 (t, J=6.2 Hz, 2H), 2.14 (dt, J=10.5, 7.5, 3.0 Hz, 2H), 2.07-1.99 (m, 4H), 1.61-1.24 (m, 74H), 0.93-0.84 (m, 6H). $^{13}$C NMR (62.5 MHz, CDCl$_3$): δ 172.5, 130.0, 129.7, 128.0, 127.8, 109.2, 107.9, 79.1, 77.6, 76.6, 76.1, 71.8, 71.6, 62.3, 48.1, 36.8, 31.8, 29.6, 29.5, 29.4, 29.36, 29.30, 29.26, 29.21, 28.9, 27.8, 27.1, 26.9, 26.4, 25.67, 25.63, 25.5, 22.7, 22.6, 14.0, 13.7. MALDI-MS (positive mode, DHB): m/z 899.1 [M+Na]$^+$.

(b) The procedure of 1(c) above was followed using the product of (a) above to give

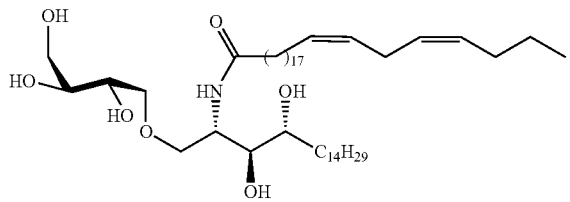

colourless solid (yield: 67%), hereafter referred to as Compound 18 ('Threitol-(19Z, 22Z)-Ceramide'). $^1$H NMR (250 MHz, $C_5D_5N$): δ 8.65 (d, J=8.5 Hz, 1H), 5.66-5.55 (m, 4H), 5.30-5.24 (m, 1H), 4.63-4.45 (m, 1H), 4.42-4.32 (m, 9H), 4.18 (d, J=5.5 Hz, 2H), 3.01 (t, J=6.2 Hz, 2H), 2.54 (t, J=7.5 Hz, 2H), 2.28-2.14 (m, 4H), 2.03-1.87 (m, 4H), 1.48-1.36 (m, 58H), 1.02-0.97 (m, 6H). MALDI-MS (positive mode, Matrix CHCA): m/z 819.8 [M+Na]$^+$.

The invention claimed is:

1. A composition useful in stimulating a T cell response comprising a compound of formula:

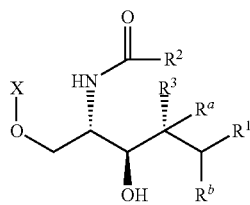

and an immunostimulatory molecule
in which
$R^1$ represents a hydrophobic moiety adapted to occupy the C' channel of human CD1d,
$R^2$ represents a hydrophobic moiety adapted to occupy the A' channel of human CD1d, such that $R^1$ fills at least at least 30% of the occupied volume of the C' channel compared to the volume occupied by the terminal $nC_{14}H_{29}$ of the sphingosine chain of α-galactosylceramide when bound to human CD1d and $R^2$ fills at least 30% of the occupied volume of the A' channel compared to the volume occupied by the terminal $nC_{25}H_{51}$ of the acyl chain of α-galactosylceramide when bound to human CD1d
$R^3$ represents hydrogen or OH,
$R^a$ and $R^b$ each represent hydrogen and in addition, when $R^3$ represents hydrogen, $R^a$ and $R^b$ together may form a single bond,
X represents or —CHA(CHOH)$_n$Y or —P(=O)(O$^-$)OCH$_2$(CHOH)$_m$Y, in which Y represents CHB$_1$B$_2$,
n represents an integer from 1 to 4, m represents 0 or 1,
A represents hydrogen,
one of B$_1$ and B$_2$ represents H, OH or phenyl, and the other represents hydrogen or one of B$_1$ and B$_2$ represents hydroxyl and the other represents phenyl,
in addition, when n represents 4, then A together with one of B$_1$ and B$_2$ together forms a single bond and the other of B$_1$ and B$_2$ represents H, OH or OSO$_3$H
and pharmaceutically acceptable salts thereof.

2. The composition of claim 1, wherein said T cell response is a CTL response.

3. The composition of claim 1, wherein said immunostimulatory molecule is a protein, peptide, or nucleic acid molecule.

4. The composition of claim 3, wherein said protein or peptide is a tumor antigen.

5. The composition of claim 4, wherein said tumor antigen is MAGE-A1, MAGE-A2, MAGE-A3, MAGE-A4, MAGE-A5, MAGE-A6, MAGE-A7, MAGE-A8, MAGE-A9, MAGE-A10, MAGE-A11, MAGE-A12, MAGE-A13, GAGE-1, GAGE-2, GAGE-3, GAGE-4, GAGE-5, GAGE-6, GAGE-7, GAGE-8, BAGE-1, RAGE-1, LB33/MUM-1, PRAME, NAG, MAGE-Xp2 (MAGE-B2), MAGE-Xp3 (MAGE-B3), MAGE-Xp4 (MAGE-B4), tyrosinase, brain glycogen phosphorylase, Melan-A, MAGE-C1, MAGE-C2, NY-ESO-1, LAGE-1, SSX-1, SSX-2(HOM-MEL-40), SSX-1, SSX-4, SSX-5, SCP-1 or CT-7.

6. A method for inducing a T cell response in a subject in need thereof, comprising administering an amount of the composition of claim 1 to said subject in an amount sufficient to induce said T cell response.

7. A method for inducing a T cell response in a subject in need thereof, comprising administering an amount of the composition of claim 5 to said subject in an amount sufficient to induce said T cell response.

* * * * *